US009985226B2

(12) United States Patent
Stoessel et al.

(10) Patent No.: US 9,985,226 B2
(45) Date of Patent: May 29, 2018

(54) TRIPHENYLENE-BASED MATERIALS FOR ORGANIC ELECTROLUMINESCENT DEVICES

(75) Inventors: Philipp Stoessel, Frankfurt am Main (DE); Dominik Joosten, Frankfurt am Main (DE); Arne Buesing, Frankfurt am Main (DE)

(73) Assignee: Merck Patent GmbH (DE)

( * ) Notice: Subject to any disclaimer, the term of this patent is extended or adjusted under 35 U.S.C. 154(b) by 787 days.

(21) Appl. No.: 13/879,530

(22) PCT Filed: Sep. 16, 2011

(86) PCT No.: PCT/EP2011/004654
§ 371 (c)(1),
(2), (4) Date: Apr. 15, 2013

(87) PCT Pub. No.: WO2012/048781
PCT Pub. Date: Apr. 19, 2012

(65) Prior Publication Data
US 2013/0200359 A1 Aug. 8, 2013

(30) Foreign Application Priority Data

Oct. 15, 2010 (DE) .................. 10 2010 048 608

(51) Int. Cl.
*H01L 51/00* (2006.01)
*C07C 211/61* (2006.01)
(Continued)

(52) U.S. Cl.
CPC .......... *H01L 51/0094* (2013.01); *C07C 13/62* (2013.01); *C07C 211/58* (2013.01); *C07C 211/61* (2013.01); *C07D 209/56* (2013.01); *C07D 209/80* (2013.01); *C07D 209/86* (2013.01); *C07D 209/90* (2013.01);
(Continued)

(58) Field of Classification Search
CPC .. C07D 307/91; C07D 313/06; C07D 333/50; C07D 333/76; C07D 401/10; C07D 403/04; C07D 403/14; C07D 405/10; C07D 405/14; C07D 409/04; C07D 409/10; C07D 409/14; C07F 15/0033; C07F 15/0086; C07F 5/027; C07F 7/025; C07F 7/0807; C07F 7/0812; C07F 9/5022; C07F 9/5325; C07F 9/587; C09B 1/00; C09B 57/00; C09B 57/001; C09B 57/007; C09B 57/008; C09B 57/10; C09K 11/06; C09K 2211/1416; C09K 2211/1433; C09K 2211/145; C09K 2211/1458; C09K 2211/1491; H01L 551/0056; H01L 51/0061; H01L 51/0072; H01L 51/0074; H01L 51/0094; H05B 33/14; Y02E 10/549
See application file for complete search history.

(56) References Cited

U.S. PATENT DOCUMENTS

| 5,077,142 A | 12/1991 | Sakon et al. |
| 7,282,275 B2 * | 10/2007 | Wolk ............ C09K 11/06 252/301.16 |
| 7,674,533 B2 | 3/2010 | Sakamoto et al. |
| 8,318,395 B2 | 11/2012 | Saitoh et al. |
| 8,628,862 B2 | 1/2014 | Schaefer et al. |

(Continued)

FOREIGN PATENT DOCUMENTS

| CN | 1547597 A | 11/2004 |
| CN | 1756824 A | 4/2006 |

(Continued)

OTHER PUBLICATIONS

Machine translation for JP 2004-018665 A (publication date: Jan. 2004).*

(Continued)

*Primary Examiner* — Dawn L Garrett
(74) *Attorney, Agent, or Firm* — Drinker Biddle & Reath LLP

(57) ABSTRACT

The present invention relates to compounds of the formula (1) and (2)

formula (1)

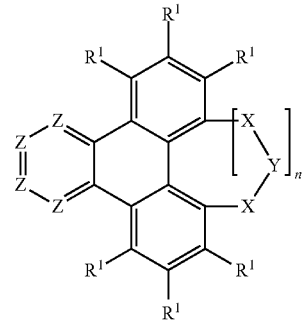

formula (2)

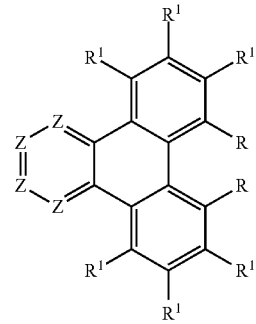

which are suitable for use in electronic devices, in particular organic electroluminescent devices.

20 Claims, No Drawings

(51) Int. Cl.

| | | |
|---|---|---|
| C07C 13/62 | (2006.01) |
| C07C 211/58 | (2006.01) |
| C07F 7/02 | (2006.01) |
| C07D 409/14 | (2006.01) |
| C07D 209/80 | (2006.01) |
| C07D 209/90 | (2006.01) |
| C07D 333/76 | (2006.01) |
| C07D 409/10 | (2006.01) |
| C07D 401/10 | (2006.01) |
| C07D 403/04 | (2006.01) |
| C07F 15/00 | (2006.01) |
| C07D 209/56 | (2006.01) |
| C07D 209/86 | (2006.01) |
| C07D 213/53 | (2006.01) |
| C07D 251/24 | (2006.01) |
| C07D 307/77 | (2006.01) |
| C07D 307/91 | (2006.01) |
| C07D 313/06 | (2006.01) |
| C07D 333/50 | (2006.01) |
| C07D 403/14 | (2006.01) |
| C07D 405/10 | (2006.01) |
| C07D 405/14 | (2006.01) |
| C07D 409/04 | (2006.01) |
| C07F 5/02 | (2006.01) |
| C07F 7/08 | (2006.01) |
| C07F 9/50 | (2006.01) |
| C07F 9/53 | (2006.01) |
| C07F 9/58 | (2006.01) |
| C09K 11/06 | (2006.01) |
| H05B 33/14 | (2006.01) |
| C09B 57/00 | (2006.01) |
| C09B 57/10 | (2006.01) |
| C09B 1/00 | (2006.01) |

(52) U.S. Cl.
CPC ......... *C07D 213/53* (2013.01); *C07D 251/24* (2013.01); *C07D 307/77* (2013.01); *C07D 307/91* (2013.01); *C07D 313/06* (2013.01); *C07D 333/50* (2013.01); *C07D 333/76* (2013.01); *C07D 401/10* (2013.01); *C07D 403/04* (2013.01); *C07D 403/14* (2013.01); *C07D 405/10* (2013.01); *C07D 405/14* (2013.01); *C07D 409/04* (2013.01); *C07D 409/10* (2013.01); *C07D 409/14* (2013.01); *C07F 5/027* (2013.01); *C07F 7/025* (2013.01); *C07F 7/0807* (2013.01); *C07F 7/0812* (2013.01); *C07F 9/5022* (2013.01); *C07F 9/5325* (2013.01); *C07F 9/587* (2013.01); *C07F 15/0033* (2013.01); *C07F 15/0086* (2013.01); *C09B 1/00* (2013.01); *C09B 57/00* (2013.01); *C09B 57/001* (2013.01); *C09B 57/007* (2013.01); *C09B 57/008* (2013.01); *C09B 57/10* (2013.01); *C09K 11/06* (2013.01); *H01L 51/0056* (2013.01); *H01L 51/0061* (2013.01); *H01L 51/0072* (2013.01); *H01L 51/0074* (2013.01); *H05B 33/14* (2013.01); *C09K 2211/145* (2013.01); *C09K 2211/1416* (2013.01); *C09K 2211/1433* (2013.01); *C09K 2211/1458* (2013.01); *C09K 2211/1491* (2013.01); *Y02E 10/549* (2013.01)

(56) References Cited

U.S. PATENT DOCUMENTS

| | | | |
|---|---|---|---|
| 8,968,887 B2 | 3/2015 | Ma et al. | |
| 2003/0091862 A1* | 5/2003 | Tokito | C08G 61/02 428/690 |
| 2003/0219625 A1 | 11/2003 | Wolk et al. | |
| 2004/0076852 A1 | 4/2004 | Cheng et al. | |
| 2004/0076853 A1* | 4/2004 | Jarikov | C09K 11/06 428/690 |
| 2006/0063027 A1 | 3/2006 | Vestweber et al. | |
| 2009/0105447 A1* | 4/2009 | Schafer | C08G 61/12 528/403 |
| 2010/0249349 A1* | 9/2010 | Chebotareva | C08G 61/00 526/259 |
| 2010/0289406 A1* | 11/2010 | Ma | C07D 221/18 313/504 |
| 2010/0327270 A1 | 12/2010 | Buesing et al. | |
| 2011/0084599 A1* | 4/2011 | Brooks | C07C 15/38 313/504 |
| 2011/0186821 A1* | 8/2011 | Schafer | C07D 239/70 257/40 |
| 2011/0210316 A1* | 9/2011 | Kadoma | C07D 403/10 257/40 |
| 2013/0175519 A1 | 7/2013 | Yamada et al. | |

FOREIGN PATENT DOCUMENTS

| | | |
|---|---|---|
| CN | 101142275 A | 3/2008 |
| CN | 101379110 A | 3/2009 |
| CN | 101808964 A | 8/2010 |
| CN | 101848882 A | 9/2010 |
| DE | 102008008953 A1 | 8/2009 |
| EP | 1424350 A1 | 6/2004 |
| EP | 1978022 A1 | 10/2008 |
| JP | 2004-018665 A | 1/2004 |
| JP | 2005-071983 A | 3/2005 |
| JP | 2005071983 A | 3/2005 |
| JP | 2007-112729 A | 5/2007 |
| JP | 2007-308476 A | 11/2007 |
| JP | 2012-082187 A | 4/2012 |
| WO | WO 2009/021107 A1 * | 2/2009 |
| WO | WO-2009/037155 A1 | 3/2009 |
| WO | WO-2011/137157 A1 | 11/2011 |

OTHER PUBLICATIONS

Pummerer, Rudolf et al., Polymerization processes. Condensation of 1,4-naphthoquinone to triphthaloylbenzene with pyridine, Berichte der Deutschen Chemischen Gesellschaft [Abteilung] B", Abhandlungen, 1938, 71B, pp. 2569-2583.

Radulescu et al., "Spirans. XXIV. Ring additions in dispirans with 1,3-indandione groups; a new highly condensed aromatic hydrocarbon, benzonaphthanthracene", Bul. Chim., Soc. Chim. Romania [2], 1, pp. 7-17 (1939). English Abstract, CAplus Accession No. 1943:25230, DN 37:25230.

Laatsch, Hartmut, Dimeric naphthoquinones, XIV, "Intermediates of the cyclotrimerization of naphthoquinone: synthesis of hydroxyhepta[2.2.2]starphenequinones", Liebigs Annalen der Chemie, (3), pp. 605-619 (1985).

Klemm, L. H. et al., "The insertion and extrusion of heterosulfur bridges. XIV. Synthesis of nitrotriphenyleno[1,12-bcd]thiophenes", *Journal of Heterocyclic Chemistry*, vol. 24(6), pp. 1749-1755 (1987).

Klemm, L. H. et al., "Chemistry of condensed thiophenes. III. Acetylation of Triphenyleno[1,12-bcd]thiophene[1]", Journal of Heterocyclic Chemistry, vol. 26(5), pp. 1241-1243 (1989).

Ashe, Arthur J., III et al., Selective functionalization in the Bay Region of Polycyclic Aromatic Hydrocarbons via Dilithiation, Journal of Organic Chemistry, vol. 55(21), pp. 5558-5559 (1990).

Jacob, Juergen et al., Rat liver microsomal ring- and S-oxidation of thiaarenes with central of peripheral thiophene rings, *Toxicology*, vol. 68(2), pp. 181-194 (1991).

(56) References Cited

OTHER PUBLICATIONS

Kimura, Takeshi et al., "Photochemical synthesis and electrochemical behavior oftriphenyleno[4, 5-bcd]thiophene and triphenyleno[4,5-bcd]selenophene derivatives", Heterocycles, vol. 35(1), pp. 53-56 (1993).
Thuss, Uwe et al., "Identification and quantification of thiaarenes in the flu gas oflignite-fired domestic heating", Journal of High Resolution Chromatography, vol. 23(7/8), pp. 457-473 (2000).
Winkler, J. K. Karow, W.; Rademacher, P., "Gas phase pyrolysis of heterocyclic compounds, part 4:flow pyrolysis and annulation reactions of some oxygen heterocycles: furan, benzo[b]furan and dibenzofuran, A product oriented study", Journal of Analytical and Applied Pyrolysis, vol. 57(1), pp. 133-144 (2001).
Saito, Masaichi et al., "Arching a bay area of triphenyleno[1,12-bcd]thiophene with group 14 functionalities: Synthesis of the first triphenylene derivatives having thiophene and metallafluorene moieties", Journal of Organometallic Chemistry, vol. 695(7), pp. 1035-1041 (2010).
English Translation of Japanese Office Action dated Jun. 30, 2015 for Japanese Application No. 2013-533106.
Boden, N., et al., "The Synthesis of Triphenylene-Based Discotic Mesogens New and Improved Routes", Liquid Crystals, vol. 33, Nos. 11-12, (2006), pp. 1443-1448.
Heaney, H., et al., "Triphenylene", Organic Systems, Coll. vol. 5, (1973), p. 1120; vol. 40, (1960), p. 105.
Barbera, Joaquin, et al., "Sugar-Coated Discotic Liquid Crystals", Adv. Mater., vol. 13, No. 3, (2001), pp. 175-180.
International Search Report for PCT/EP2011/004654 dated Mar. 22, 2012.
English Translation of Chinese Office Action for Chinese Application No. 201610674734.7, dated Aug. 24, 2017.

\* cited by examiner

TRIPHENYLENE-BASED MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2011/004654, filed Sep. 16, 2011, which claims benefit of German application 10 2010 048 608.6, filed Oct. 15, 2010 which are both incorporated by reference.

The present invention relates to materials for use in electronic devices, in particular in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantummechanical reasons, an up to four-fold energy and power efficiency is possible using organometallic compounds as phosphorescent emitters. In general, there is still a need for improvement, for example with respect to efficiency, operating voltage and lifetime, in the case of OLEDs, in particular also in the case of OLEDs which exhibit triplet emission (phosphorescence). This applies, in particular, to OLEDs which emit in the relatively short-wave region, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in the case of these materials for fluorescent OLEDs.

In accordance with the prior art, triphenylene derivatives are used as matrix materials for phosphorescent emitters, for example in accordance with JP 2005/071983 or WO 2006/038709. However, there is also a need for improvement on use of these matrix materials, in particular with respect to the efficiency and lifetime of the device.

The object of the present invention is the provision of compounds which are suitable for use in a fluorescent or phosphorescent OLED, in particular a phosphorescent OLED, for example as matrix material and/or as holetransport/electron-blocking material or exciton-blocking material and/or as electron-transport or hole-blocking material. In particular, it is the object of the present invention to provide matrix materials which are suitable for green- and red-phosphorescent OLEDs.

Surprisingly, it has been found that triphenylene derivatives which are substituted in positions 1 and 12 by aromatic or heteroaromatic ring systems, carbonyl groups or phosphine oxide groups or in which positions 1 and 12 are bridged by a group selected from in each case optionally substituted boron, carbon, silicon, germanium, tin, nitrogen, oxygen, sulfur or phosphorus achieve this object and result in improvements in the organic electroluminescent device, in particular with respect to the lifetime, efficiency and operating voltage. This applies, in particular, to red- and green-phosphorescent electroluminescent devices, especially on use of the compounds according to the invention as matrix material. The materials according to the invention can be synthesised in few steps and in high yield. The present invention therefore relates to these materials and to organic electroluminescent devices which comprise compounds of this type.

For clarity, the numbering of triphenylene is depicted below:

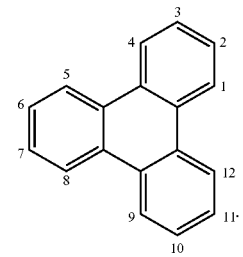

The present invention therefore relates to a neutral compound of the following formula (1) or formula (2),

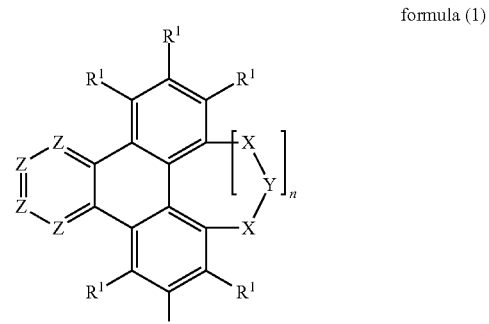

formula (1)

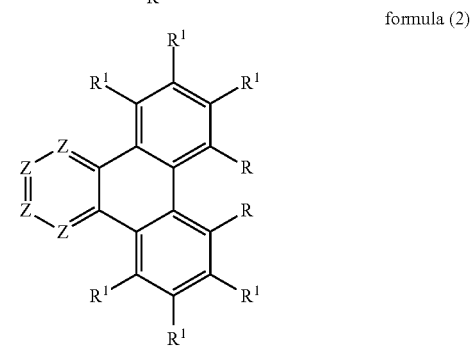

formula (2)

where the following applies to the symbols and indices used:

X is on each occurrence, identically or differently, preferably identically, $BR^2$, $C(R^2)_2$, $C=O$, $Si(R^2)_2$, $Ge(R^2)_2$, $Sn(R^2)_2$, $NR^2$, O, S, SO, $SO_2$, $PR^2$ or $P(=O)R^2$, or X is, for n=0, a group of the following formula (3),

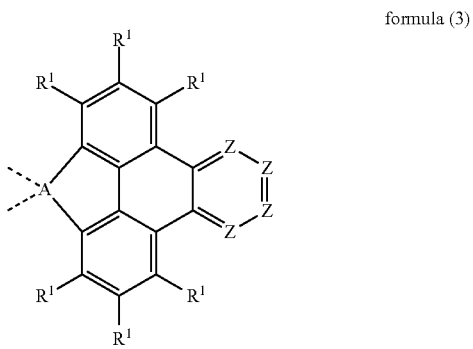

formula (3)

A is C, Si, Ge or Sn; the dashed bonds on A here indicate the bonding to the triphenylene;

Y is BR², O, S, NR², PR² or P(=O)R²;

Z is on each occurrence, identically or differently, CR¹ or N, with the proviso that a maximum of two groups Z per ring stand for N;

R is selected on each occurrence, identically or differently, from the group consisting of N(Ar¹)₂, C(=O)Ar¹, P(=O)(Ar¹)₂ and an aromatic or heteroaromatic ring system having 5 to 60 aromatic ring atoms, which may in each case be substituted by one or more radicals R¹;

Ar¹ is on each occurrence, identically or differently, an aromatic or heteroaromatic ring system having 5 to 60 aromatic ring atoms, which may be substituted by one or more non-aromatic radicals R³; two radicals Ar¹ here which are bonded to the same N atom or P atom may also be bridged to one another by a single bond or a bridge selected from N(R⁴), C(R⁴)₂, O or S, R¹ is selected on each occurrence, identically or differently, from the group consisting of H, D, F, Cl, Br, I, CN, NO₂, N(Ar¹)₂, N(R³)₂, C(=O)Ar¹, C(=O)R³, P(=O)(Ar¹)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the alkyl, alkoxy, thioalkoxy, alkenyl or alkynyl group may in each case be substituted by one or more radicals R³ and where one or more non-adjacent CH₂ groups may be replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, CN or NO₂, an aromatic or heteroaromatic ring system having 5 to 60 aromatic ring atoms, which may in each case be substituted by one or more radicals R³, an aryloxy or heteroaryloxy group having 5 to 60 aromatic ring atoms, which may be substituted by one or more radicals R³, or a combination of these systems, where two or more adjacent substituents R¹ which are bonded to the same benzene ring may optionally form a monocyclic or polycyclic, aliphatic, aromatic or heteroaromatic ring system;

R² is selected on each occurrence, identically or differently, from the group consisting of a straight-chain alkyl group having 1 to 20 C atoms or a branched or cyclic alkyl group having 3 to 20 C atoms, each of which may be substituted by one or more radicals R³, where one or more non-adjacent CH₂ groups may be replaced by R³C=CR³, C≡C, Si(R³)₂, C=O, C=NR³, P(=O)(R³), SO, SO₂, NR³, O, S or CONR³ and where one or more H atoms may be replaced by D, F, Cl, Br, I, CN or NO₂, or an aromatic or heteroaromatic ring system having 5 to 60 aromatic ring atoms, which may in each case be substituted by one or more radicals R³, where two substituents R² which are bonded to the same carbon, silicon, germanium or tin atom may optionally form a monocyclic or polycyclic, aliphatic, aromatic or heteroaromatic ring system with one another, which may be substituted by one or more radicals R³;

R³ is selected on each occurrence, identically or differently, from the group consisting of H, D, F, Cl, Br, I, CN, NO₂, N(R⁴)₂, C(=O)Ar¹, C(=O)R⁴, P(=O)(Ar¹)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the alkyl, alkoxy, thioalkyl, alkenyl or alkynyl group may be substituted by one or more radicals R⁴ and where one or more non-adjacent CH₂ groups may be replaced by R⁴C=CR⁴, C≡C, Si(R⁴)₂, C=O, C=NR⁴, P(=O)(R⁴), SO, SO₂, NR⁴, O, S or CONR⁴ and where one or more H atoms may be replaced by D, F, Cl, Br, I, CN or NO₂, an aromatic or heteroaromatic ring system having 5 to 60 aromatic ring atoms, which may in each case be substituted by one or more radicals R⁴, an aryloxy or heteroaryloxy group having 5 to 60 aromatic ring atoms, which may be substituted by one or more radicals R⁴, or a combination of these systems, where two or more adjacent substituents R³ may optionally form a monocyclic or polycyclic, aliphatic, aromatic or heteroaromatic ring system, which may be substituted by one or more radicals R⁴;

R⁴ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I, CN or an alkyl group having 1 to 5-C atoms, where two or more adjacent substituents R⁴ may form a mono- or polycyclic, aliphatic, aromatic or heteroaromatic ring system with one another;

n is 0 or 1;

with the proviso that at least one group R¹ in formula (1) stands for an aromatic or heteroaromatic ring system if X stands for C=O, O, S, SO or SO₂ and n=0;

and furthermore with the proviso that the following compounds are excluded from the invention:

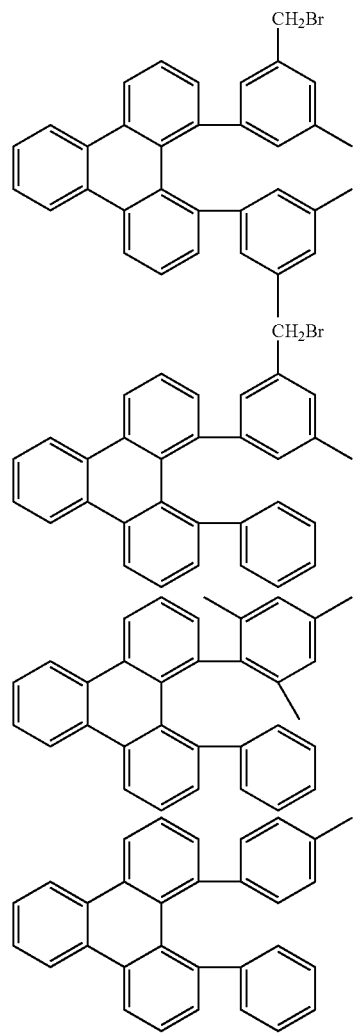

-continued

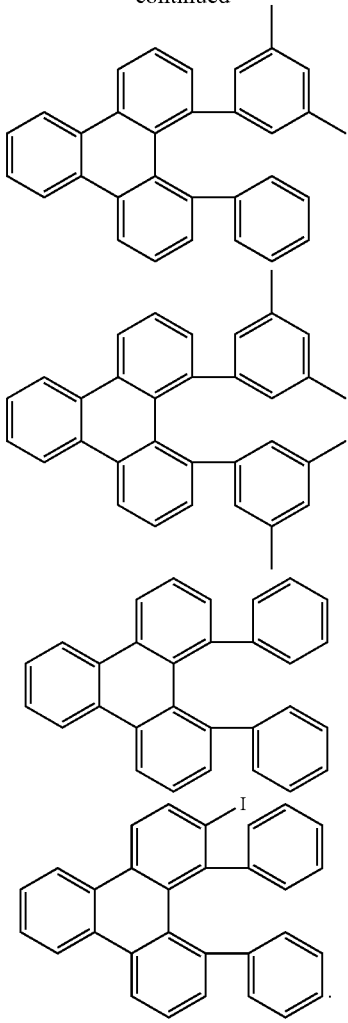

A "non-aromatic radical" $R^3$, as mentioned in the definition of $Ar^1$, is a radical in accordance with the definition of $R^3$ which contains no aromatic or heteroaromatic groups, i.e., for example, also no aromatic carbonyl group.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl or bipyridine, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N, O or Si atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by an alkyl group having one to five C atoms or a carbonyl group.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptynylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5 to 60 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, a maximum of one group Z per ring stands for N and the other groups Z stand, identically or differently on each occurrence, for $CR^1$. In a particularly preferred embodiment of the invention, all groups Z stand, identically or differently on each occurrence, for $CR^1$.

Preferred embodiments of the compounds of the formula (1) and (2) are therefore the compounds of the following formulae (4) to (7), formula (4)

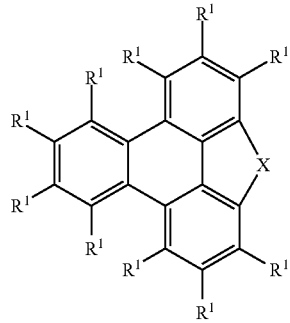

formula (5)

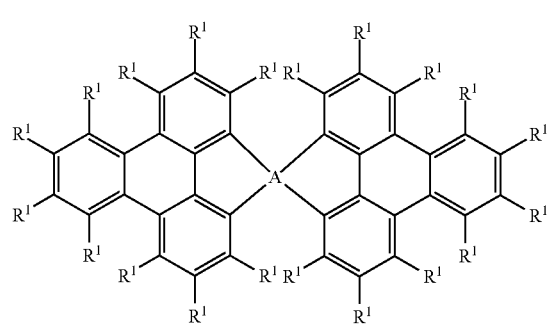

formula (6)

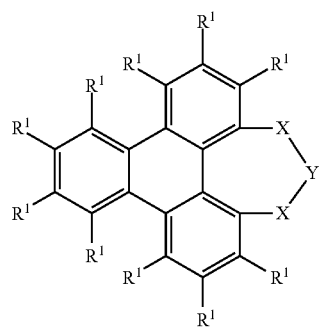

formula (7)

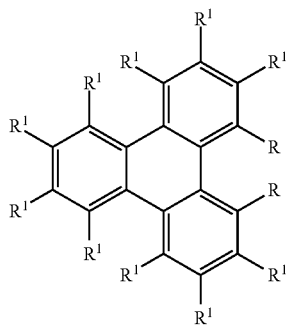

where the symbols used have the meanings given above. X in formula (4) and (6) cannot be a group of the formula (3).

Preferred embodiments of the compounds of the formulae (4) to (7) are the compounds of the following formulae (4a) to (7a), formula (4a)

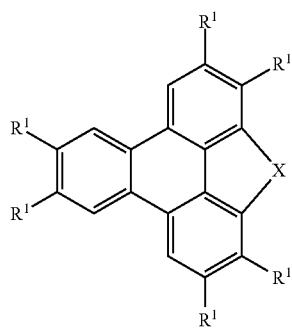

formula (5a)

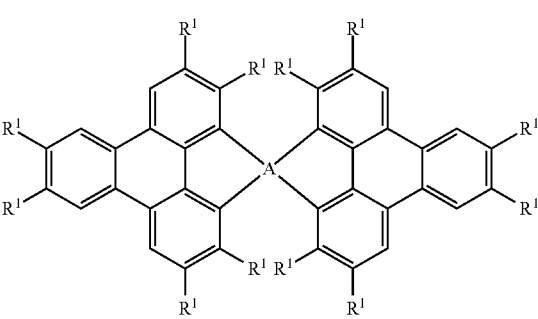

formula (6a)

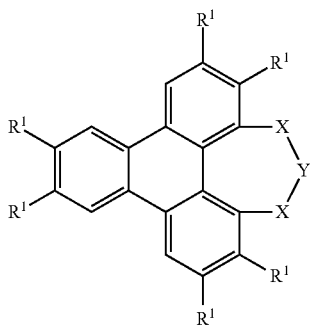

-continued

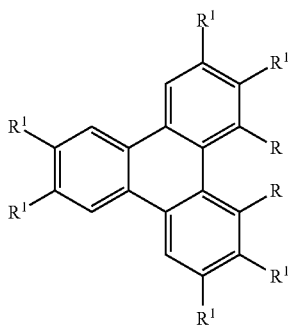

formula (7a)

where the symbols used have the meanings given above.

In compounds of the formula (1) where n=0 or formula (4) or formula (4a), X is preferably selected from the group consisting of $C(R^2)_2$, $Si(R^2)_2$ and $N(R^2)$, particularly preferably $N(R^2)$.

$R^2$ preferably stands, identically or differently on each occurrence, for an aromatic or heteroaromatic ring system having 5 to 40 aromatic ring atoms, preferably having 5 to 24 aromatic ring atoms, which may in each case also be substituted by one or more radicals $R^3$ and where two radicals $R^2$ which are bonded to the same carbon, silicon, germanium or tin atom may also form an aromatic ring system with one another and may thus form a spiro system. Particularly preferred aromatic or heteroaromatic ring systems $R^2$ are shown below together with the preferred groups for $R^1$.

In a preferred embodiment of the compounds of the formula (1) in which X stands for a group of the formula (3), or formula (5) or formula (5a), the two triphenylene moieties which are bonded to A are in each case substituted identically. In these compounds, A furthermore preferably stands for carbon or silicon, particularly preferably for carbon.

In compounds of the formula (1) where n=1 or formula (6) or formula (6a), the group X—Y—X is preferably selected from the group consisting of $C(R^2)_2$—O—$C(R^2)_2$, $Si(R^2)_2$—O—$Si(R^2)_2$, O—$BR^2$—O, O—$PR^2$—O, O—P(=O)$R^2$—O and C(=O)—$NR^2$—C(=O).

In a preferred embodiment of the compounds of the formula (2) or formula (7) or formula (7a), the two radicals R are selected identically.

In a preferred embodiment of the invention, $R^1$ in the formulae given above is selected, identically or differently on each occurrence, from the group consisting of H, D, F, Cl, Br, CN, $N(Ar^1)_2$, $C(=O)Ar^1$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals $R^3$, where one or more non-adjacent $CH_2$ groups may be replaced by O and where one or more H atoms may be replaced by D or F, or an aromatic or heteroaromatic ring system having 5 to 30 aromatic ring atoms, which may in each case be substituted by one or more radicals $R^3$.

In a particularly preferred embodiment of the invention, $R^1$ in the formulae given above is selected, identically or differently on each occurrence, from the group consisting of H, D, F, CN, a straight-chain alkyl group having 1 to 10 C atoms or a branched or cyclic alkyl group having 3 to 10 C atoms, each of which may be substituted by one or more radicals $R^3$, where one or more H atoms may be replaced by D or F, or an aromatic or heteroaromatic ring system having 5 to 18 aromatic ring atoms, which may in each case be substituted by one or more radicals $R^3$.

In a further embodiment of the invention, the radicals $R^1$ which are bonded directly to the triphenylene are equal to H.

For compounds which are processed by vacuum evaporation, the alkyl groups preferably have not more than four C atoms, particularly preferably not more than 1 C atom. For compounds which are processed from solution, compounds which are substituted by alkyl groups having up to 10 C atoms or which are substituted by oligoarylene groups, for example ortho-, meta-, para- or branched terphenyl groups or quaterphenyl groups, are also suitable.

Depending on the use of the compounds according to the invention, different substituents R and $R^1$ are selected.

If the compounds of the formulae (1) or (2) or (4) to (7) or (4a) to (7a) are used as matrix material for phosphorescent emitters, at least one radical $R^1$ preferably stands for $N(Ar^1)_2$, $C(=O)Ar^1$, $P(=O)(Ar^1)_2$ or for an aromatic or heteroaromatic ring system having 5 to 60 aromatic ring atoms, which may be substituted by one or more radicals $R^3$, where the group $Ar^1$ or the radicals on $Ar^1$ or the aromatic or heteroaromatic ring system or the radicals $R^3$ on the aromatic or heteroaromatic ring system contain no condensed aryl groups having more than 10 C atoms and no condensed heteroaryl groups in which more than two aryl or 6-membered heteroaryl groups are condensed directly onto one another.

In a particularly preferred embodiment of the invention, $Ar^1$ or the radicals on $Ar^1$ or the aromatic or heteroaromatic ring system or the radicals $R^3$ on the aromatic or heteroaromatic ring system contain no condensed aryl groups and no condensed heteroaryl groups in which two or more aryl or 6-membered heteroaryl groups are condensed directly onto one another.

Particularly preferred groups $Ar^1$ are selected from the group consisting of phenyl, ortho-, meta- or para-biphenyl, ortho-, meta- or para-terphenyl, ortho-, meta-, para- or branched quaterphenyl, fluorene or spirobifluorene, each of which may be substituted by one or more non-aromatic radicals $R^3$, but are preferably unsubstituted.

Particularly preferred aromatic ring systems $R^1$ and $R^2$ are selected from the group consisting of phenyl, ortho-, meta- or para-biphenyl, ortho-, meta- or para-terphenyl, ortho-, meta-, para- or branched quaterphenyl, fluorene or spirobifluorene, each of which may be substituted by one or more radicals $R^3$, but are preferably unsubstituted.

Particularly preferred heteroaromatic ring systems $R^1$ and $R^2$ contain, as heteroaryl group, triazine, pyrimidine, pyrazine, pyridazine, pyridine, benzothiophene, benzofuran, indole, carbazole, azacarbazole, diazacarbazole, dibenzothiophene and/or dibenzofuran. The heteroaromatic ring systems here are, in particular, selected from the structures of the following formulae (8) to (38),

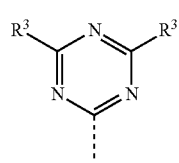

formula (8)

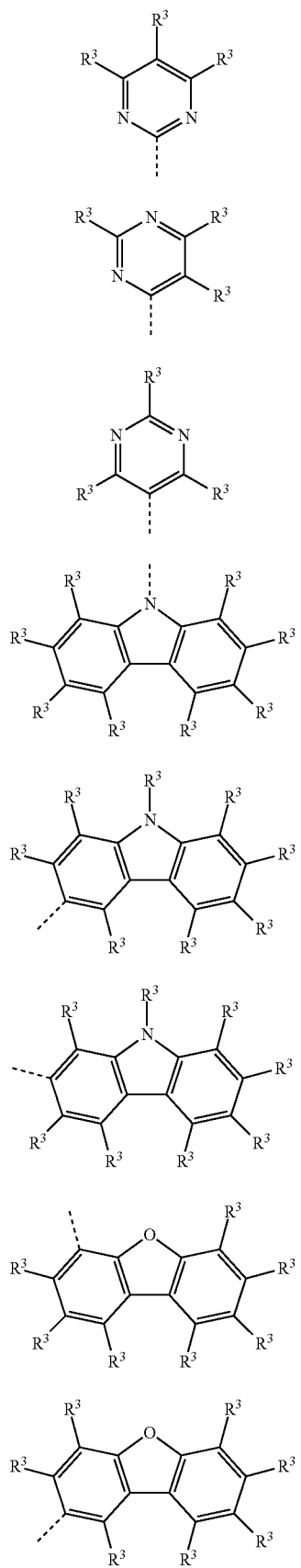
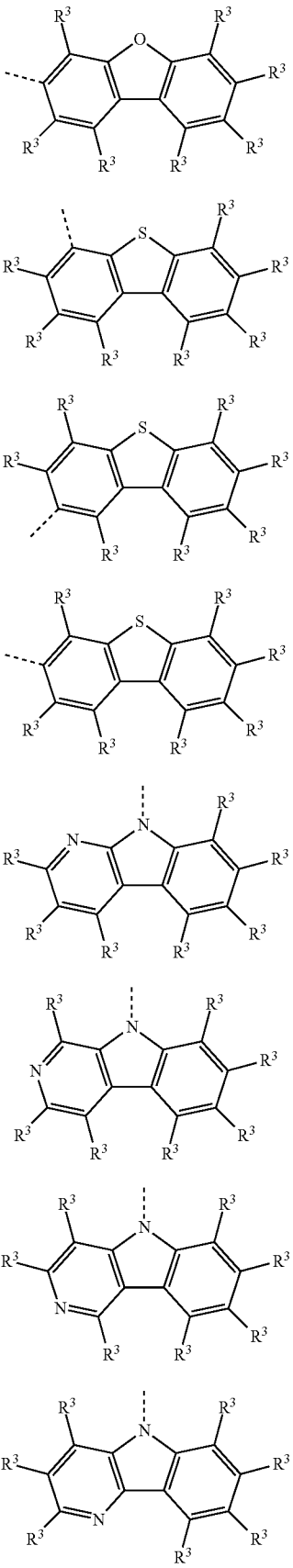

formula (25)
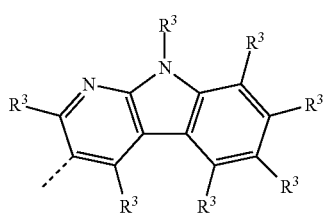
formula (26)
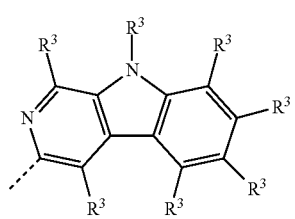
formula (27)
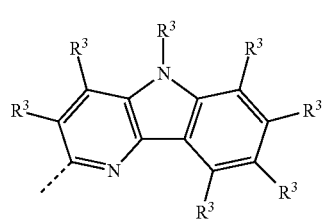
formula (28)
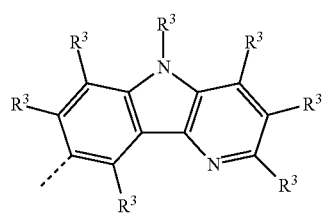
formula (29)
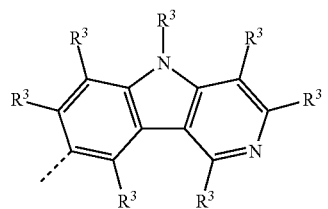
formula (30)
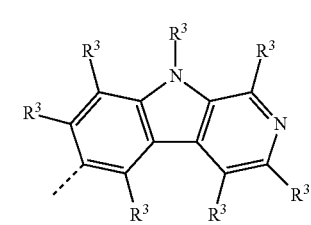
formula (31)
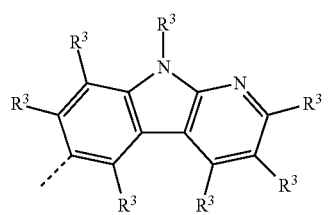
formula (32)
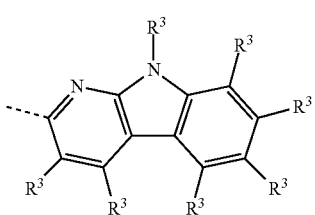
formula (33)
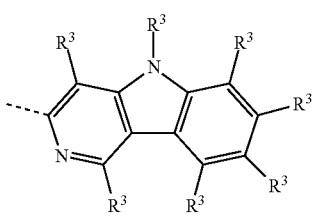
formula (34)
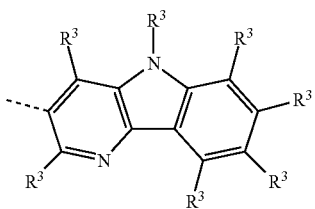
formula (35)
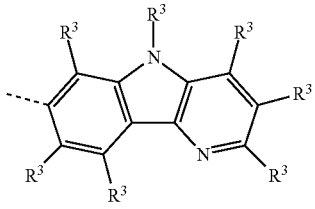
formula (36)
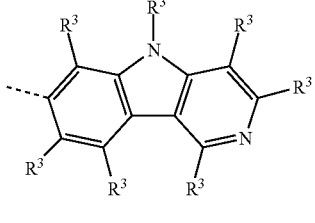
formula (37)
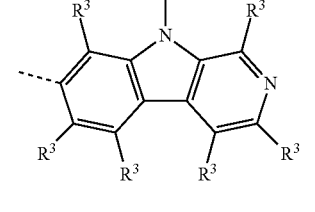
formula (38)
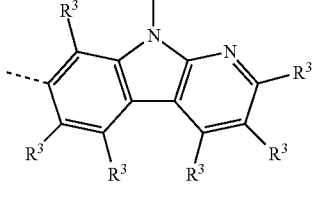
where $R^3$ has the meanings given above and the dashed bond represents the bond to the triphenylene skeleton or to X.

Preferred embodiments of the groups of the formulae (8) to (38) are the structures of the following formulae (8a) to (38a),
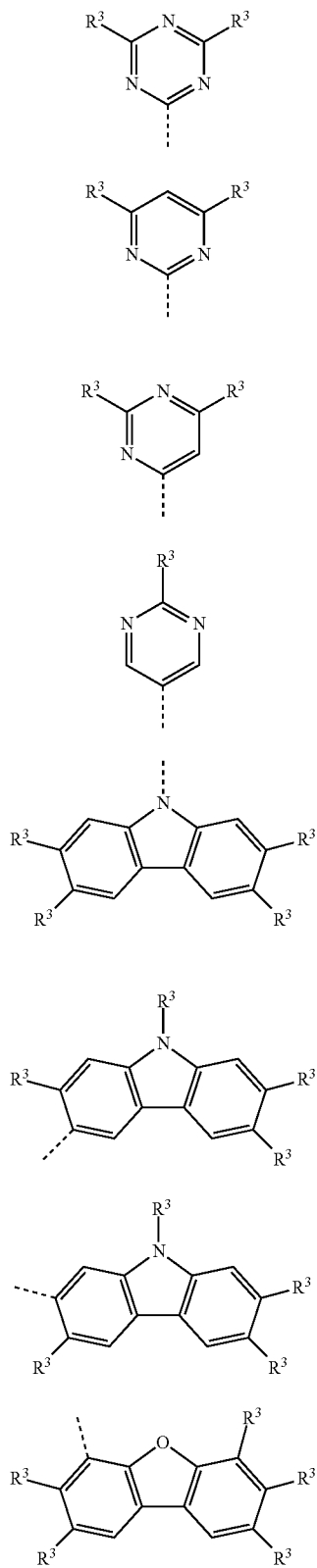
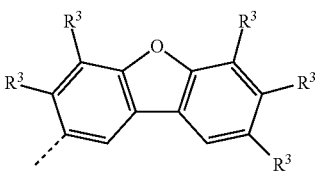
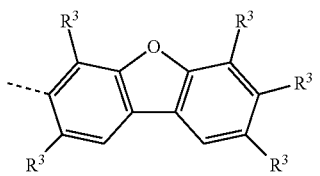
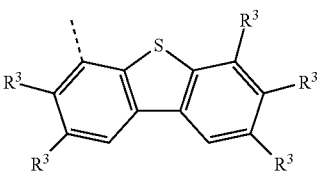
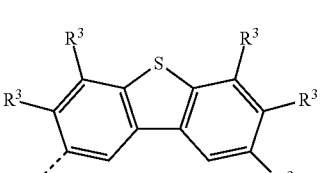
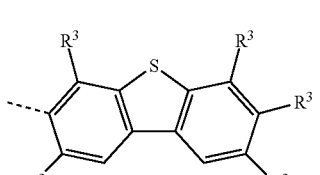
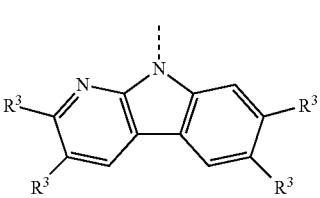
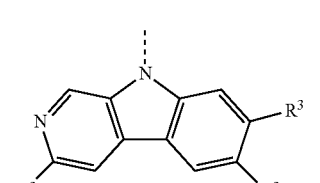
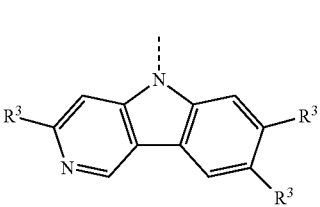

formula (24a)
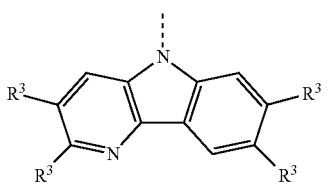

formula (25a)
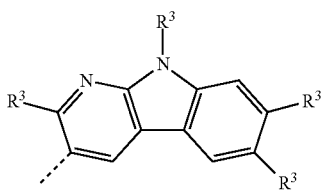

formula (26a)
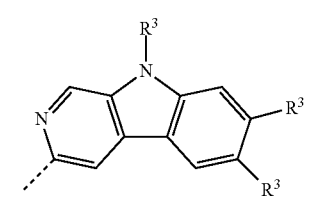

formula (27a)
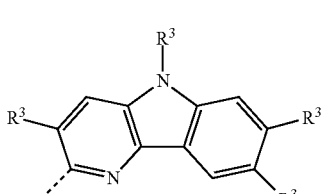

formula (28a)
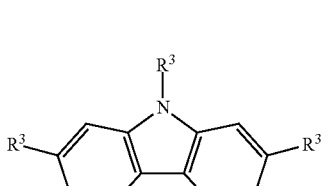

formula (29a)
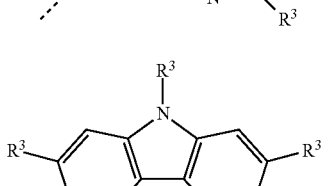

formula (30a)
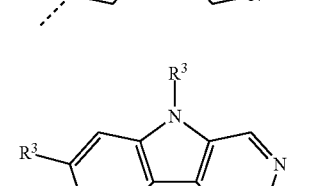

formula (31a)
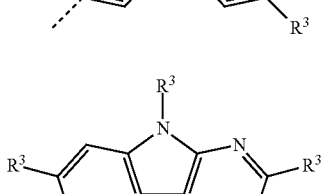

formula (32a)
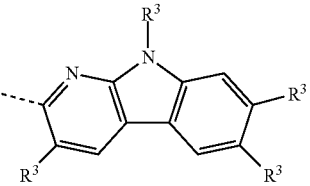

formula (33a)
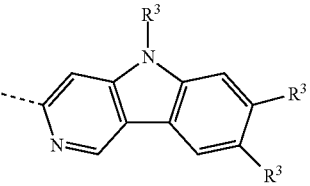

formula (34a)
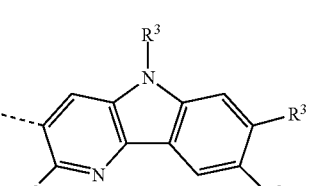

formula (35a)
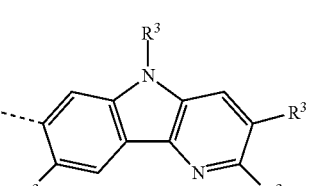

formula (36a)
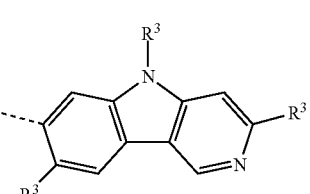

formula (37a)
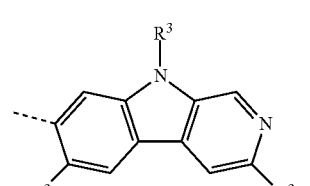

formula (38a)
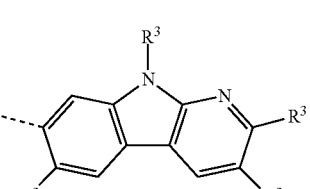

where $R^3$ has the meanings given above and the dashed bond represents the bond to the triphenylene skeleton or to X. $R^3$ in formula (8a) preferably stands, identically or differently, for an aromatic or heteroaromatic ring system having 5 to 24 aromatic ring atoms, in particular, identically or differently, for phenyl, biphenyl, terphenyl or quaterphenyl.

If $R^1$ or R stands for a group $N(Ar^1)_2$, this group is then preferably selected from the structures of the following formula (39) or (41), and if $R^1$ or $R^2$ or R stands for an aromatic or heteroaromatic ring system which is a triarylamine or triheteroarylamine group, this group is then preferably selected from the structures of the following formula (40),

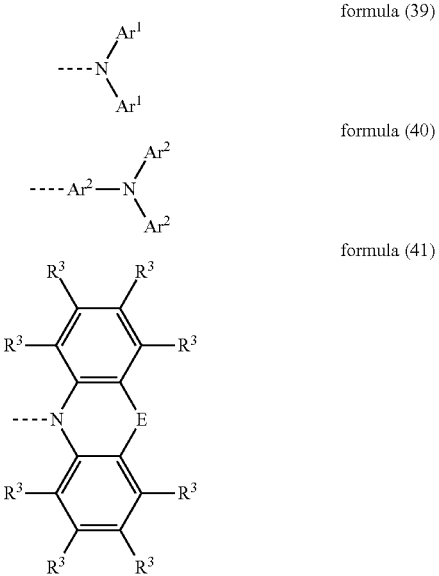

formula (39)

formula (40)

formula (41)

where the symbols used have the meanings given above, the dashed bond represents the bond to the triphenylene skeleton or in formula (40) also to X and furthermore:

$Ar^2$ is, identically or differently on each occurrence, an aromatic or heteroaromatic ring system having 5 to 24 aromatic ring atoms, which may be substituted by one or more radicals $R^3$; the sum of the aromatic ring atoms of all groups $Ar^2$ together is not greater than 60 here;

E is selected from the group consisting of $C(R^4)_2$, $NR^4$, O or S.

$Ar^1$ in formula (39) and $Ar^2$ in formula (40) preferably stands, identically or differently on each occurrence, for phenyl, 1- or 2-naphthyl, ortho-, meta- or para-biphenyl, ortho-, meta-, para- or branched terphenyl, ortho-, meta-, para- or branched quaterphenyl, 2-fluorenyl or 2-spirobifluorenyl, each of which may be substituted by one or more radicals $R^3$.

If the compound of the formula (2) or (7) or (7a) is used as matrix material for phosphorescent emitters, R furthermore preferably stands, identically or differently on each occurrence, for $N(Ar^1)_2$, $C(=O)Ar^1$, $P(=O)(Ar^1)_2$ or an aromatic or heteroaromatic ring system having 5 to 60 aromatic ring atoms, which may be substituted by one or more radicals $R^1$, where the group $Ar^1$ or the radicals on $Ar^1$ or the aromatic or heteroaromatic ring system or the radicals $R^1$ on the aromatic or heteroaromatic ring system contains no condensed aryl groups having more than 10 C atoms and no condensed heteroaryl groups in which more than two aryl or 6-membered heteroaryl groups are condensed directly onto one another.

In a particularly preferred embodiment of the invention, $Ar^1$ or the radicals on $Ar^1$ or the aromatic or heteroaromatic ring system or the radicals $R^1$ on the aromatic or heteroaromatic ring system contain no condensed aryl groups and no condensed heteroaryl groups in which two or more aryl or 6-membered heteroaryl groups are condensed directly onto one another.

Very particularly preferred groups $Ar^1$ are selected from the group consisting of phenyl, ortho-, meta- or para-biphenyl, ortho-, meta- or para-terphenyl, ortho-, meta-, para- or branched quaterphenyl, fluorene or spirobifluorene, each of which may be substituted by one or more non-aromatic radicals $R^3$, but is preferably unsubstituted.

Very particularly preferred aromatic or heteroaromatic ring systems R in formula (2) are selected from the group consisting of phenyl, ortho-, meta- or para-biphenyl, ortho-, meta- or para-terphenyl, ortho-, meta-, para- or branched quaterphenyl, fluorene, spirobifluorene, triazine, pyridine, pyrazine, pyrimidine, pyridazine or carbazole, each of which may be substituted by one or more radicals $R^1$, but is preferably unsubstituted.

If the compounds of the formulae (1) or (2) or (4) to (7) or (4a) to (7a) are used as matrix material for a fluorescent emitter, at least one radical $R^1$ and/or at least one radical $R^2$ which is bonded to X and/or at least one radical R in the formulae (2), (7) or (7a) preferably stands for an aromatic or heteroaromatic ring system which contains at least one aryl group having at least three condensed six-membered rings, preferably anthracene. X here preferably stands for $N(R^2)$ or for $C(R^2)_2$.

If the compounds of the formulae (1) or (2) or (4) to (7) or (4a) to (7a) are used as fluorescent emitter, X preferably stands for $N(R^2)$ and $R^2$ stands for an aromatic or heteroaromatic ring system which contains at least one aryl group or an aromatic ring system having at least two condensed six-membered rings, which is preferably bonded directly to the nitrogen of the group X. The condensed aryl group here is preferably selected from anthracene, pyrene, phenanthrene, chrysene, monobenzoindenofluorene or dibenzoindenofluorene.

If the compounds of the formulae (1) or (2) or (4) to (7) or (4a) to (7a) are used as electron-transport material, at least one radical $R^1$ and/or at least one radical R in the formulae (2), (7) or (7a) preferably stands for $C(=O)Ar^1$, $P(=O)(Ar^1)_2$ or for an electron-deficient heteroaromatic ring system having 5 to 40 aromatic ring atoms, preferably having 5 to 25 aromatic ring atoms, which may be substituted by one or more radicals $R^3$; and/or X in compounds of the formula (1) where n=0 preferably stands for $BR^2$, $C=O$, SO, $SO_2$ or $P(=O)(R^2)_2$. An electron-deficient heteroaromatic ring system in the sense of the present invention is a heteroaromatic ring system which contains at least one electron-deficient heteroaryl group, which is either a 6-membered heteroaryl group having at least one nitrogen atom or a 5-membered heteroaryl group having at least two heteroatoms.

Particularly preferred electron-deficient heteroaromatic ring systems $R^1$ contain, as heteroaryl group, at least one group selected from triazine, pyrimidine, pyrazine, pyridazine, pyridine, imidazole, pyrazole, oxazole, oxadiazole, triazole, thiazole, thiadiazole, benzimidazole, quinoline, isoquinoline and quinoxaline. The heteroaromatic ring systems here are, in particular, selected from the structures of the formulae (8) to (11) and (8a) to (11a) given above or from the following formulae (42) to (45),

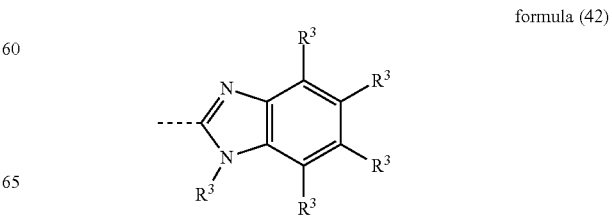

formula (42)

-continued

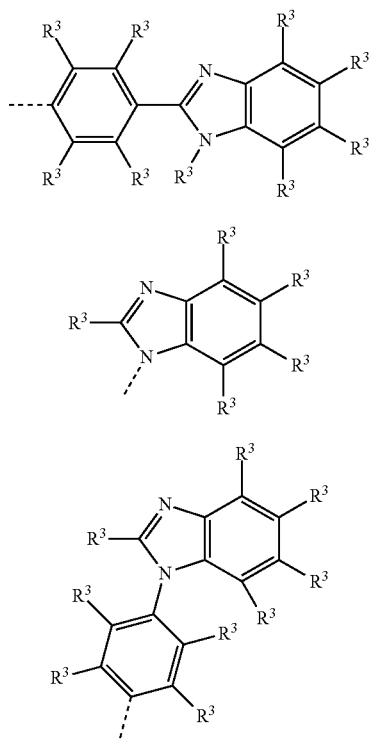

formula (43)

formula (44)

formula (45)

where R³ has the meanings given above and the dashed bond represents the bond to the triphenylene skeleton.

Preferred embodiments of the groups of the formulae (42) to (45) are the structures of the following formulae (42a) to (45a),

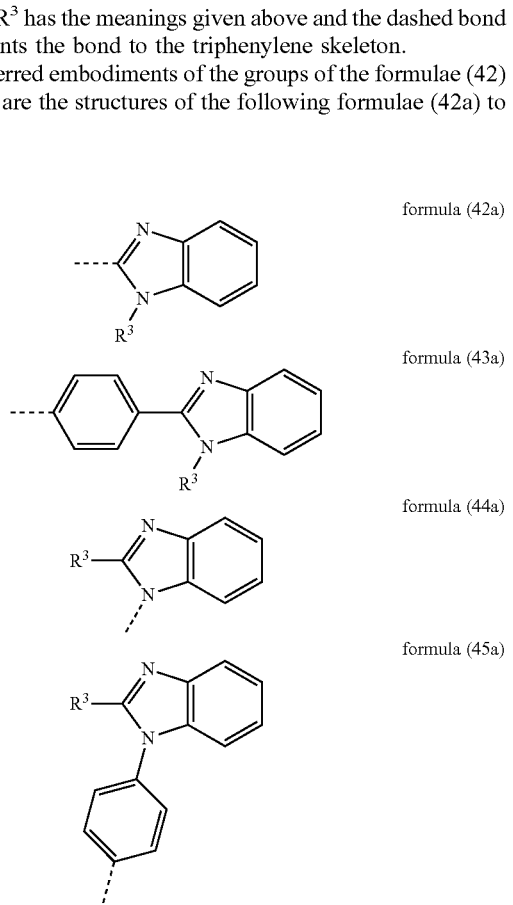

formula (42a)

formula (43a)

formula (44a)

formula (45a)

where R³ has the meanings given above and the dashed bond represents the bond to the triphenylene skeleton. R³ here preferably stands, identically or differently, for an aromatic or heteroaromatic ring system having 5 to 24 aromatic ring atoms, in particular, identically or differently, for phenyl, biphenyl, terphenyl or quaterphenyl.

If the compounds of the formulae (1) or (2) or (4) to (7) or (4a) to (7a) are used as hole-transport material or as emitting compound, at least one radical $R^1$ and/or R preferably stands for $N(Ar^1)_2$, for a triarylamino group or for an electron-rich heteroaromatic ring system having 5 to 40 aromatic ring atoms, in particular 5 to 25 aromatic ring atoms, which may be substituted by one or more radicals $R^3$, in particular for a radical of one of the formulae (39) to (41) given above; and/or X in compounds of the formula (1) where n=0 stands for $NR^2$ or $PR^2$. An electron-rich heteroaromatic ring system in the sense of the present invention is a heteroaromatic ring system which contains at least one electron-rich heteroaryl group, which is a 5-membered heteroaryl group having precisely one heteroatom, onto which, in addition, one or more aryl groups may be condensed.

Particularly preferred electron-rich heteroaromatic ring systems $R^1$ contain, as heteroaryl group, pyrrole, furan, thiophene, benzothiophene, benzofuran, indole, carbazole, dibenzothiophene, dibenzofuran and/or azacarbazole. The electron-rich heteroaromatic ring systems here are, in particular, selected from the structures of the formulae (12) to (38) given above.

In an embodiment of the invention, preferences given above can be combined with one another as desired.

Examples of preferred compounds of the above-mentioned embodiments or compounds as can preferably be employed in electronic devices are the compounds of the following structures (1) to (91).

(1)

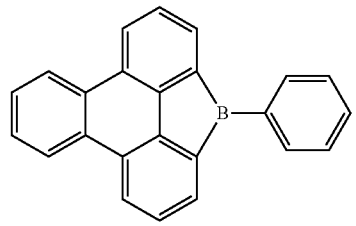

(2)

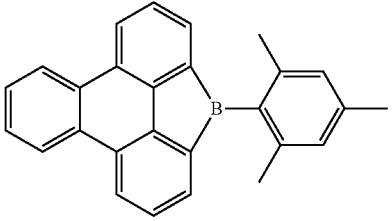

(3)

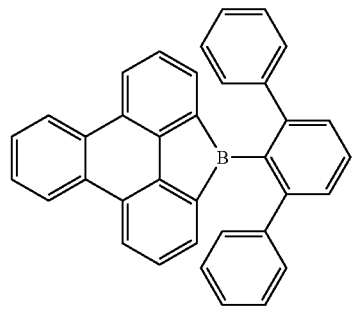

(4)
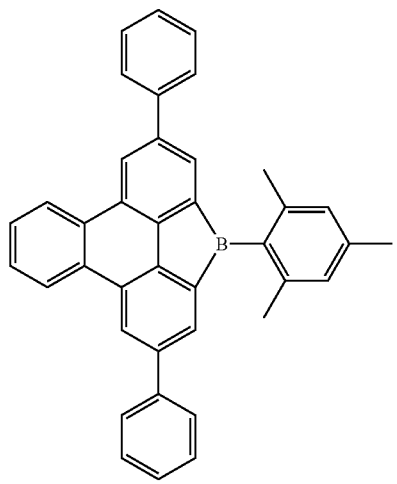
(5)
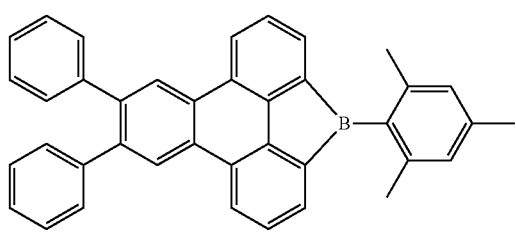
(6)
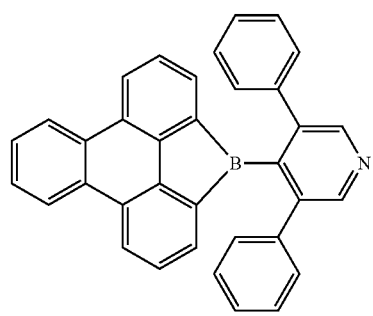
(7)
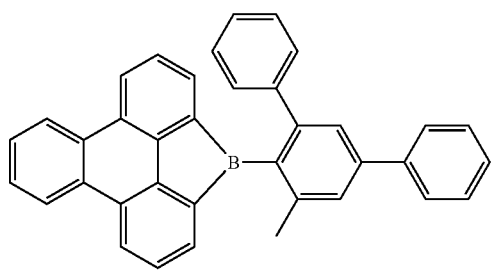
(8)
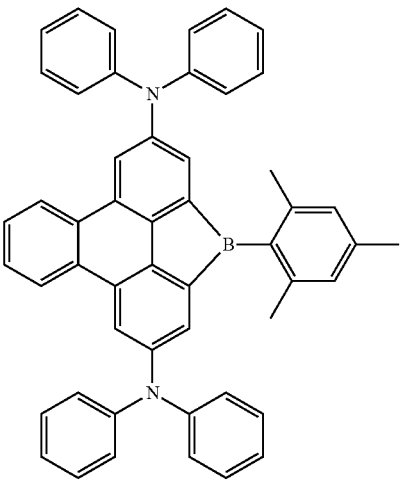
(9)
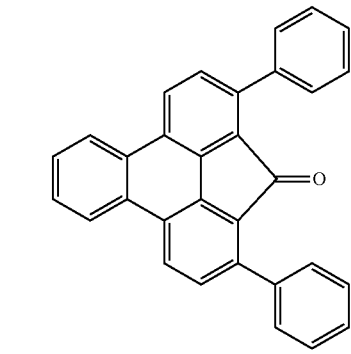
(10)
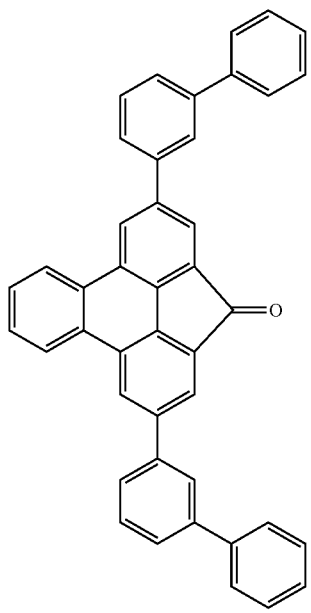

(11)
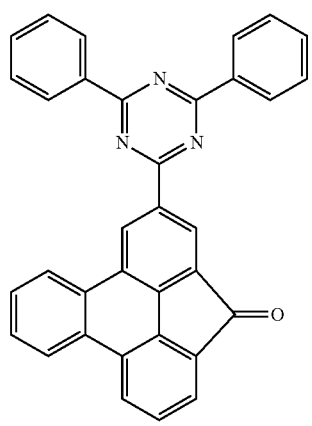
(12)
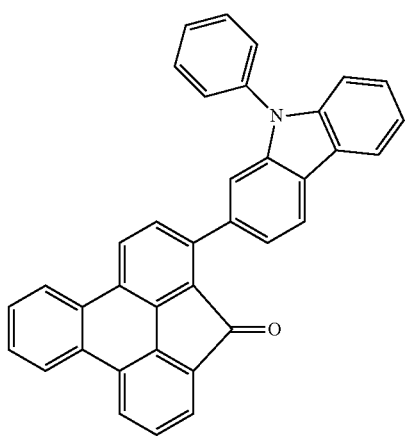
(13)
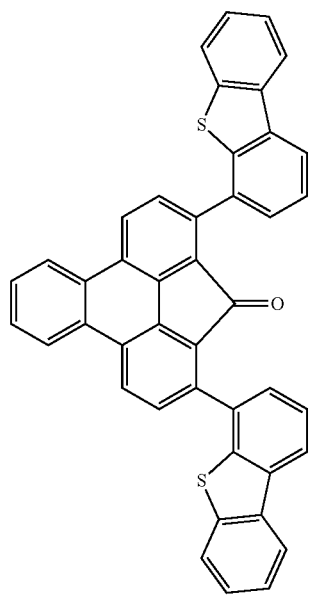
(14)
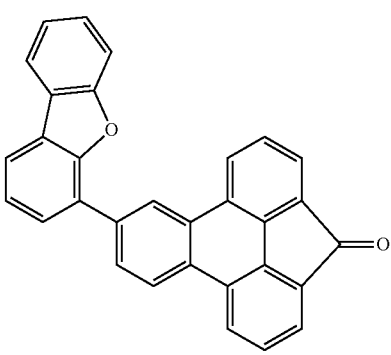
(15)
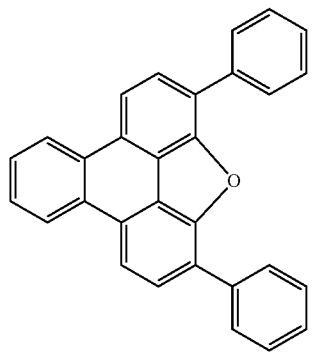
(16)

-continued
(17)
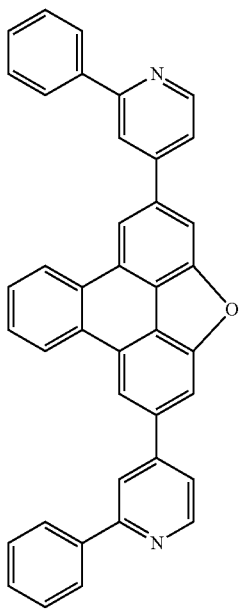
(18)
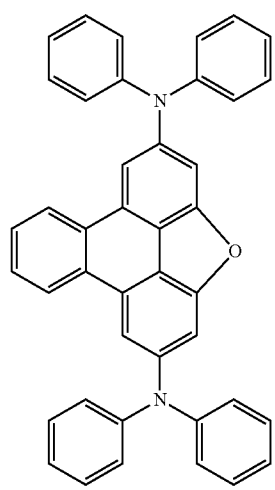
(19)
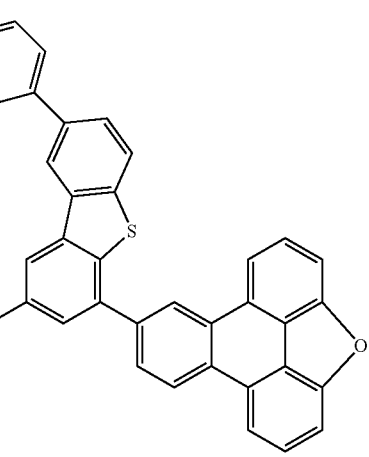
-continued
(20)
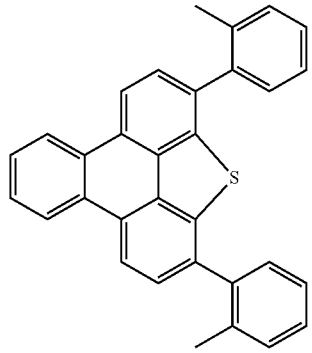
(21)
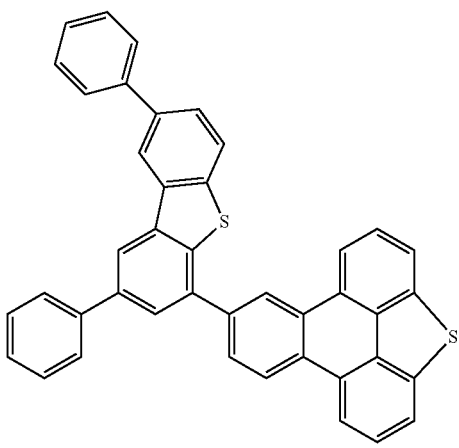
(22)
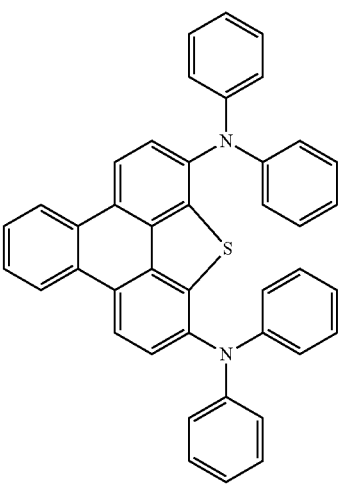

(23)
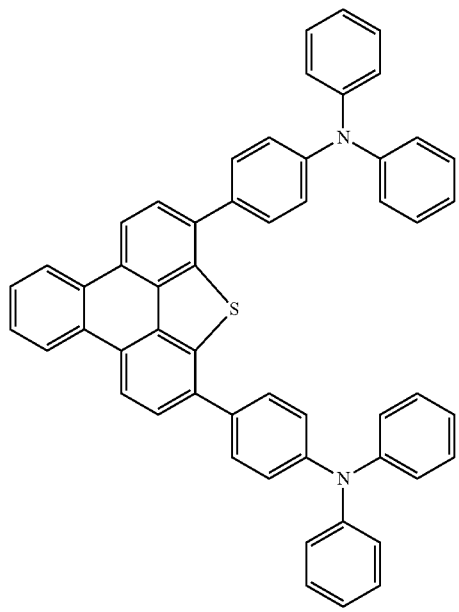
(24)
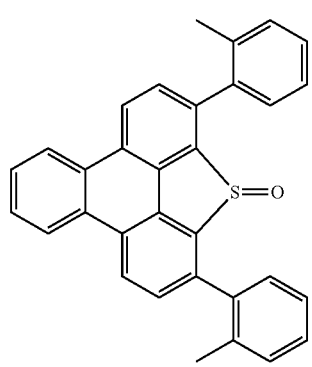
(25)
(26)
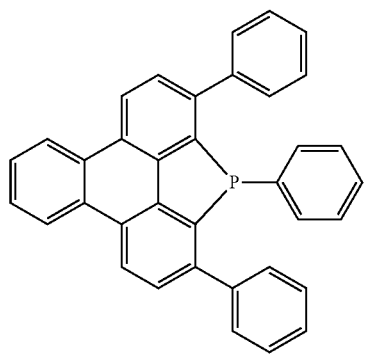
(27)
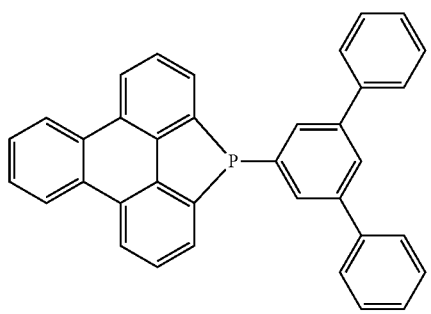
(28)
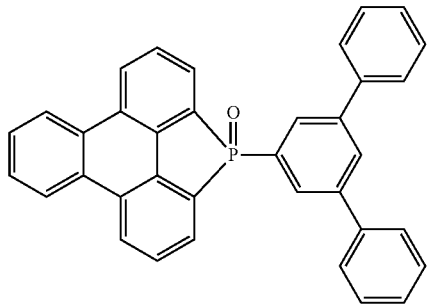
(29)
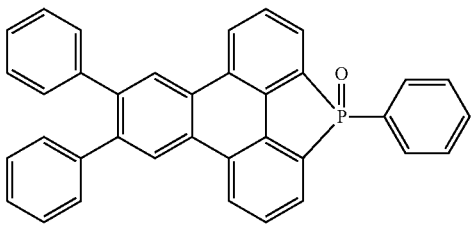
(30)
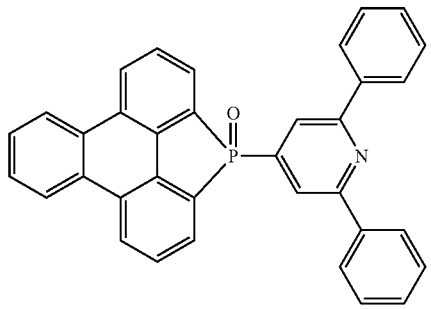

-continued
(31)
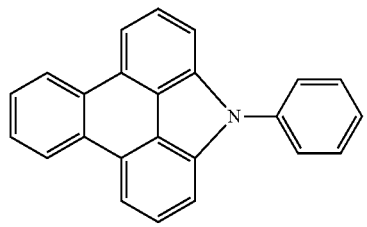
(32)
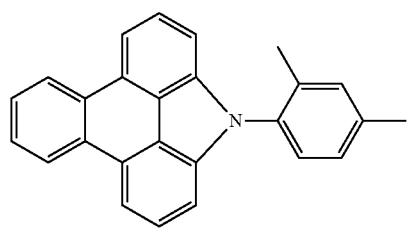
(33)
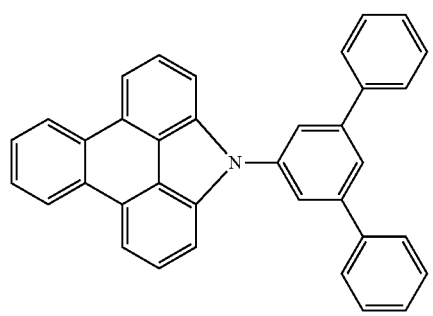
(34)
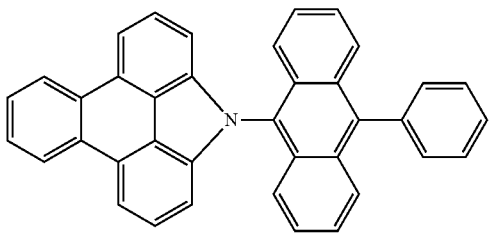
(35)
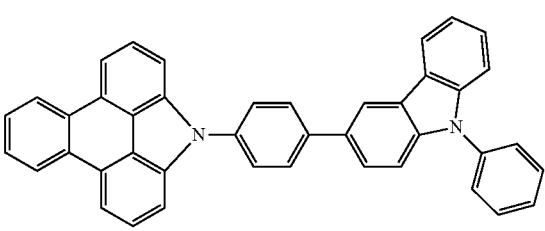
-continued
(36)
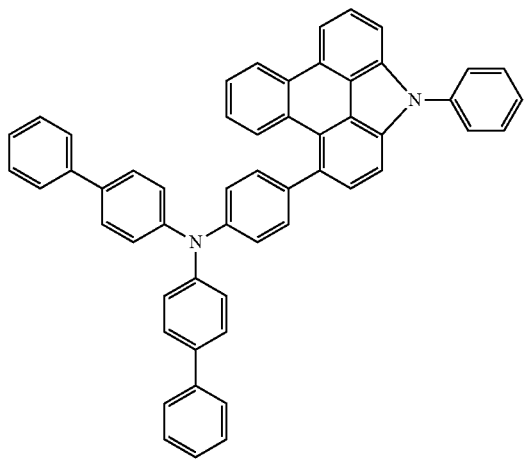
(37)
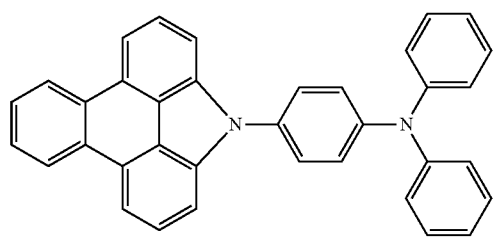
(38)
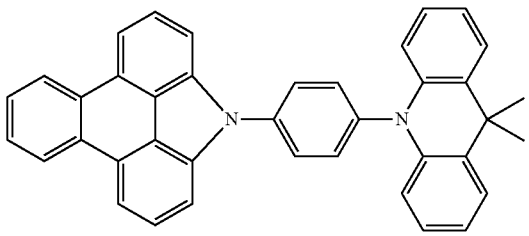
(39)
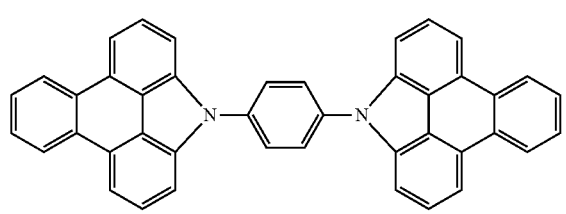
(40)
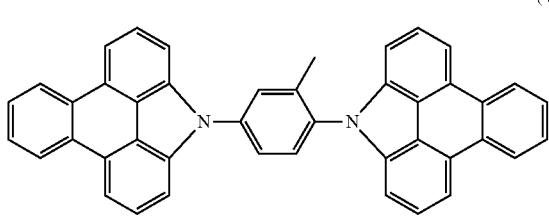

(41)
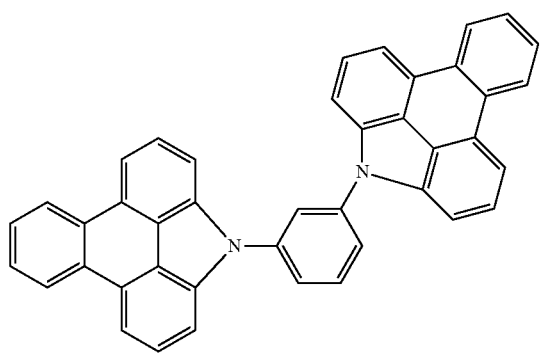
(42)
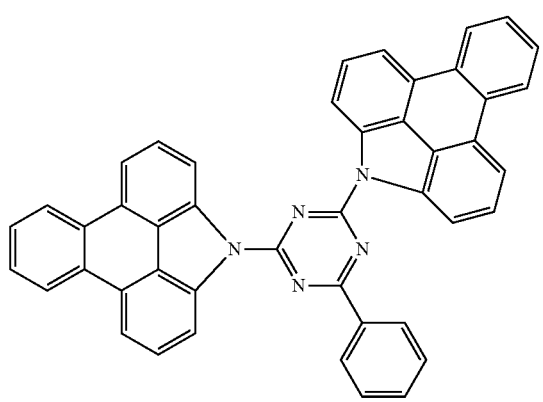
(43)
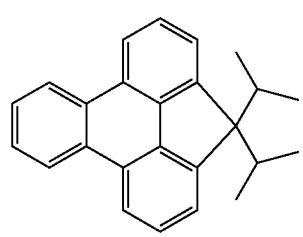
(44)
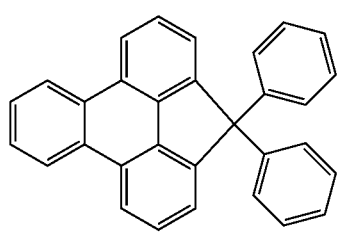
(45)
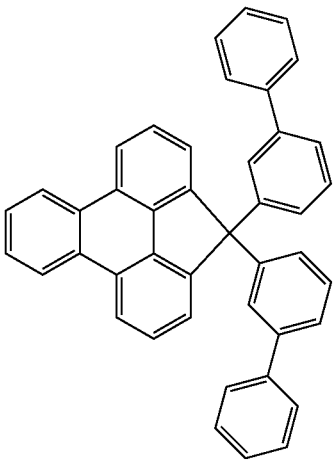
(46)
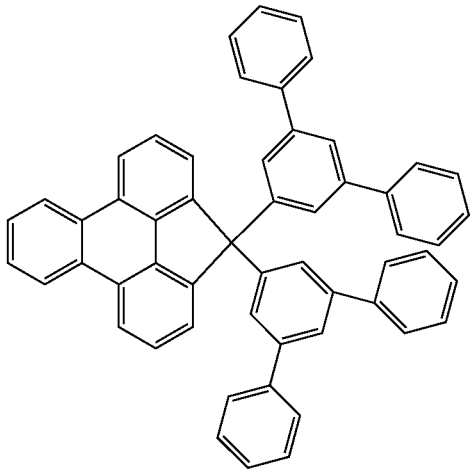
(47)
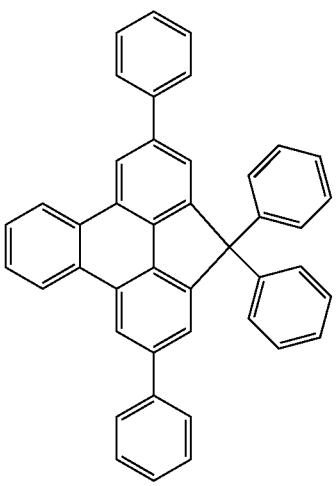
(48)
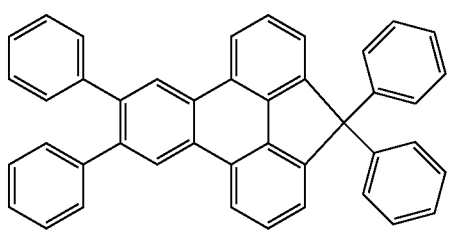

(49)
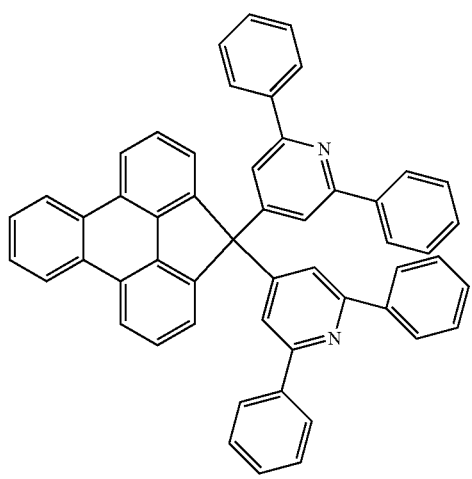
(52)
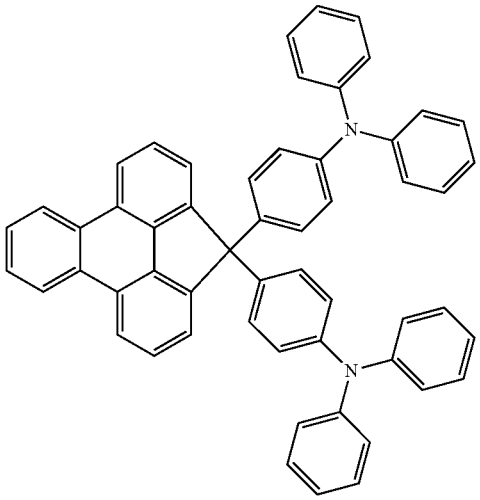
(50)
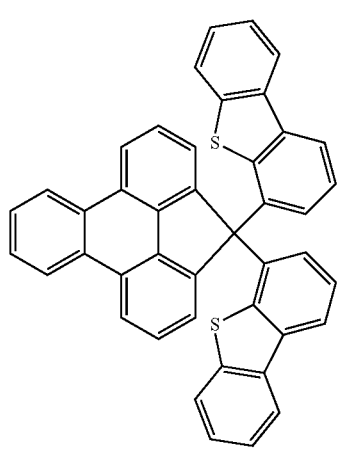
(53)
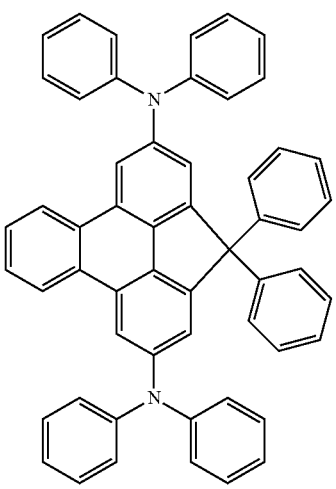
(51)
(54)
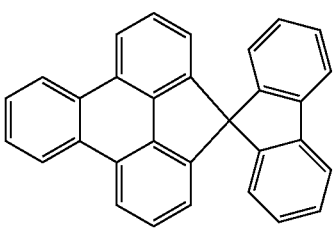

37
-continued
(55)
(56)
(57)
(58)
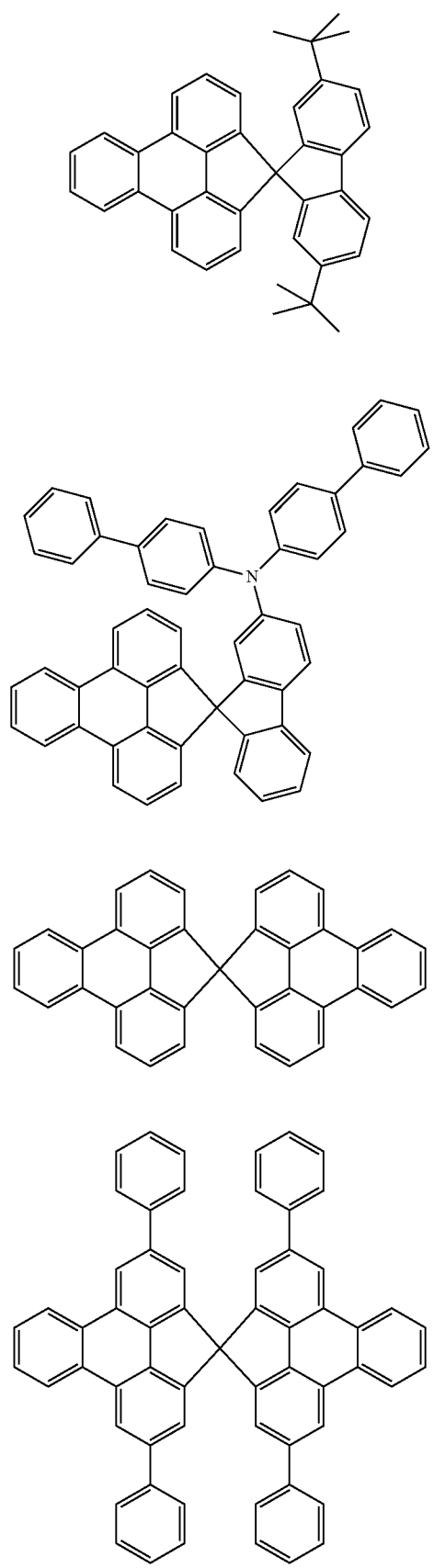
38
-continued
(59)
(60)
(61)
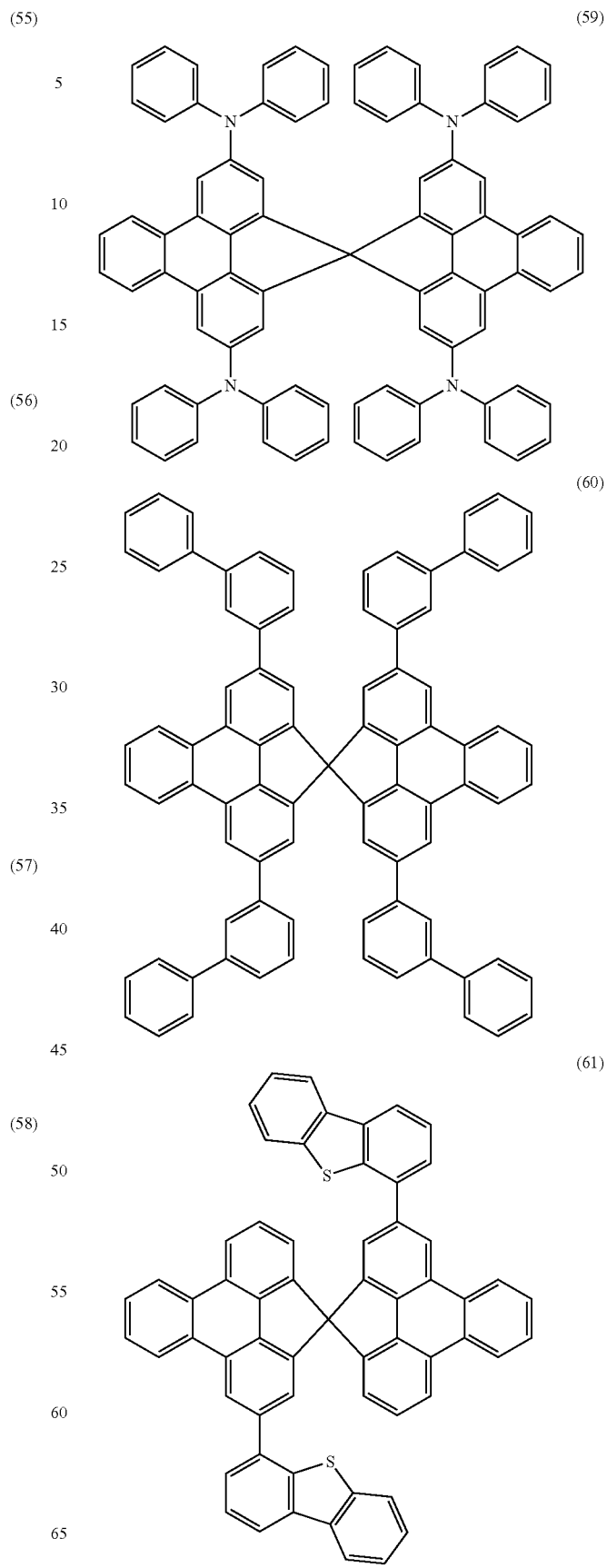

-continued
(62)
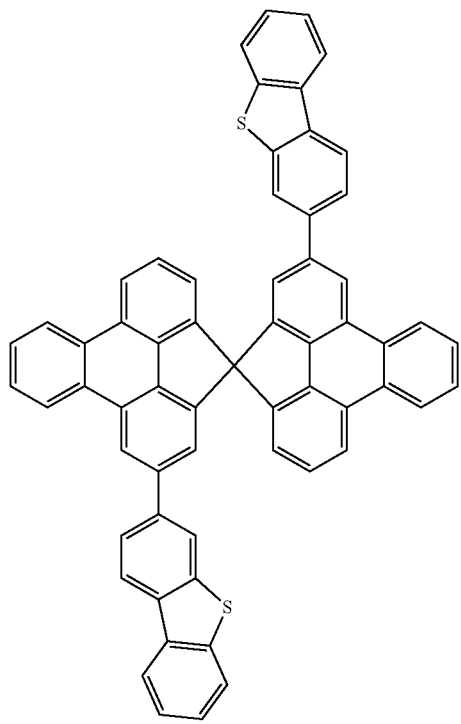
(63)
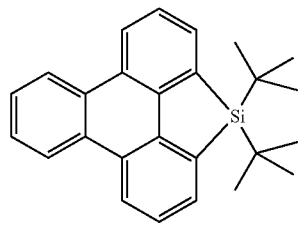
(64)
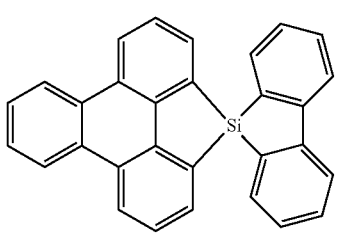
-continued
(65)
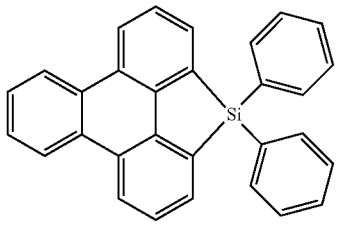
(66)
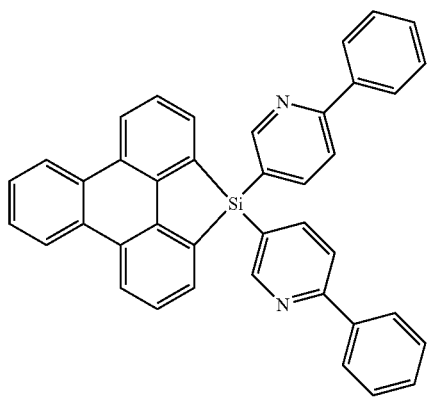
(67)
(68)

(69)
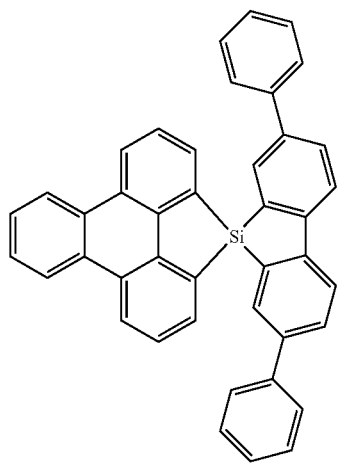
(70)
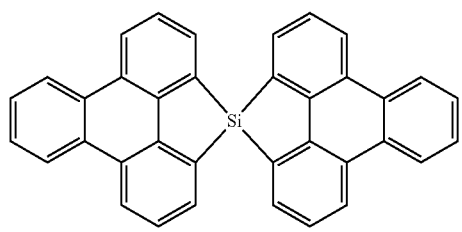
(71)
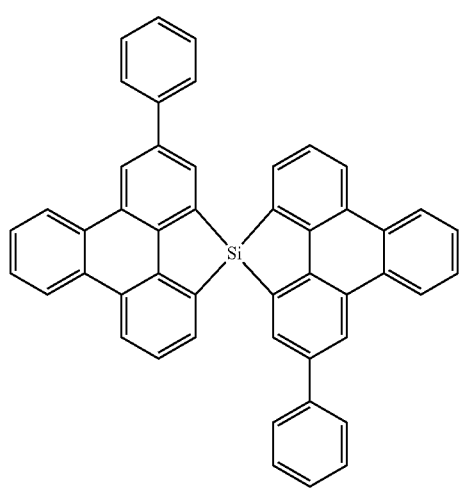
(72)
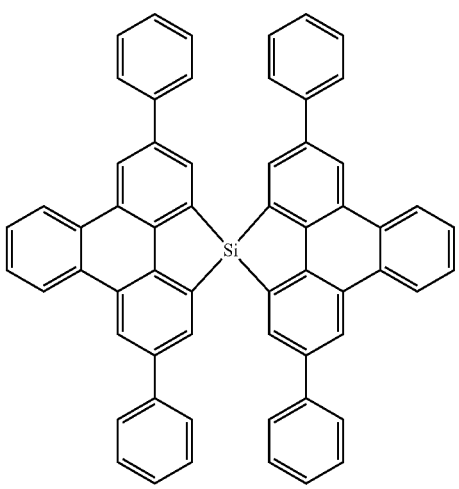
(73)
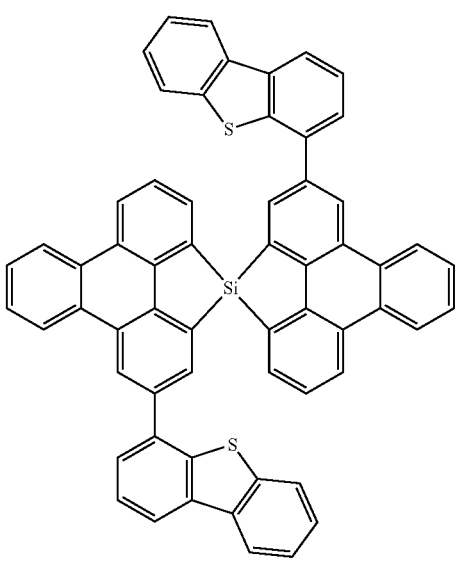
(74)
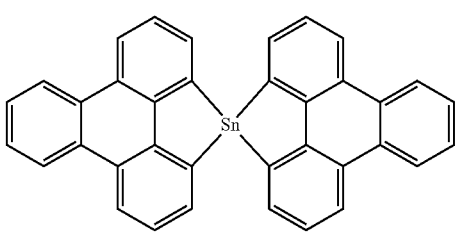

(75)
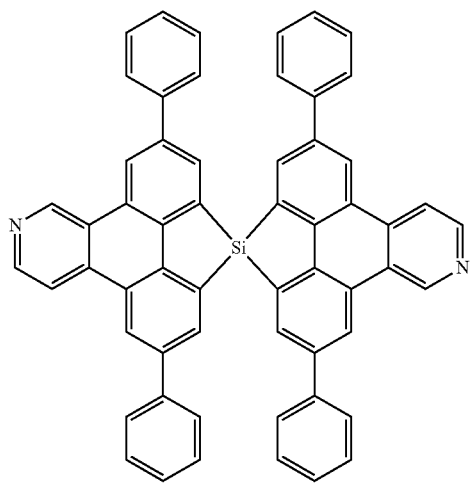
(76)
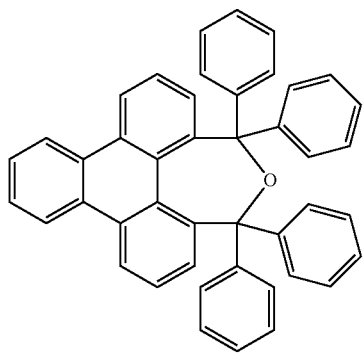
(77)
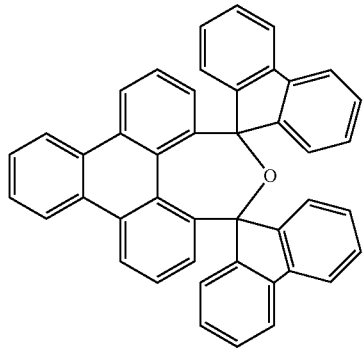
(78)
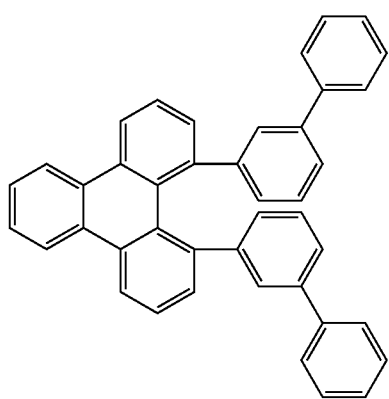
(79)
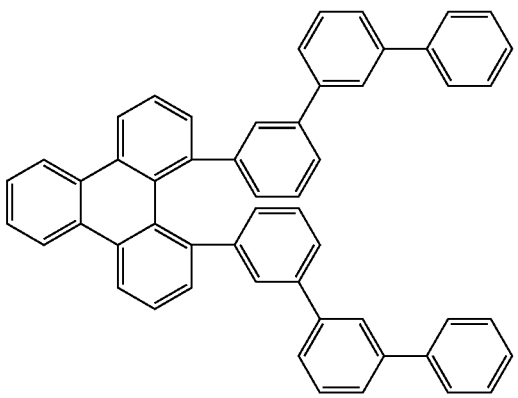
(80)
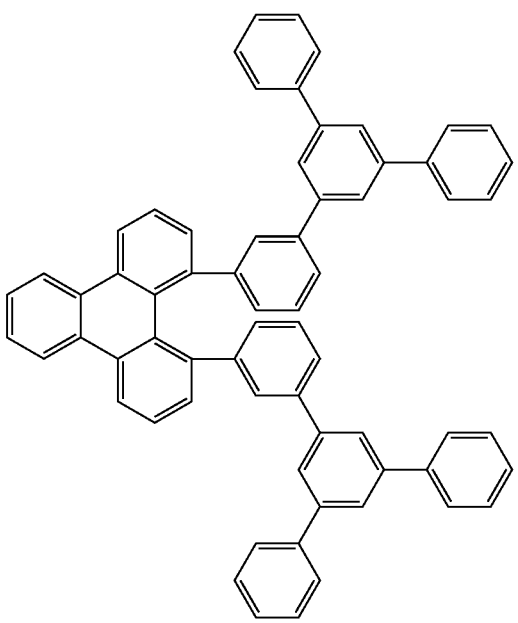
(80)
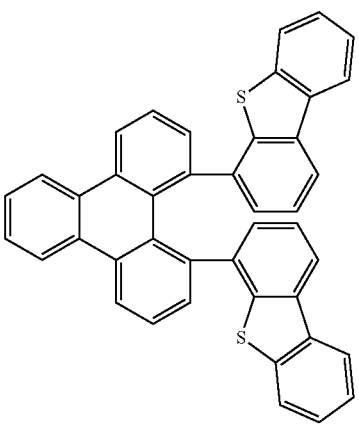

(81)
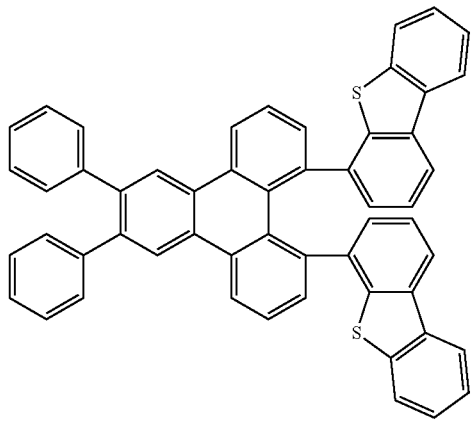
(82)
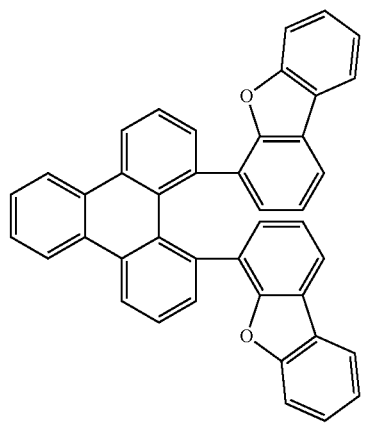
(83)
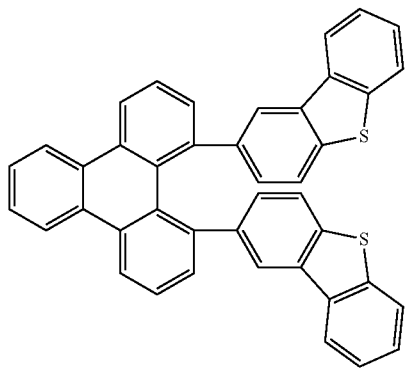
(84)
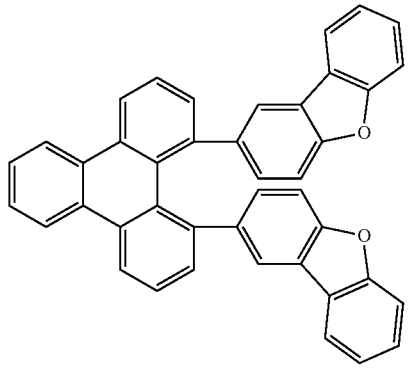
(85)
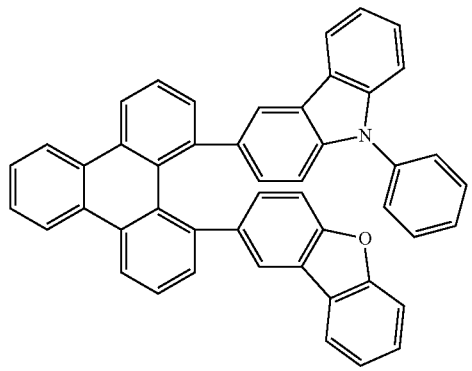
(86)
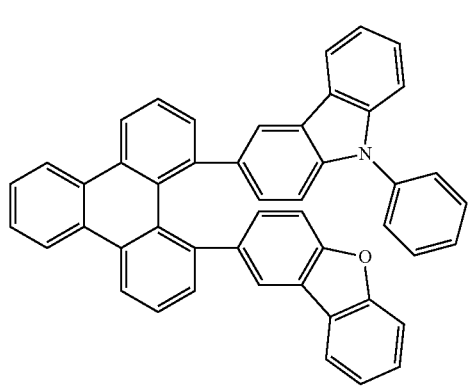
(87)
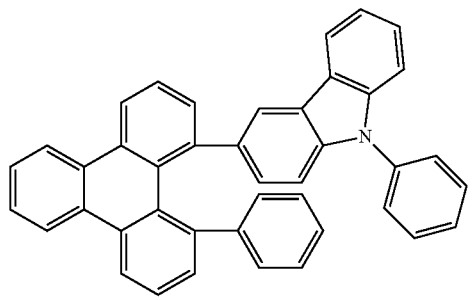
(88)
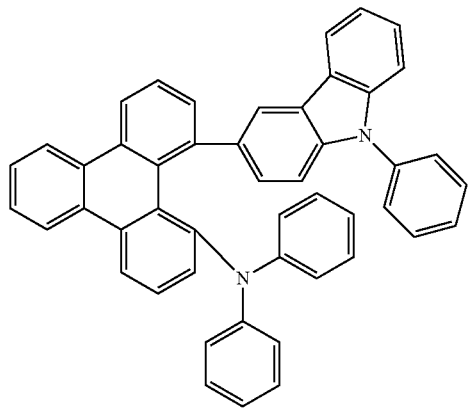

(89)
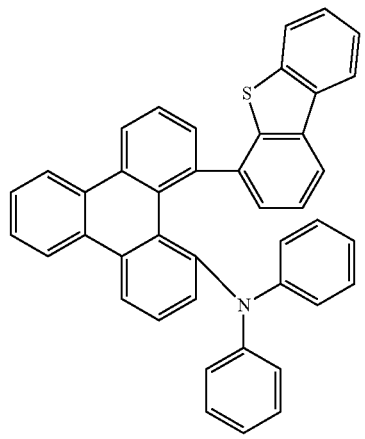

(90)
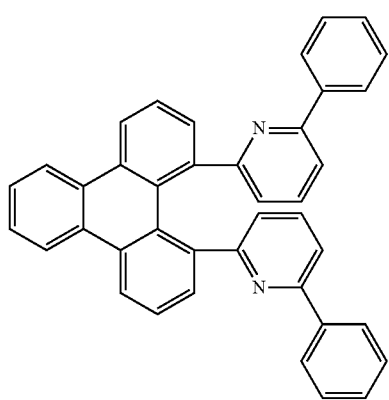

(91)
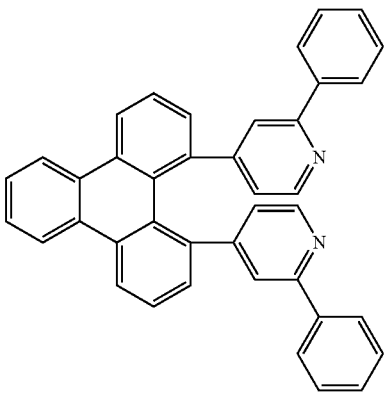

The compounds according to the invention can be prepared by synthetic steps known to the person skilled in the art, as depicted schematically in Scheme 1 to 3.

A suitable synthetic method is the reaction of 1,12-dilithiotriphenylene×2 TMEDA (Chanda et al., *Organometallics* 2007, 26(7), 1635-1642) with electrophiles to give the compounds of the formula 1 to 3 according to the invention, as depicted in Scheme 1.

Scheme 1:

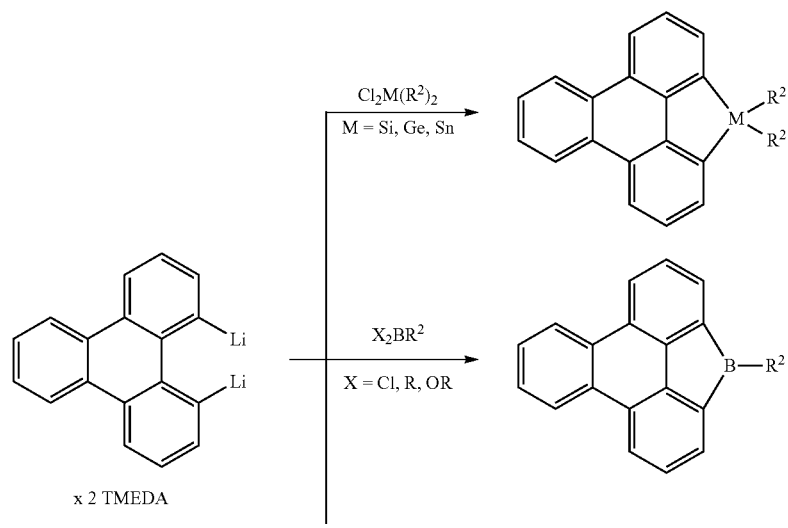

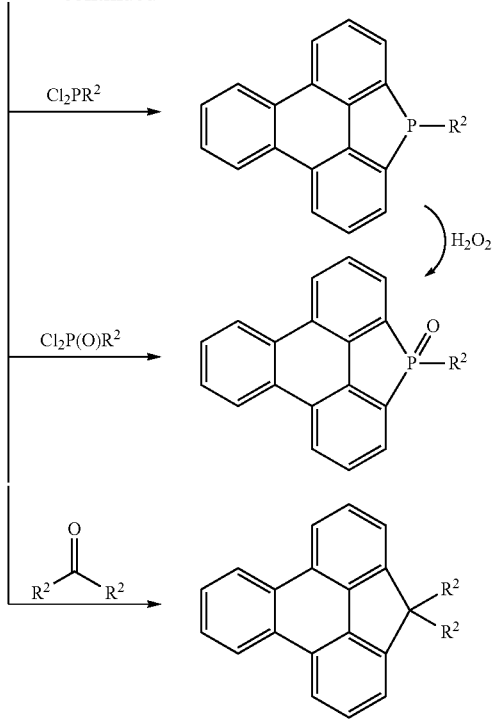

In addition, correspondingly substituted triphenylene derivatives can be converted into aromatic or heteroaromatic hydrocarbons, amines, ethers, thioethers, etc., by methods of organic chemistry which are familiar to the person skilled in the art, such as, for example, by Suzuki, Stille, Heck, Sonogashira, Yamamoto, Negishi, Ullmann or Buchwald couplings, as shown by way of example in Scheme 2. <Pd> here stands for a palladium catalyst.

Scheme 2:

C—C coupling, e.g. Suzuki coupling:

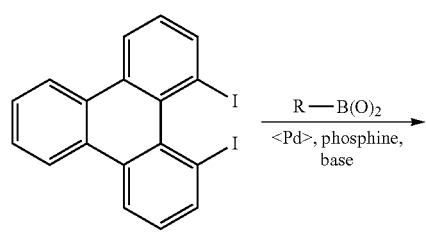

C—N coupling, e.g. Buchwald amination:

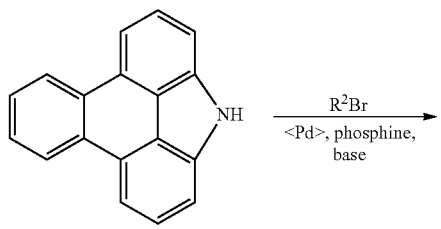

In addition, correspondingly substituted triphenylene derivatives (Saito et al., *J. Organomet. Chem.* 2010, 695(7), 1035-1041) can be functionalised further in a plurality of steps, as shown by way of example in Scheme 3.

Scheme 3:

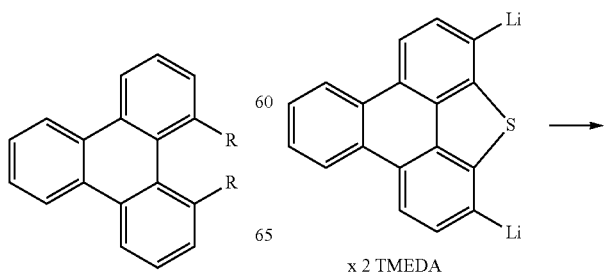

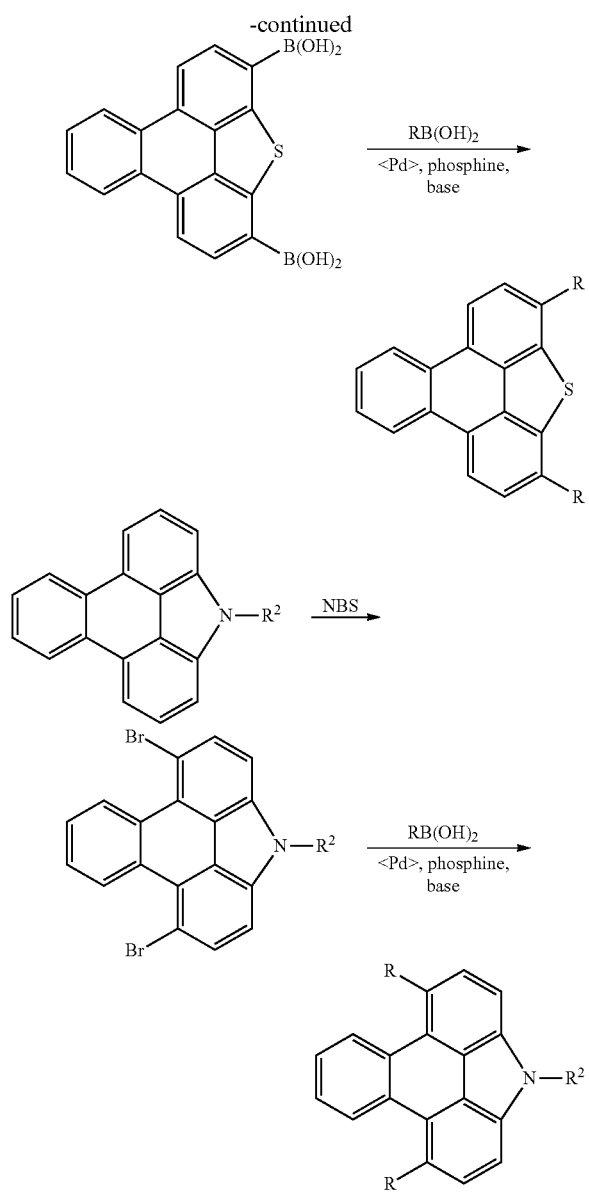

The present invention therefore furthermore relates to a process for the preparation of a compound of the formula (1) or (2) by reaction of 1,12-dilithiotriphenylene derivatives with electrophiles or by reaction of halogen- or amino-substituted triphenylene derivatives in a metal-catalysed coupling reaction.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1) or (2) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units. In addition, the polymers may contain phosphorescent emitters, either copolymerised or mixed in as a blend. In particular, the combination of units of the formula (1) or (2) or the preferred embodiments indicated above with phosphorescent emitters leads to particularly good results.

Furthermore, the compounds of the formula (1) or (2) or the preferred embodiments indicated above may also be functionalised further and thus converted into extended structures. The reaction with arylboronic acids by the Suzuki method or with primary or secondary amines by the HartwigBuchwald method may be mentioned here as an example. Thus, the compounds of the formula (1) or (2) or the preferred embodiments mentioned here may also be bonded directly to phosphorescent metal complexes or also to other metal complexes.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the above-mentioned compounds according to the invention in an electronic device, in particular in an organic electroluminescent device.

The present invention still furthermore relates to an electronic device comprising at least one of the above-mentioned compounds according to the invention. The preferences stated above likewise apply to the electronic devices.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013).

The compound according to the invention in accordance with the above-mentioned embodiments can be employed in various layers, depending on the precise structure. Preference is given to an organic electroluminescent device comprising a compound of the formula (1) or (2) or the preferred embodiments indicated above as matrix material for fluorescent or phosphorescent emitters, in particular for phosphorescent emitters, and/or as fluorescent emitter and/or in a hole-blocking layer and/or in an electron-transport layer and/or in an electron-blocking or exciton-blocking layer and/or in a hole-transport or hole-injection layer, depending on the precise substitution. The preferred embodiments indicated above also apply to the use of the materials in organic electronic devices.

In a further embodiment of the invention, the organic electroluminescent device comprises the compound of the formula (1) or (2) or the preferred embodiments indicated above in an optical coupling-out layer. An optical coupling-out layer here is taken to mean a layer which is not located between the anode and the cathode, but instead which is applied to an electrode outside the actual device, for example between an electrode and a substrate, in order to improve the optical coupling-out.

In a preferred embodiment of the invention, the compound of the formula (1) or (2) or the preferred embodiments indicated above is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or (2) or the preferred embodiments indicated above is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state>1, in particular from an excited triplet state. For the purposes of this application, all luminescent complexes with transition metals or lanthanides, in particular all iridium, platinum and copper complexes, are to be regarded as phosphorescent compounds.

The mixture of the compound of the formula (1) or (2) or the preferred embodiments indicated above and the emitting compound comprises between 99 and 1% by vol., preferably between 98 and 10% by vol., particularly preferably between 97 and 60% by vol., in particular between 95 and 80% by vol., of the compound of the formula (1) or (2) or the preferred embodiments indicated above, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or (2) or the preferred embodiments indicated above as matrix material for a phosphorescent emitter in combination with a further matrix material. Particularly suitable matrix materials which can be employed in combination with the compounds of the formula (1) or (2) or the preferred embodiments indicated above are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with the unpublished applications WO 2011/042107 or WO 2011/060867. A further phosphorescent emitter which emits at shorter wavelength than the actual emitter may likewise be present in the mixture as co-host.

Suitable as phosphorescent compound (=triplet emitter) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent compounds are indicated in the following table.

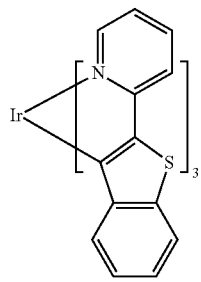

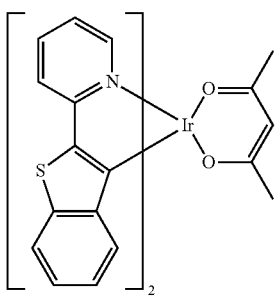

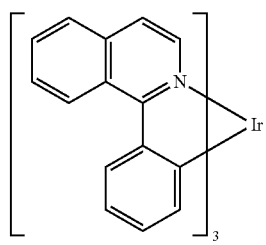

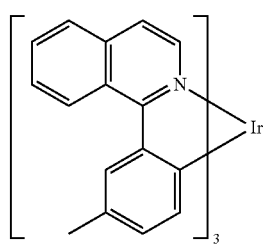

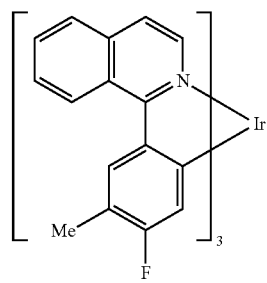

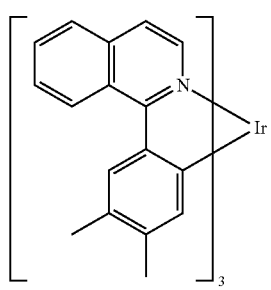

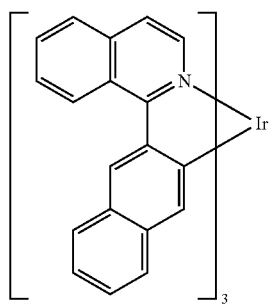

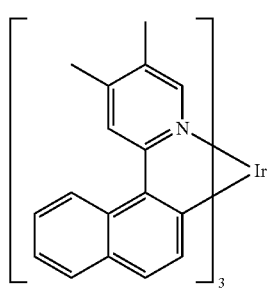

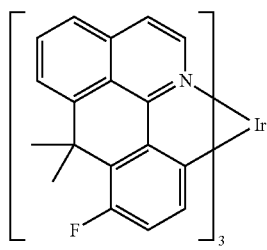

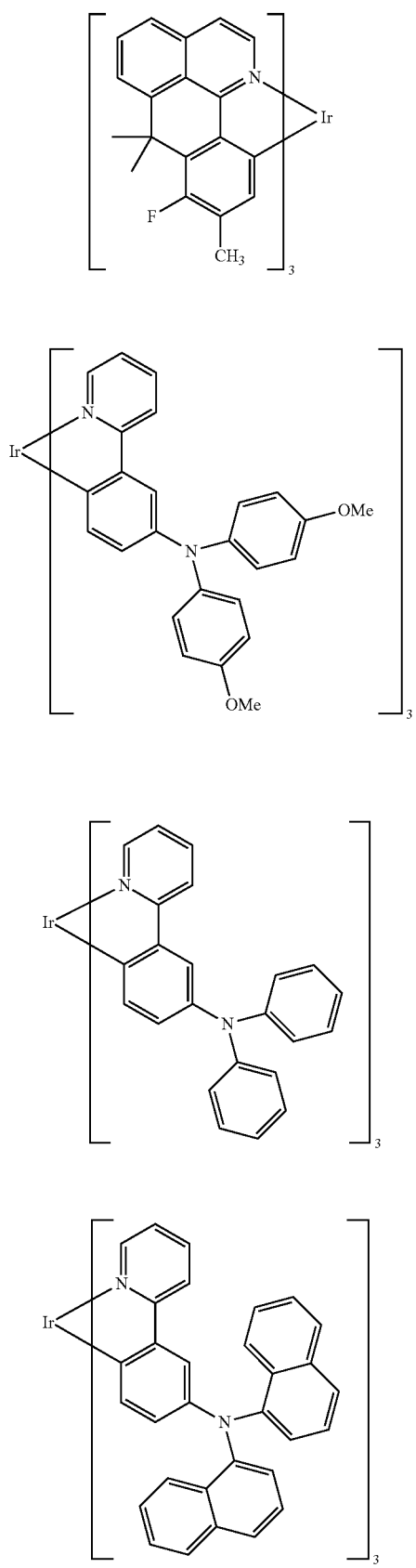
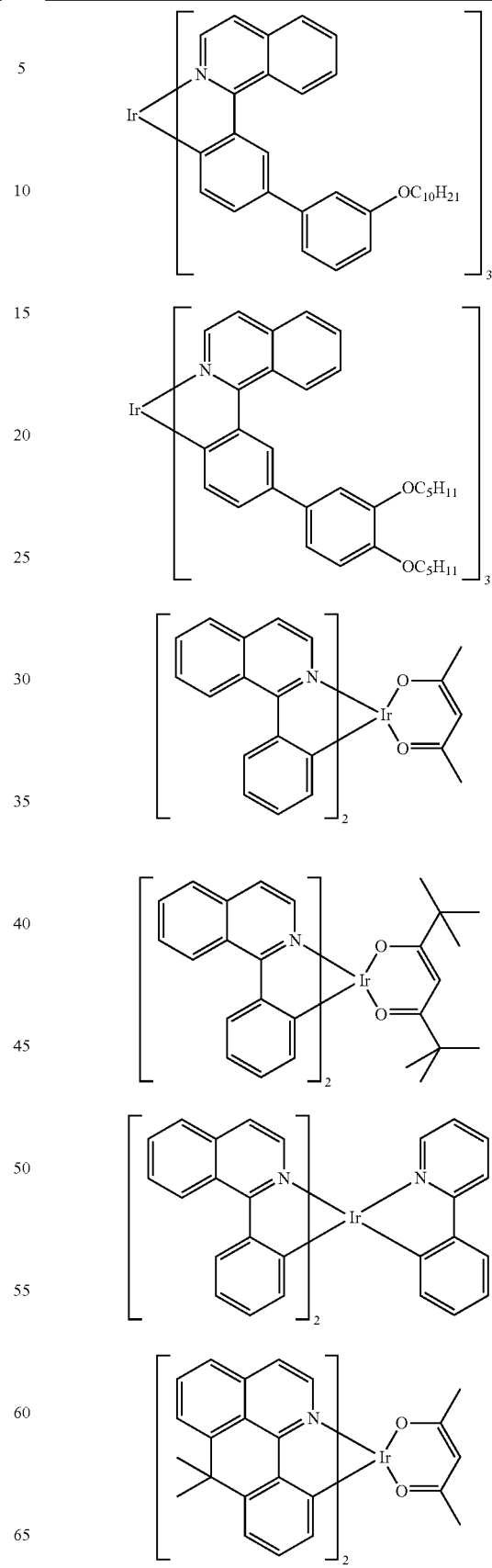

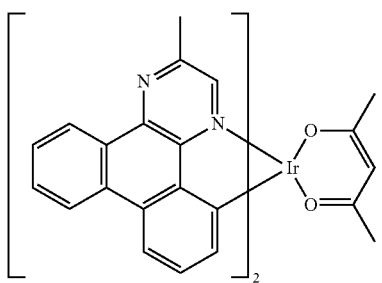
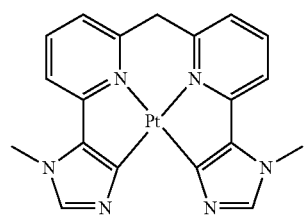
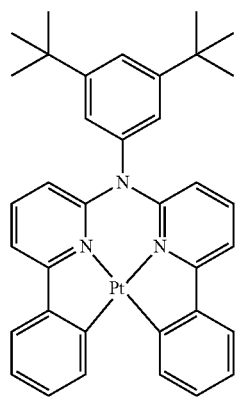
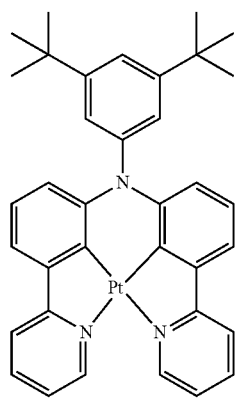
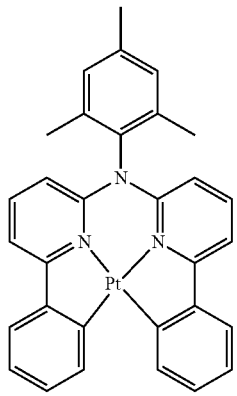
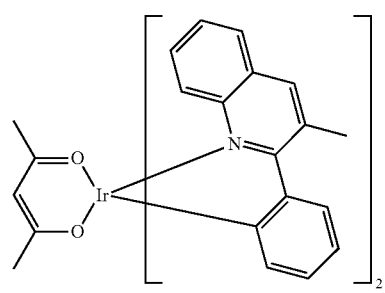
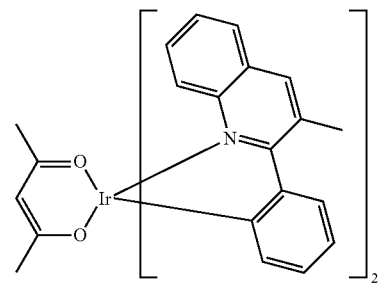
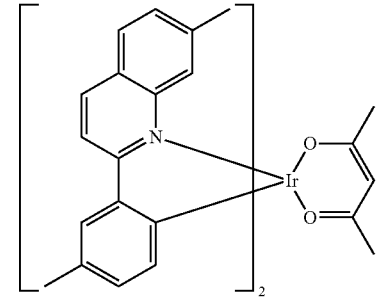
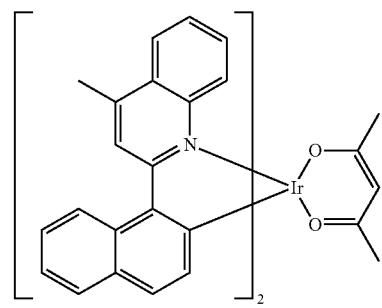

-continued
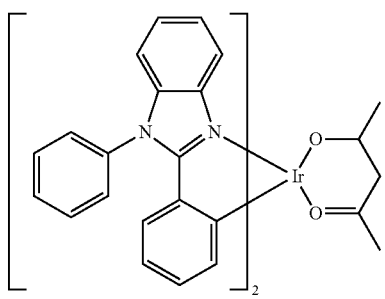
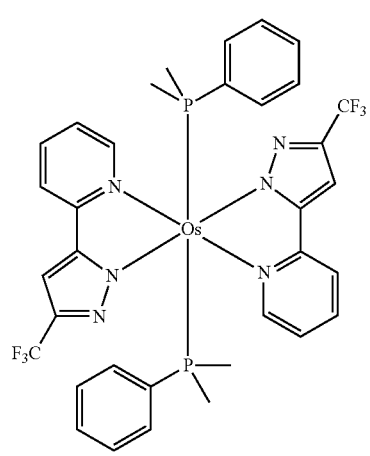
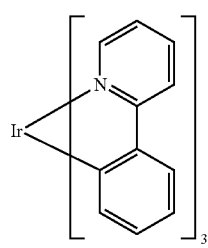
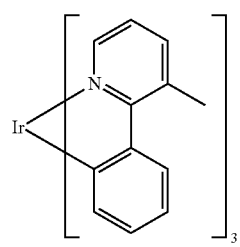
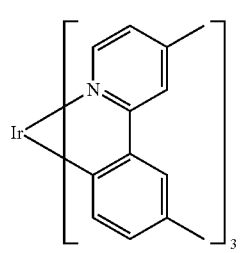
-continued
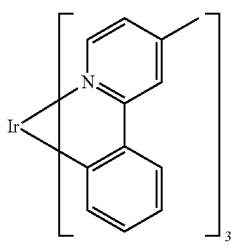
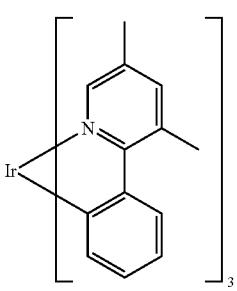
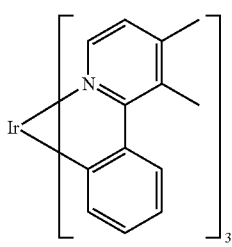
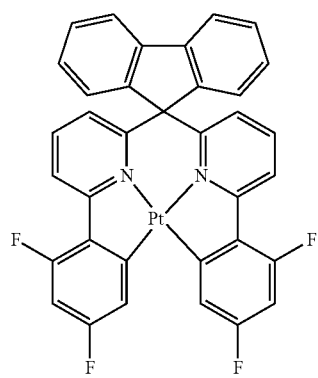
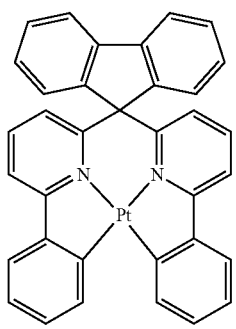

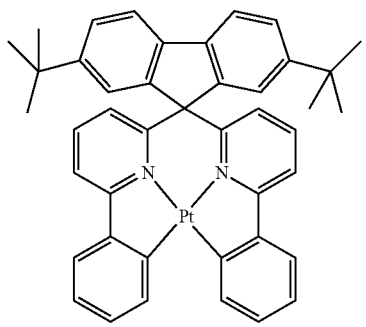
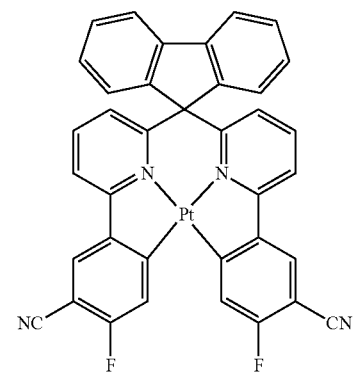
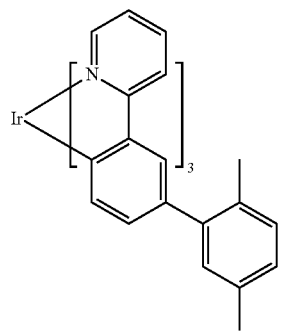
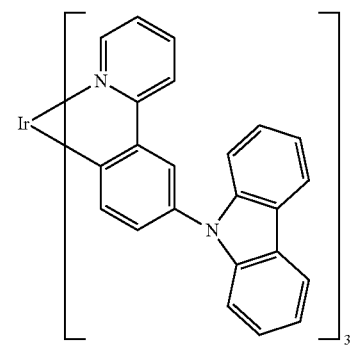
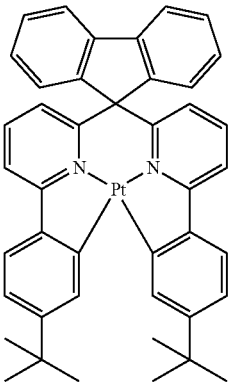
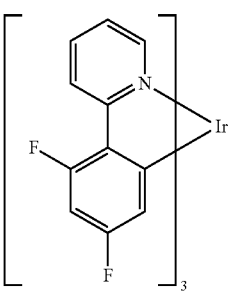
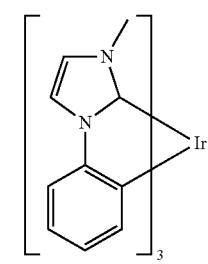
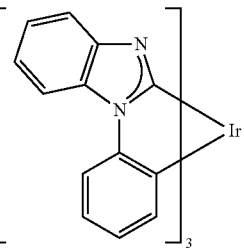
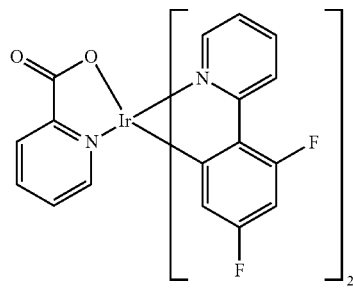

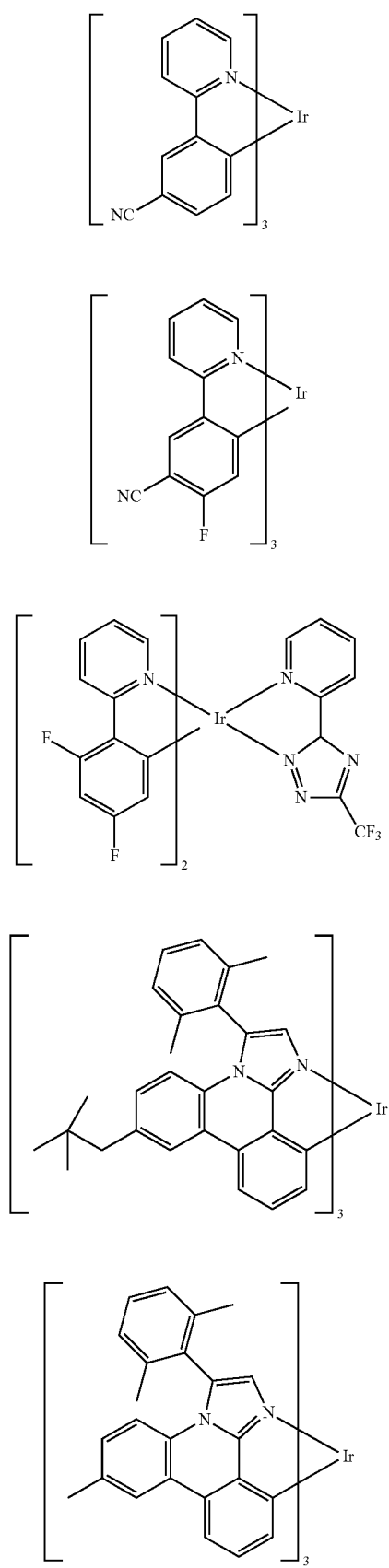
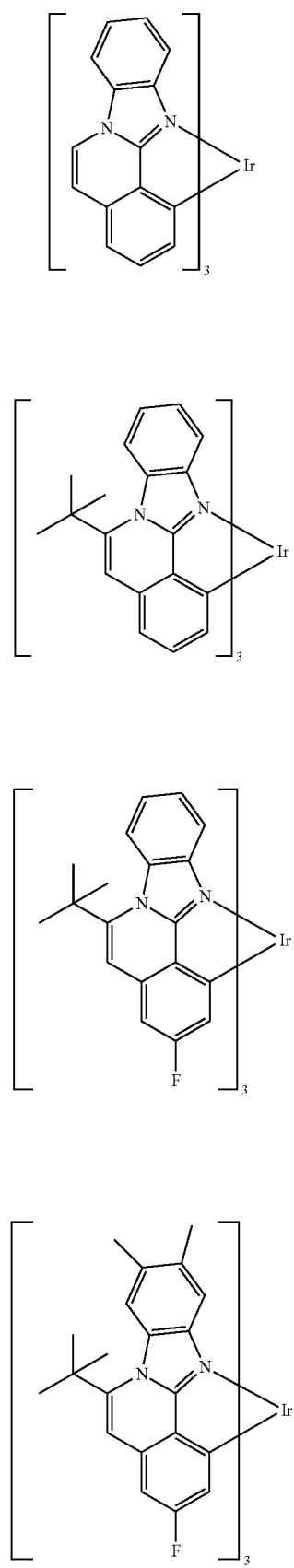

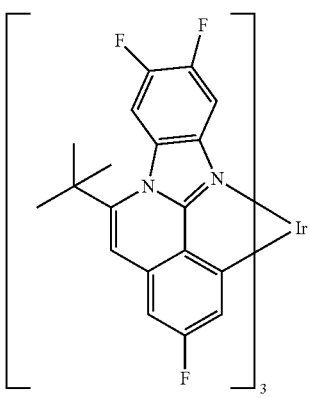
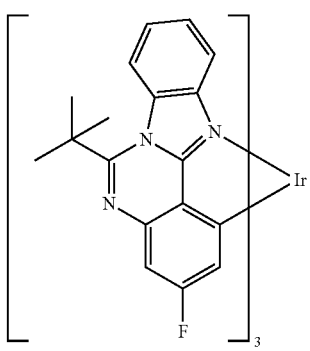
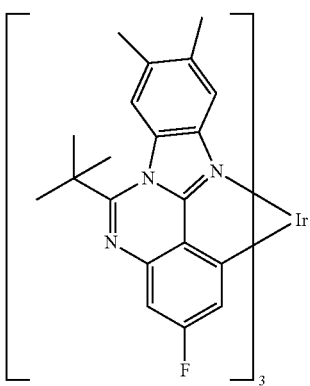
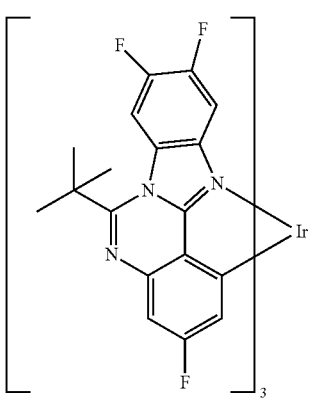
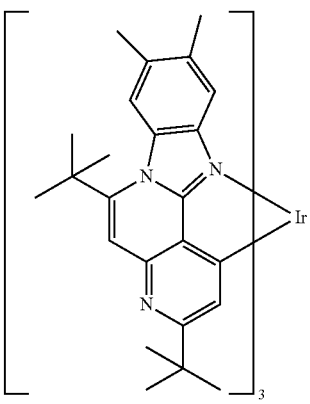
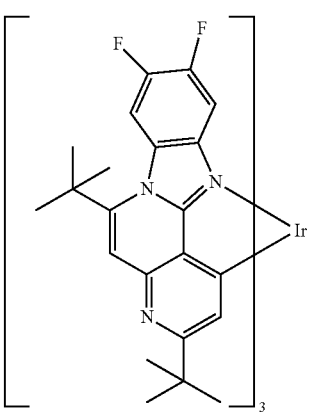
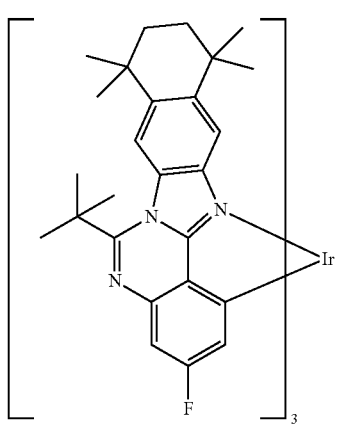
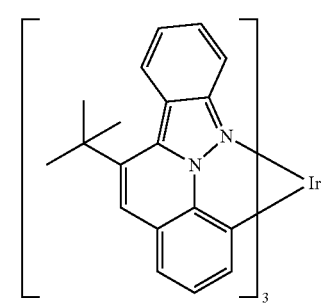

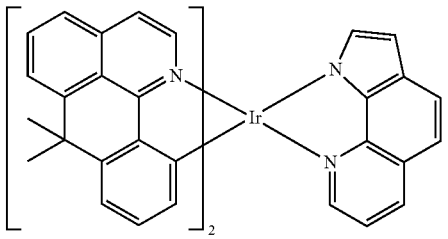

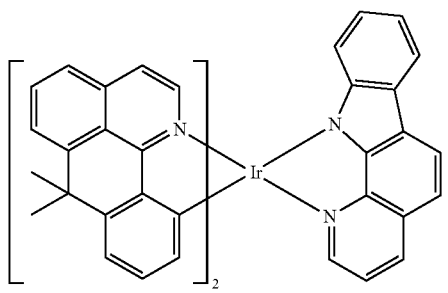

In a further embodiment of the invention, the organic electroluminescent device does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or (2) or the preferred embodiments indicated above will be employed as matrix material for a fluorescent emitter in an emitting layer.

Suitable fluorescent dopants are selected, for example, from the group of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic pyrenamines, aromatic pyrenediamines, aromatic chrysenamines or aromatic chrysenediamines. An aromatic anthracenamine is taken to mean a compound in which a diarylamino group is bonded directly to an anthracene group, preferably in the 9-position or in the 2-position. Aromatic pyrenamines, pyrenediamines, chrysenamines and chrysenediamines are defined analogously thereto, where the diarylamino groups on the pyrene are preferably bonded in the 1-position or in the 1,6-position. Further preferred dopants are selected from indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of dopants from the class of the styrylamines are substituted or unsubstituted tristilbenamines or the dopants described in WO 2006/000388, WO 2006/058737, WO 2006/000389, WO 2007/065549 and WO 2007/115610. Furthermore suitable fluorescent dopants are the condensed hydrocarbons disclosed in WO 2010/012328.

In a further preferred embodiment of the invention, the compound of the formula (1) or (2) or the preferred embodiments indicated above will be employed as fluorescent emitter in an emitting layer.

Suitable host materials (matrix materials) for the fluorescent dopants, in particular for the above-mentioned dopants, are selected, for example, from the classes of the oligoarylenes (for example 2,2',7,7'-tetraphenylspirobifluorene in accordance with EP 676461 or dinaphthylanthracene), in particular the oligoarylenes containing condensed aromatic groups, in particular anthracenes, the oligoarylenevinylenes (for example DPVBi or spiro-DPVBi in accordance with EP 676461), the polypodal metal complexes (for example in accordance with WO 2004/081017), the holeconducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052), the benzanthracene derivatives (for example benz[a]anthracene derivatives in accordance with WO 2008/145239 or WO 2011/012212) and the benzophenanthrene derivatives (for example benz [c]phenanthrene derivatives in accordance with WO 2010/083869). Particularly preferred host materials are selected from the classes of the oligoarylenes, containing naphthalene, anthracene, benzanthracene, in particular benz[a]anthracene, benzophenanthrene, in particular benz[c]phenanthrene, and/or pyrene, or atropisomers of these compounds. Very particularly preferred matrix materials for the fluorescent emitter are anthracene derivatives. An oligoarylene in the sense of this invention is intended to be taken to mean a compound in which at least three aryl or arylene groups are bonded to one another.

In a further preferred embodiment of the invention, the compound of the formula (1) or (2) or the preferred embodiments indicated above is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound of the formula (1) or (2) or the preferred embodiments indicated above is employed in a hole-blocking layer, in particular in a phosphorescent OLED. A hole-blocking layer is taken to mean a layer which is directly adjacent to an emitting layer on the cathode side.

It is furthermore possible to use the compound of the formula (1) or (2) or the preferred embodiments indicated above both in a hole-blocking layer or electron-transport layer and also as matrix in an emitting layer.

In still a further embodiment of the invention, the compound of the formula (1) or (2) or the preferred embodiments indicated above is employed in a hole-transport layer or in an electron-blocking layer or exciton-blocking layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or (2) according to the invention or the preferred embodiments indicated above.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose. These processes are also particularly suitable for oligomers, dendrimers and polymers.

Furthermore possible are hybrid processes, in which, for example, one or more layers are applied from solution and one or more further layers are applied by vapour deposition. Thus, it is possible, for example, for the emitting layer to be applied from solution and for an electron-transport layer to be applied to this layer by vacuum vapour deposition These processes are generally known to the person skilled in the art and can be applied by him without inventive step to organic electroluminescent devices comprising the compounds according to the invention.

For processing from solution, formulations, in particular solutions, suspensions or mini-emulsions, of the compounds according to the invention are required. The present invention therefore furthermore relates to formulations, in particular solutions, suspensions or mini-emulsions, comprising at least one compound according to the invention and at least one solvent, in particular an organic solvent.

The compounds according to the invention and the organic electroluminescent devices according to the invention are distinguished by the following surprising advantages over the prior art:

1. The compounds according to the invention or compounds of the formula (1) or (2) or the preferred embodiments indicated above, employed as matrix material for fluorescent or phosphorescent emitters, result in very high efficiencies and in long lifetimes. This applies, in particular, if the compounds are employed as matrix material for a phosphorescent emitter.
2. The compounds according to the invention or compounds of the formula (1) or (2) or the preferred embodiments indicated above are suitable not only as matrix for red-phosphorescent compounds, but also, in particular, for green-phosphorescent compounds.
3. The compounds according to the invention are accessible synthetically in a simple manner in few reaction steps and with high yields.
4. The compounds according to the invention, employed in organic electroluminescent devices, result in high efficiencies and in steep current/voltage curves with low use voltages.
5. Also on use as electron-transport material or as hole-transport material, the compounds according to the invention result in very good properties with respect to the efficiency, lifetime and operating voltage of organic electroluminescent devices.

These above-mentioned advantages are not accompanied by an impairment of the other electronic properties.

The invention is explained in greater detail by the following examples, without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

A) Synthesis Examples

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR. The CAS numbers of the starting materials are in each case indicated in square brackets.

Example 1: 4-(2,4,6-Trimethylphenyl)-4H-4-boracyclopenta[def]-triphenylene

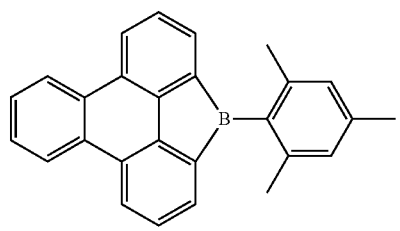 [SMILES: Cc1cc(C)c(B2c3cccc4c5ccccc5c5cccc2c5c34)c(C)c1]

A: 1,12-Dilithiotriphenylene*2 TMEDA 58.1 g (500 mmol) of N,N-tetramethylethylenediamine are added dropwise to 312.5 ml (500 mmol) of n-butyllithium (1.6 M in n-hexane), and the mixture is stirred at room temperature for 1 h. A solution of 22.8 g (100 mmol) of triphenylene in 150 ml of n-hexane is added dropwise to the mixture, which is subsequently heated under reflux for 5 h. After about 250 ml of n-hexane have been distilled off, the reaction mixture is allowed to cool and is then cooled at −30° C. for 24 h, during which a brown solid deposits. The brown solid is filtered off with suction, washed three times with 100 ml of ice-cold n-hexane each time and dried in vacuo. Yield: 134.7 g (285 mmol), 57%. Care: 1,12-dilithiotriphenylene*2 TMEDA is pyrophoric!

B: 4-(2,4,6-Trimethylphenyl)-41'-4-boracyclopenta[def]tsriphenylene

A solution of 20.1 g (100 mmol) of dichloro-2,4,6-trimethylphenylborane [69464-76-2] in 500 ml of THF is added dropwise to a solution of 47.2 g (100 mmol) of 1,12-dilithiotriphenylene*2 TMEDA in 1500 ml of THF, and the mixture is stirred at room temperature for 16 h. After removal of the solvent in vacuo, the residue is taken up in 500 ml of dichloromethane and washed three times with 200 ml of water each time. After drying over sodium sulfate, the organic phase is evaporated, the residue is recrystallised five times from dioxane and subsequently subjected to fractional sublimation in vacuo twice (p about $10^{-6}$ mbar, T about 300° C.). Yield 13.2 g (37 mmol), 37%. Purity: 99.9% according to HPLC.

The following compounds are accessible analogously by reaction of 1,12-dilithiotriphenylene*2 TMEDA with the corresponding electrophiles:

| Ex. | Electrophile | Product | Yield |
|---|---|---|---|
| 2 | [80-10-4] | | 38% |
| 3 | [18030-58-5] | | 32% |
| 4 | [32962-41-7] | | 26% |
| 5 | SiCl$_4$ [10026-04-7] | | 14% |

| Ex. | Electrophile | Product | Yield |
|---|---|---|---|
| 6 | [1135-99-5] | | 17% |
| 7 | [824-72-6] | | 41% |

Example 8: 1,10-Bis-(N-phenylcarbazol-2-yl)-4H-4-thiacyclopenta[def]-triphenylene A) Triphenyleno[1,12-bcd]thiophene-2,11-diboronic acid

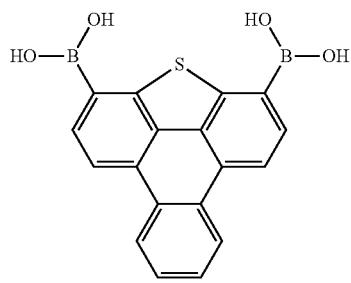 [SMILES: OB(O)c1ccc2c3ccccc3c3ccc(B(O)O)c4sc1c2c43]

48.8 g (420 mmol) of N,N-tetramethylethylenediamine are added to a suspension of 25.8 g (100 mmol) of triphenyleno[1,12-bcd]thiophene [68558-73-6] in 2000 ml of n-hexane, and 250 ml (400 mmol) of n-butyllithium (1.6 M in n-hexane) are then added dropwise, and the mixture is subsequently stirred at 60° C. for 4 h. After the mixture has been allowed to cool and cooled to −60° C., 46.8 g (450 mmol) of trimethyl borate are added in one portion with vigorous stirring. The mixture is stirred at −60° C. for a further 30 min., then allowed to warm to room temperature, the n-hexane is removed in vacuo, the residue is taken up in 300 ml of THF, a mixture of 300 ml of water and 30 ml of glacial acetic acid is added, the mixture is stirred for a further 2 h, the precipitated solid is filtered off with suction, washed twice with 200 ml of water each time and dried in vacuo. Yield: 30.7 g. Purity: about 90.0% according to NMR, the crude product is subsequently used without further purification.

B) 1,10-Bis-(N-phenylcarbazol-2-yl)-4H-4-thiacyclopenta[def]-triphenylene 913 mg (3 mmol) of tri-o-tolylphosphine and then 112 mg (0.5 mmol) of palladium(II) acetate are added with stirring to a mixture of 17.3 g (50 mmol) of triphenyleno[1,12-bcd]thiophene-2,11-diboronic acid, 41.9 g (130 mmol) of 2-bromo-9-phenylcarbazole [94994-62-4] and 31.8 g (150 mmol) of tripotassium phosphate in a mixture of 200 ml of toluene, 100 ml of ethanol and 300 ml of water, and the mixture is heated under reflux for 16 h. After cooling, the precipitated solid is filtered off with suction, washed three times with 100 ml of a mixture of water and ethanol (1:1, v:v) each time and then three times with 100 ml of ethanol each time and dried in vacuo. The solid is subjected to hot-vapour extraction with toluene over aluminium oxide (basic, activity grade 1) five times and then subjected to fractional sublimation in vacuo twice (p about $10^{-6}$ mbar, T about 350° C.). Yield 12.6 g (34 mmol), 34%. Purity: 99.9% according to HPLC.

The following compounds are accessible analogously by reaction of triphenyleno[1,12-bcd]thiophene-2,11-diboronic acid with the corresponding bromides:

| Ex. | Bromide | Product | Yield |
|---|---|---|---|
| 9 | 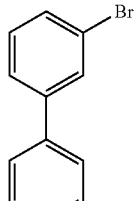 [2113-57-7] | 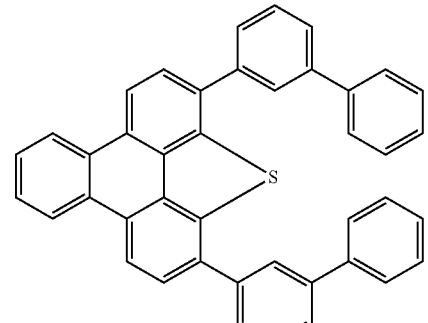 | 43% |
| 10 | 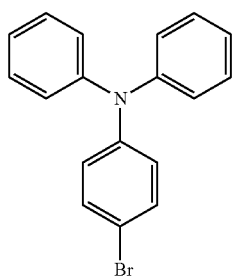 [36809-26-4] | 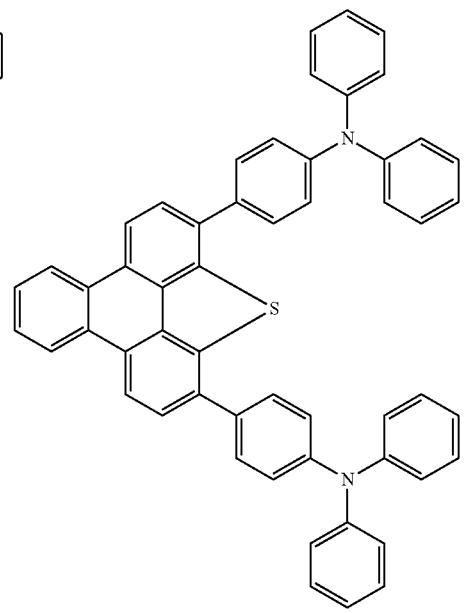 | 31% |

Example 11: 4-Biphenyl-4-yl-4H-4-azacyclopenta[def]triphenylene

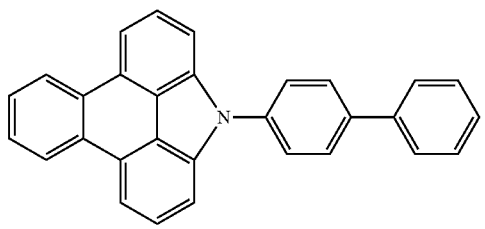 [SMILES: c1ccc(-c2ccc(-n3c4cccc5c6ccccc6c6cccc3c6c54)cc2)cc1]

235 mg (1.3 mmol) of di-tert-butylchlorophosphine and then 225 g (1 mmol) of palladium(II) acetate are added to a vigorously stirred suspension of 12.1 g (50 mmol) of 4H-4-azacyclopenta[def]triphenylene [109606-75-9], 14.0 g (60 mmol) of 4-bromobiphenyl and 9.0 g (65 mmol) of potassium carbonate in 150 ml of toluene, and the mixture is heated under reflux for 16 h. After cooling to 60° C., water is added, the mixture is stirred for a further 30 min., the precipitated solid is then filtered off with suction, washed three times with 100 ml of a mixture of water and ethanol (1:1, v:v) each time and then three times with 100 ml of ethanol each time and dried in vacuo. The solid is subjected to hot-vapour extraction with toluene over aluminium oxide (basic, activity grade 1) five times and then subjected to fractional sublimation in vacuo twice (p about $10^{-6}$ mbar, T about 320° C.). Yield: 7.3 g (19 mmol), 37%. Purity: 99.9% according to HPLC.

The following compounds are accessible analogously by reaction 4H-4-azacyclopenta[def]triphenylene with the corresponding bromides:

| Ex. | Bromide | Product | Yield |
|---|---|---|---|
| 12 | 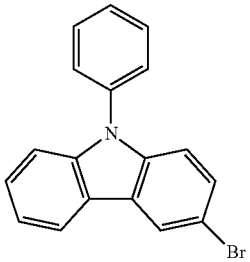 [1153-85-1] | 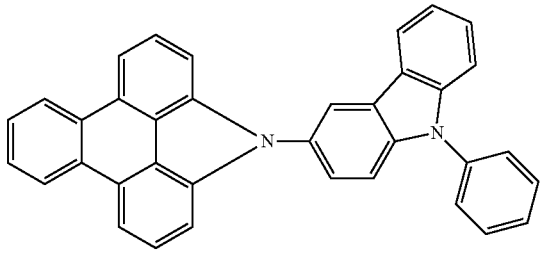 [SMILES: c1ccc(-n2c3ccccc3c3cc(-n4c5cccc6c7ccccc7c7cccc4c7c65)ccc32)cc1] | 52% |
| 13 | 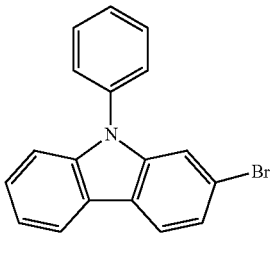 [94994-62-4] | 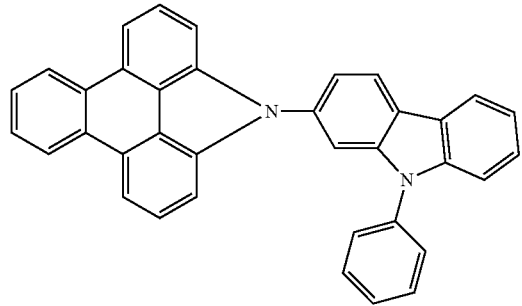 [SMILES: c1ccc(-n2c3ccccc3c3ccc(-n4c5cccc6c7ccccc7c7cccc4c7c65)cc32)cc1] | 44% |
| 28 | 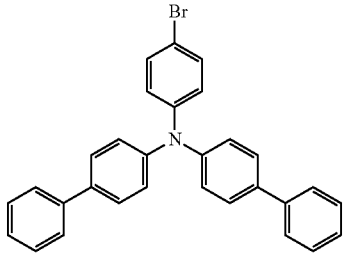 [499128-71-1] | 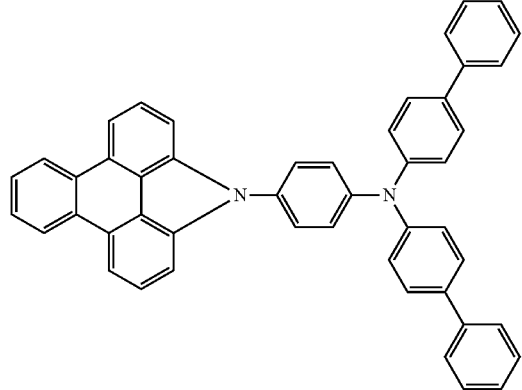 [SMILES: c1ccc(-c2ccc(N(c3ccc(-c4ccccc4)cc3)c3ccc(-n4c5cccc6c7ccccc7c7cccc4c7c65)cc3)cc2)cc1] | 38% |
| 29 | 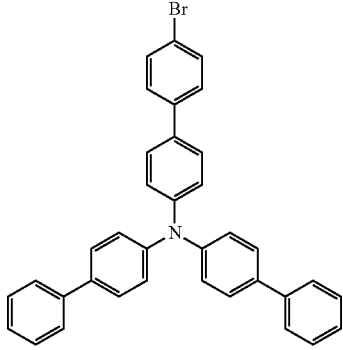 [728039-63-2] | 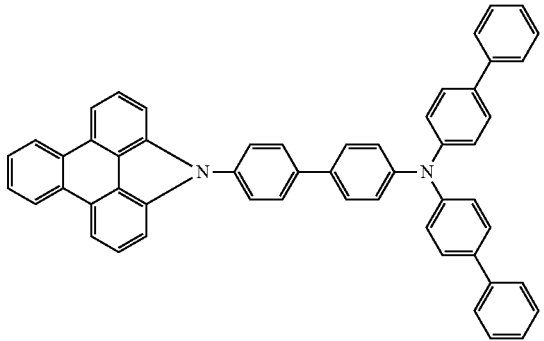 [SMILES: c1ccc(-c2ccc(N(c3ccc(-c4ccccc4)cc3)c3ccc(-c4ccc(-n5c6cccc7c8ccccc8c8cccc5c8c76)cc4)cc3)cc2)cc1] | 41% |

| Ex. | Bromide | Product | Yield |
|---|---|---|---|
| 30 | [67665-47-8] Use of 130 mmol of 4H-4-azacyclopenta[def]-triphenylene and 150 mmol of potassium carbonate | | 26% |
| 31 | [19111-87-6] | | 35% |
| 32 | [1257248-18-20] | | 42% |
| 33 | [1233200-57-1] | | 33% |

| Ex. | Bromide | Product | Yield |
|---|---|---|---|
| 34 | 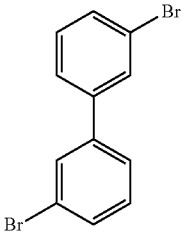<br>[16400-51-4]<br>Use of 130 mmol of 4H-4-azacyclopenta[def]-triphenylene and 150 mmol of potassium carbonate | 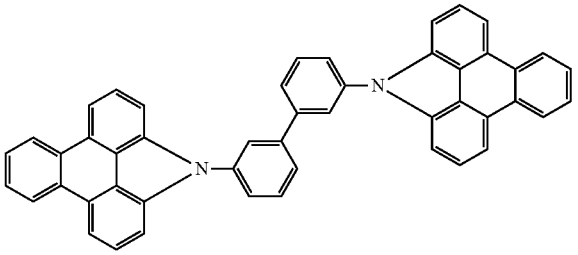 [SMILES: c1cc(-c2cccc(-n3c4cccc5c6ccccc6c6cccc3c6c54)c2)cc(-n2c3cccc4c5ccccc5c5cccc2c5c43)c1] | 24% |
| 35 | 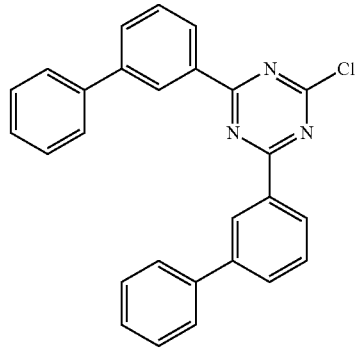<br>[1205748-61-3] | 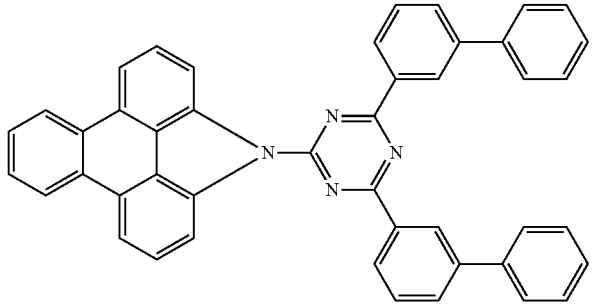 [SMILES: c1ccc(-c2cccc(-c3nc(-c4cccc(-c5ccccc5)c4)nc(-n4c5cccc6c7ccccc7c7cccc4c7c65)n3)c2)cc1] | 28% |
| 36 | 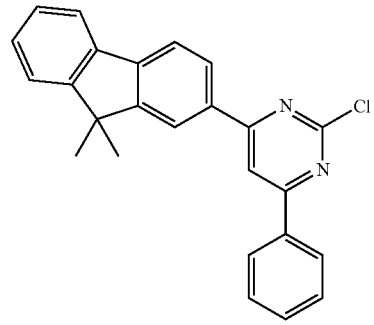<br>[1292291-85-0] | 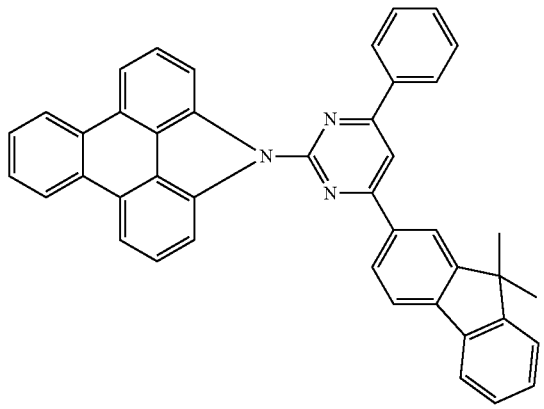 [SMILES: CC1(C)c2ccccc2-c2ccc(-c3cc(-c4ccccc4)nc(-n4c5cccc6c7ccccc7c7cccc4c7c65)n3)cc21] | 31% |
| 37 | 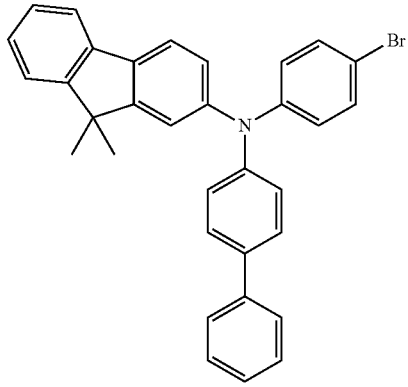<br>[1246562-40-2] | 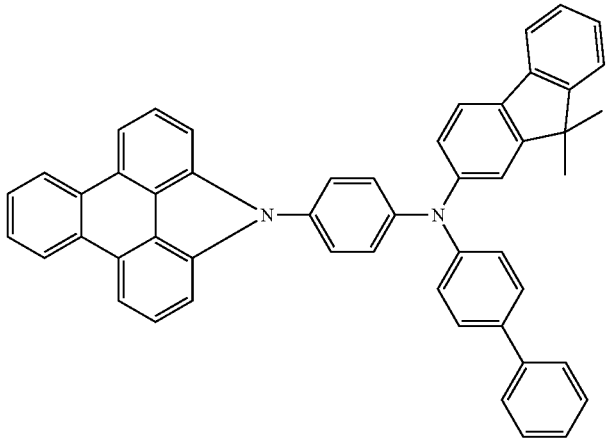 [SMILES: CC1(C)c2ccccc2-c2ccc(N(c3ccc(-c4ccccc4)cc3)c3ccc(-n4c5cccc6c7ccccc7c7cccc4c7c65)cc3)cc21] | 40% |

-continued
| Ex. | Bromide | Product | Yield |
|---|---|---|---|
| 38 | 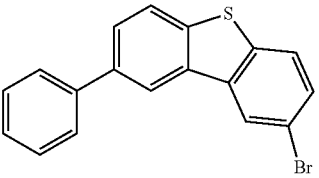 [1258016-27-1] | 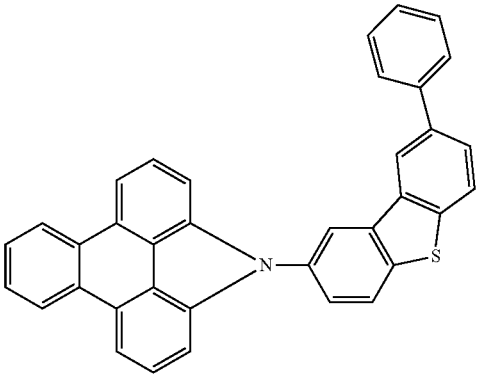 [SMILES: c1ccc(-c2ccc3sc4ccc(-n5c6cccc7c8ccccc8c8cccc5c8c76)cc4c3c2)cc1] | 30% |
| 39 | 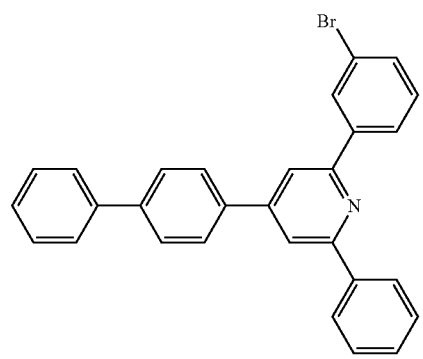 [895146-32-4] | 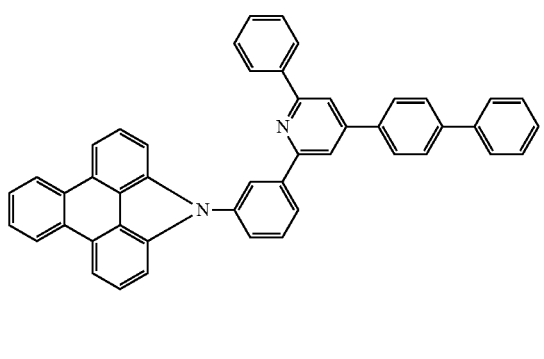 [SMILES: c1ccc(-c2ccc(-c3cc(-c4ccccc4)nc(-c4cccc(-n5c6cccc7c8ccccc8c8cccc5c8c76)c4)c3)cc2)cc1] | 22% |
| 40 | 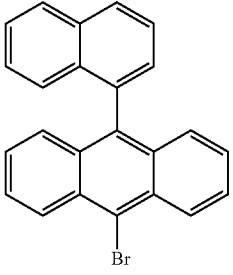 [400607-04-7] | 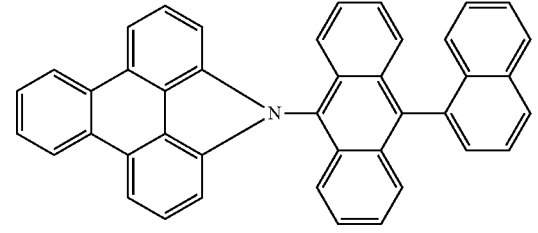 [SMILES: c1ccc2c(-c3c4ccccc4c(-n4c5cccc6c7ccccc7c7cccc4c7c65)c4ccccc34)cccc2c1] | 41% |
| 41 | 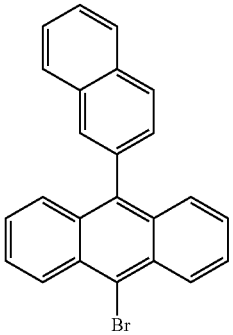 [474688-73-8] | 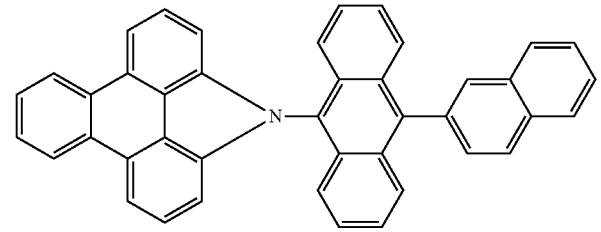 [SMILES: c1ccc2cc(-c3c4ccccc4c(-n4c5cccc6c7ccccc7c7cccc4c7c65)c4ccccc34)ccc2c1] | 44% |

-continued

| Ex. | Bromide | Product | Yield |
|---|---|---|---|
| 42 | [1092390-01-6] | | 38% |
| 43 | [523-27-3]<br>Use of 130 mmol of 4H-4-azacyclopenta[def]-triphenylene and 150 mmol of potassium carbonate | | 22% |
| 44 | [1160506-32-0] | | 34% |
| 45 | [1005771-04-9]<br>Use of 130 mmol of 4H-4-azacyclopenta[def]-triphenylene and 150 mmol of potassium carbonate | | 19% |

| Ex. | Bromide | Product | Yield |
|---|---|---|---|
| 46 | ![structure] [1001911-28-9] | ![structure] | 27% |

Example 14: 1,12-(Dibenzothiophen-2-yl)triphenylene

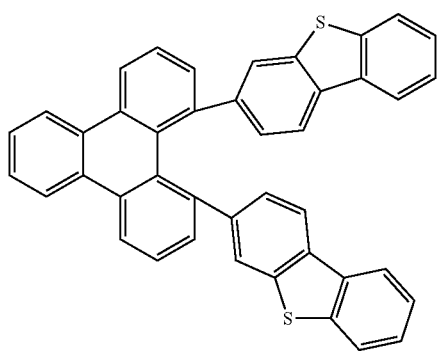 [SMILES: c1ccc2c(c1)sc1cc(-c3cccc4c5ccccc5c5cccc(-c6ccc7c(c6)sc6ccccc67)c5c34)ccc12]

304 mg (1 mmol) of tri-o-tolylphosphine and then 45 mg (0.2 mmol) of palladium(II) acetate are added with stirring to a mixture of 9.6 g (20 mmol) of 1,12-diiodotriphenylene [130197-34-1], 11.4 g (50 mmol) of 2-dibenzothiopheneboronic acid [108847-24-1] and 10.6 g (50 mmol) of tripotassium phosphate in a mixture of 200 ml of toluene, 50 ml of dioxane and 200 ml of water, and the mixture is heated under reflux for 30 h. After cooling, the precipitated solid is filtered off with suction, washed three times with 50 ml of a mixture of water and ethanol (1:1, v:v) each time and then three times with 50 ml of ethanol each time and dried in vacuo. The solid is subjected to hot-vapour extraction with toluene over aluminium oxide (basic, activity grade 1) four times and then subjected to fractional sublimation in vacuo twice (p about $10^{-6}$ mbar, T about 310° C.). Yield 5.0 g (8.4 mmol), 42%. Purity: 99.9% according to HPLC.

The following compounds are accessible analogously by reaction with the corresponding boronic acids:

| Ex. | Bromide | Product | Yield |
|---|---|---|---|
| 47 | ![structure] [854952-58-2] Use of 80 mmol | ![structure] | 13% |

| Ex. | Bromide | Product | Yield |
|---|---|---|---|
| 48 | [934603-99-3] | | 18% |

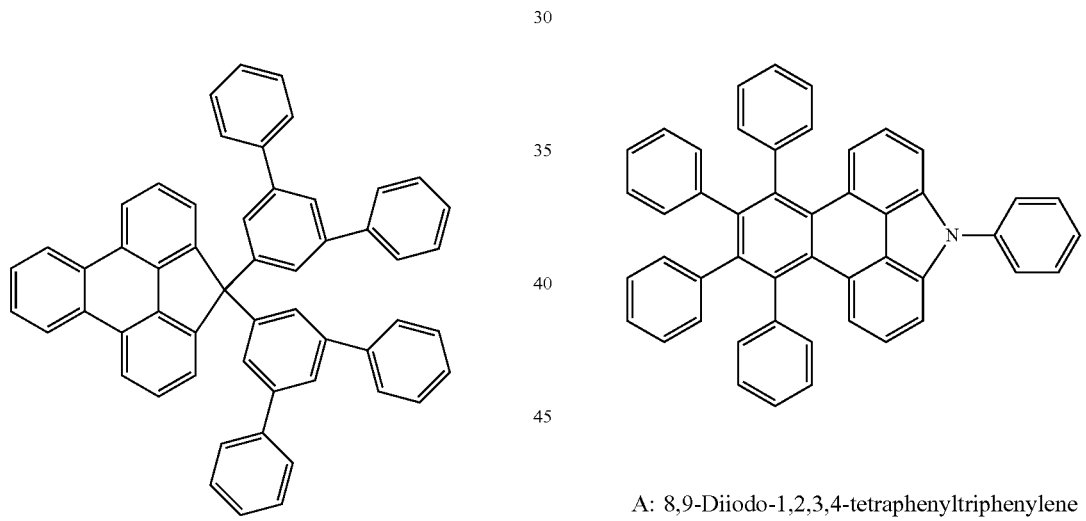

Example 15: 4,4-Bis[1,1',3',1"]terphenyl-5'-yl-4H-cyclopenta[def]-triphenylene

Example 49: 4,8,9,10-Pentaphenyl-4H-4-azacyclopenta[def]-triphenylene

A: 8,9-Diiodo-1,2,3,4-tetraphenyltriphenylene

A solution of 48.7 g (100 mmol) of bis[1,1',3',1"]terphenyl-5'-ylmethanone [1205748-29-3] in 500 ml of THF is added dropwise to a solution of 47.2 g (100 mmol) of 1,12-dilithiotriphenylene*2 TMEDA in 1500 ml of THF, and the mixture is then heated under reflux for 2 h. After quenching of the reaction mixture using 50 ml of ethanol and removal of the solvent in vacuo, the residue is taken up in 500 ml of glacial acetic acid, 20 ml of conc. hydrochloric acid and 20 ml of acetic anhydride are added to the suspension, and the mixture is heated under reflux for 3 h. After cooling, the precipitated solid is filtered off with suction, washed three times with 100 ml of ethanol each time and dried in vacuo. The solid is recrystallised five times from DMF and subsequently subjected to fractional sublimation in vacuo twice (p about $10^{-6}$ mbar, T about 350° C.). Yield: 38.3 g (55 mmol), 55%. Purity: 99.9% according to HPLC.

7.6 ml (50 mmol) of N,N-tetramethylethylenediamine are added dropwise to 31.3 ml (50 mmol) of n-butyllithium (1.6 M in n-hexane), and the mixture is stirred at room temperature for 1 h. A solution of 10.6 g (20 mmol) of 1,2,3,4-tetraphenyltriphenylene [36262-81-4] in 50 ml of n-hexane is added dropwise to the mixture, which is subsequently heated under reflux for 5 h. After about 75 ml of n-hexane have been distilled off, the reaction mixture is allowed to cool, is cooled to –100° C., 50 ml of THF are added, and a solution of 7.0 g (55 mmol) of iodine in 50 ml of THF is then slowly added dropwise. When the addition is complete, the mixture is allowed to warm slowly to room temperature. The reaction mixture is diluted with 200 ml of ethyl acetate, then washed once with 100 ml of saturated sodium sulfite solution, twice with 100 ml of water each time and once with 100 ml of sat. sodium chloride solution. After drying over magnesium sulfate and removal of the solvent in vacuo, the mixture is chromatographed on silica gel with heptane/ethyl acetate (4:1, v/v). Yield 7.1 g (9 mmol), 45%. Purity: 95% according to HPLC.

B:

A mixture of 7.8 g (10 mmol) of 8,9-diiodo-1,2,3,4-tetraphenyltriphenylene, 1.0 ml (11 mmol) of aniline, 2.4 g (25 mmol) of sodium tert-butoxide, 809 mg (4 mmol) of tri-tert-butylphosphine, 500 mg (2 mmol) of palladium(II) acetate and 100 ml of toluene is heated under reflux for 16 h. After cooling, 100 ml of toluene are added to the reaction mixture, the mixture is washed twice with 100 ml of water each time, dried over magnesium sulfate, and the solvent is then removed in vacuo. The solid obtained in this way is subjected to hot-vapour extraction with toluene over aluminium oxide (basic, activity grade 1) four times and then subjected to fractional sublimation in vacuo twice (p about $10^{-6}$ mbar, T about 370° C.). Yield 2.9 g (4.6 mmol), 46%. Purity: 99.9% according to HPLC.

The following compounds are accessible analogously by reaction with the corresponding amines:

water; purchased from H. C. Starck, Goslar, Germany) for improved processing. These coated glass plates form the substrates to which the OLEDs are applied. The OLEDs have in principle the following layer structure: substrate/hole-injection layer (HIL, with HIL1, 20 nm)/hole-transport layer (HTL, with HTM1 (reference) or the HTMs according to the invention, 20 nm)/electron-blocking layer, optional (EBL, 10 nm)/emission layer (EML with the individual matrices according to the invention or mixed matrices M, 40 nm)/electron-transport layer (ETL, with ETL1, 20 nm)/electron-injection layer (EIL, with LIF, 1 nm) and finally a cathode. The cathode is formed by an aluminium layer with a thickness of 100 nm. The precise structure of the OLEDs, in particular the structure of the hole-conductor or emitter layer, and the results obtained with these OLEDs on use of the compounds according to the invention as hole-conductor material, matrix materials for phosphorescent emitters, as matrix materials for fluorescent emitters and as fluorescent dopants is shown in Table 1, 2, 3 and 4.

The % data here relate to % by vol. The results for the use of compounds according to the invention both as matrix

| Ex. | Amine | Product | Yield |
|---|---|---|---|
| 50 | 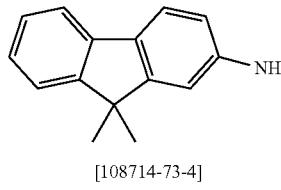 [108714-73-4] | 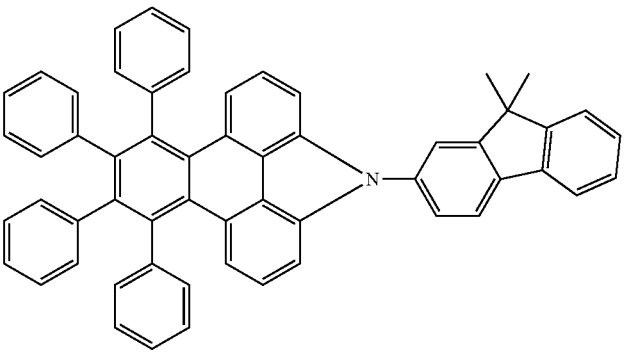 [SMILES: CC1(C)c2ccccc2-c2ccc(-n3c4cccc5c6c(-c7ccccc7)c(-c7ccccc7)c(-c7ccccc7)c(-c7ccccc7)c6c6cccc3c6c54)cc21] | 38% |
| 51 | 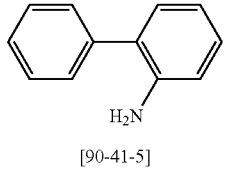 [SMILES: Nc1ccccc1-c1ccccc1] [90-41-5] | 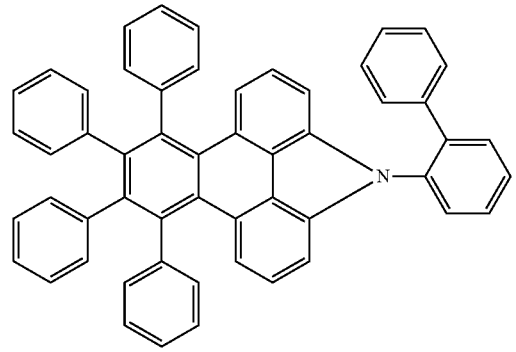 [SMILES: c1ccc(-c2ccccc2-n2c3cccc4c5c(-c6ccccc6)c(-c6ccccc6)c(-c6ccccc6)c(-c6ccccc6)c5c5cccc2c5c43)cc1] | 30% |

B) Device Examples

Example 16: Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples (see Tables 1, 2, 3, 4). Glass plates coated with structured ITO (indium tin oxide) in a thickness of 150 nm are coated with 20 nm of PEDOT (poly(3,4-ethylenedioxy-2,5-thiophene), applied by spin coating from materials for phosphorescent emitters and also as hole-transport materials are shown in Table 1, 2, 3 and 4. Results for the use of compounds according to the invention both as matrix materials for fluorescent emitters, as blue-fluorescent emitters and also as hole-transport materials are shown in Table 5.

The materials used for the production of the OLEDs are shown in Table 6.

All materials are applied by thermal vapour deposition in a vacuum chamber. The emission layer here always consists of at least one matrix material (host material) and an emitting dopant (emitter), with which the matrix material or matrix materials is admixed in a certain proportion by volume by co-evaporation.

The as yet unoptimised OLEDs are characterised by standard methods. For this purpose, the electroluminescence spectra, the current efficiency (measured in cd/A) and the voltage are determined. The efficiencies and voltages indicated in the tables relate to the corresponding values at an operating luminance of 1000 cd/m².

TABLE 1

Green-emitting OLEDs

| Ex. | EML | Efficiency [cd/A] | Voltage [V] | CIE, x/y |
|---|---|---|---|---|
| 17 | Ex. 1: TEG1 (15%) | 40.0 | 4.7 | 0.34/0.62 |
| 18 | Ex. 2: TEG1 (15%) | 43.9 | 4.8 | 0.33/0.62 |
| 19 | Ex. 5: TEG1 (10%) | 51.0 | 4.6 | 0.33/0.62 |
| 20 | Ex. 5: TEG2 (15%) | 54.7 | 4.5 | 0.32/0.61 |
| 21 | Ex. 5 (60%): EBL (25%): TEG2 (15%) | 55.4 | 4.2 | 0.32/0.61 |
| 22 | Ex. 8: TEG2 (15%) | 28.0 | 4.1 | 0.33/0.61 |
| 23 | Ex. 14: TEG2 (15%) | 45.2 | 4.2 | 0.32/0.61 |

TABLE 2

Green-emitting OLEDs without EBL

| Ex. | HTM/EML | Efficiency [cd/A] | Voltage [V] | CIE, x/y |
|---|---|---|---|---|
| 17 | Ex. 28/ TMM1: TEG2 (10%) | 46.0 | 4.0 | 0.34/0.61 |
| 52 | Ex. 29/ TMM1: TEG2 (10%) | 57.9 | 3.8 | 0.35/0.61 |
| 53 | Ex. 37/ TMM1: TEG2 (10%) | 67.0 | 3.9 | 0.35/0.61 |
| 54 | Ex. 29/ TMM1 (60%) Ex. 29 (33%) TEG2 (7%) | 64.5 | 3.7 | 0.35/0.61 |
| 55 | Ex. 29/ TMM1 (60%) Ex. 37 (33%) TEG2 (7%) | 66.1 | 3.8 | 0.35/0.61 |
| 56 | Ex. 29/ Ex. 30 (60%) Ex. 29 (33%) TEG2 (7%) | 56.0 | 4.2 | 0.34/0.61 |
| 57 | Ex. 29/ Ex. 31 (60%) Ex. 29 (33%) TEG2 (7%) | 45.8 | 4.3 | 0.35/0.61 |
| 58 | Ex. 29/ Ex. 32 (70%) Ex. 29 (25%) TEG1 (5%) | 61.8 | 3.9 | 0.33/0.62 |
| 59 | Ex. 29/ Ex. 33 (70%) Ex. 29 (25%) TEG2 (5%) | 43.8 | 4.4 | 0.34/0.61 |
| 60 | Ex. 29/ Ex. 34 (60%) Ex. 29 (33%) TEG2 (7%) | 48.9 | 4.2 | 0.35/0.61 |
| 61 | Ex. 29/ Ex. 35 (60%) Ex. 29 (30%) TEG2 (10%) | 58.5 | 3.8 | 0.35/0.61 |
| 62 | Ex. 29/ Ex. 36 (65%) Ex. 29 (30%) TEG2 (5%) | 61.6 | 3.8 | 0.35/0.61 |
| 63 | Ex. 29/ Ex. 38 (65%) Ex. 29 (30%) TEG2 (5%) | 57.7 | 4.0 | 0.34/0.62 |
| 64 | Ex. 37/ Ex. 49 (50%) Ex. 29 (45%) TEG2 (5%) | 45.2 | 4.1 | 0.35/0.61 |
| 65 | Ex. 29/ Ex. 50 (60%) Ex. 29 (33%) TEG2 (7%) | 50.7 | 4.0 | 0.35/0.61 |
| 66 | Ex. 29/ Ex. 51 (70%) Ex. 29 (33%) TEG2 (7%) | 49.3 | 4.2 | 0.35/0.61 |

TABLE 3

Red-emitting OLEDs

| Ex. | EML | Efficiency [cd/A] | Voltage [V] | CIE, x/y |
|---|---|---|---|---|
| 24 | Ex. 13: TER1 (15%) | 12.4 | 4.8 | 0.67/0.33 |
| 25 | Ex. 11: (20%) Ex. 15: (70%) TER2 (10%) | 13.6 | 4.6 | 0.67/0.33 |

TABLE 4

Red-emitting OLEDs, without EBL

| Ex. | HTM/EML | Efficiency [cd/A] | Voltage [V] | CIE, x/y |
|---|---|---|---|---|
| 26 | Ex. 12/ Ex. 8: TER1 (15%) | 15.2 | 4.4 | 0.67/0.33 |
| 27 | Ex. 13/ Ex. 13: TER2 (10%) | 14.3 | 4.1 | 0.67/0.33 |

TABLE 5

Blue-emitting OLEDs

| Ex. | EML | Efficiency [cd/A] | Voltage [V] | CIE, x/y |
|---|---|---|---|---|
| 67 | Ex. 40: SEB1 (5%) | 5.3 | 6.5 | 0.14/0.15 |
| 68 | Ex. 41: SEB1 (5%) | 5.2 | 6.4 | 0.14/0.15 |
| 69 | Ex. 42: SEB2 (1%) | 4.9 | 8.0 | 0.14/0.16 |
| 70 | Ex. 43: SEB2 (1%) | 5.5 | 5.2 | 0.14/0.16 |
| 71 | Ex. 44: SEB2 (1%) | 5.0 | 7.8 | 0.14/0.16 |
| 72 | Ex. 42: Ex. 45 (5%) | 4.0 | 6.0 | 0.15/0.18 |
| 73 | Ex. 42: Ex. 46 (5%) | 6.2 | 5.8 | 0.15/0.16 |

TABLE 6
Structural formulae of the materials used
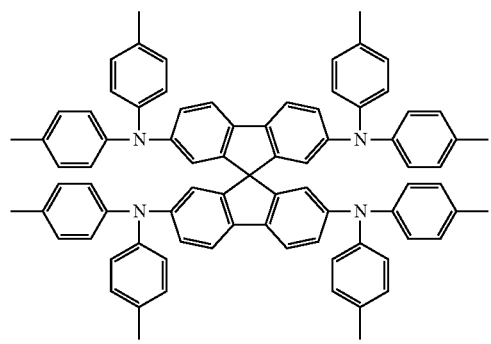
[515834-67-0]
HIL1
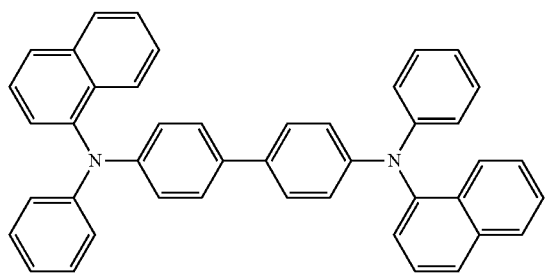
[123847-85-8]
HTM1 (NPB)
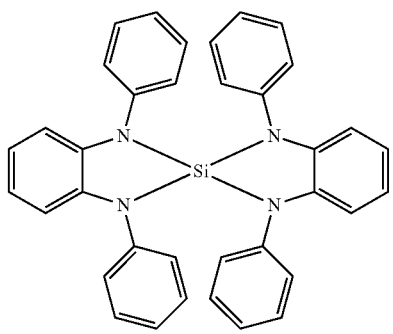
WO 2010/054729
EBL
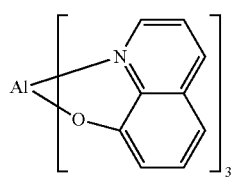
[2085-33-8]
ETM1 (Alq)
TABLE 6-continued
Structural formulae of the materials used
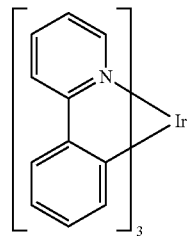
[94928-86-6]
TEG1
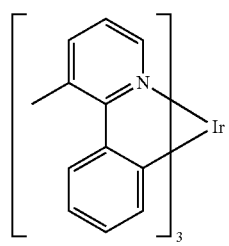
[359014-71-4]
TEG2
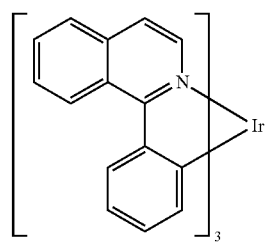
[435293-93-9]
TER1
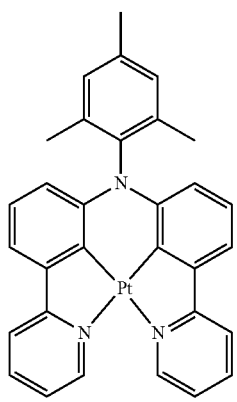
[851604-97-2]
TER2

TABLE 6-continued

Structural formulae of the materials used

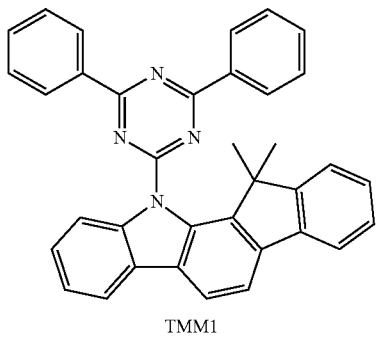

TMM1

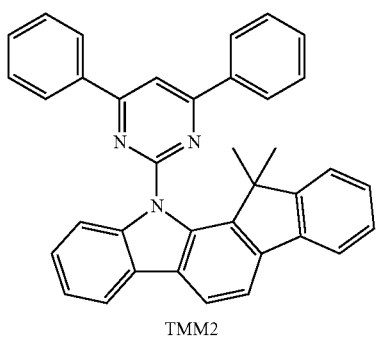

TMM2

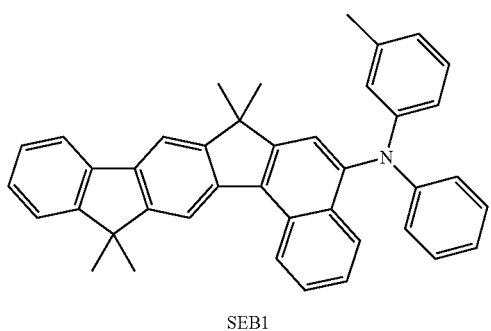 [SMILES: Cc1cccc(N(c2ccccc2)c2cc3c(c4ccccc24)-c2cc4c(cc2C3(C)C)-c2ccccc2C4(C)C)c1]

SEB1

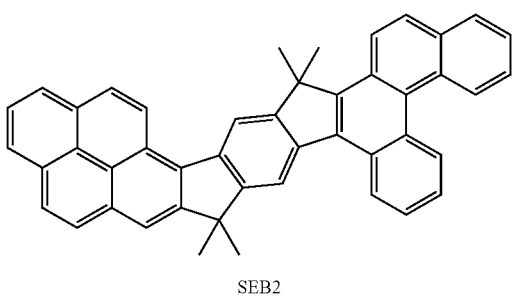 [SMILES: CC1(C)c2cc3c(cc2-c2c1cc1ccc4cccc5ccc2c1c45)C(C)(C)c1c-3c2ccccc2c2c1ccc1ccccc12]

SEB2

As is clearly evident from the examples given above, the materials according to the invention are particularly suitable for use as matrix materials for phosphorescent emitters and as hole conductors, where they result in high efficiencies and low operating voltages.

The invention claimed is:

1. A neutral compound of the formula (1),

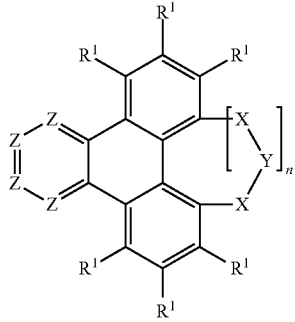

formula (1)

where the following applies to the symbols and indices used:

X is on each occurrence, identically or differently, $BR^2$, $Si(R^2)_2$ or $NR^2$;

or X is, for n=0, a group of the following formula (3),

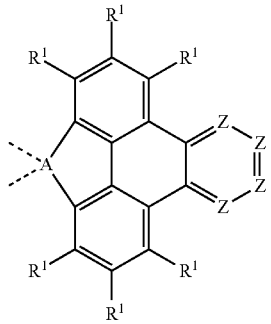

formula (3)

A is Si; the dashed bonds on A indicate the bonding to the triphenylene;

Y is $BR^2$, O, S, $NR^2$, $PR^2$ or $P(=O)R^2$;

Z is on each occurrence, identically or differently, $CR^1$ or N, with the proviso that a maximum of two groups Z per ring stand for N;

$Ar^1$ is on each occurrence, identically or differently, an aromatic or heteroaromatic ring system having 5 to 60 aromatic ring atoms, which is optionally substituted by one or more non-aromatic radicals $R^3$; two radicals $Ar^1$ which are bonded to the same N atom or P atom may also be bridged to one another by a single bond or a bridge selected from $N(R^4)$, $C(R^4)_2$, O or S;

$R^1$ is selected on each occurrence, identically or differently, from the group consisting of H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the alkyl, alkoxy, thioalkyl, alkenyl or alkynyl group is optionally substituted by one or more radicals $R^3$ and where one or more non-adjacent $CH_2$ groups is optionally replaced by $R^3C=CR^3$, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, an aromatic or heteroaromatic ring system having 5 to 60 aromatic ring atoms, which may in each case be substituted by one or more radicals R³, an aryloxy or heteroaryloxy group having 5 to 60 aromatic ring atoms, which is optionally substituted by one or more radicals R³, or a combination of these systems, where two or more adjacent substituents R¹ which are bonded to the same benzene ring may optionally form a monocyclic or polycyclic, aliphatic, aromatic or heteroaromatic ring system;

R² is selected on each occurrence, identically or differently, from the group consisting of a straight-chain alkyl group having 1 to 20 C atoms or a branched or cyclic alkyl group having 3 to 20 C atoms, each of which is optionally substituted by one or more radicals R³, where one or more non-adjacent CH₂ groups is optionally replaced by R³C=CR³, C≡C, Si(R³)₂, C=O, C=NR³, P(=O)(R³), SO, SO₂, NR³, O, S or CONR³ and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R³, where two substituents R² which are bonded to the same carbon, silicon, germanium or tin atom may optionally form a monocyclic or polycyclic, aliphatic, aromatic or heteroaromatic ring system with one another, which is optionally substituted by one or more radicals R³;

R³ is selected on each occurrence, identically or differently, from the group consisting of H, D, F, Cl, Br, I, CN, NO₂, N(R⁴)₂, C(=O)Ar¹, C(=O)R⁴, P(=O)(Ar¹)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the alkyl, alkoxy, thioalkyl, alkenyl or alkynyl group is optionally substituted by one or more radicals R⁴, where one or more non-adjacent CH₂ groups is optionally replaced by R⁴C=CR⁴, C≡C, Si(R⁴)₂, C=O, C=NR⁴, P(=O)(R⁴), SO, SO₂, NR⁴, O, S or CONR⁴ and where one or more H atoms is optionally replaced by D, F, Cl, Br, I, CN or NO₂, an aromatic or heteroaromatic ring system having 5 to 60 aromatic ring atoms, which may in each case be substituted by one or more radicals R⁴, an aryloxy or heteroaryloxy group having 5 to 60 aromatic ring atoms, which is optionally substituted by one or more radicals R⁴, or a combination of these systems, where two or more adjacent substituents R³ may optionally form a monocyclic or polycyclic, aliphatic, aromatic or heteroaromatic ring system, which is optionally substituted by one or more radicals R⁴;

R⁴ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I, CN or an alkyl group having 1 to 5 C atoms, where two or more adjacent substituents R⁴ may form a mono- or polycyclic, aliphatic, aromatic or heteroaromatic ring system with one another;

n is 0 or 1.

2. The compound according to claim 1, wherein the compound is selected from the compounds of the formulae (4) to (6),

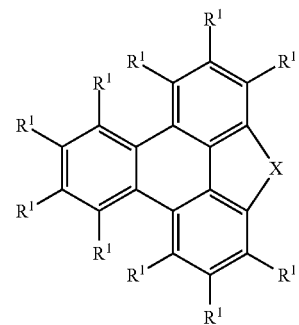

formula (4)

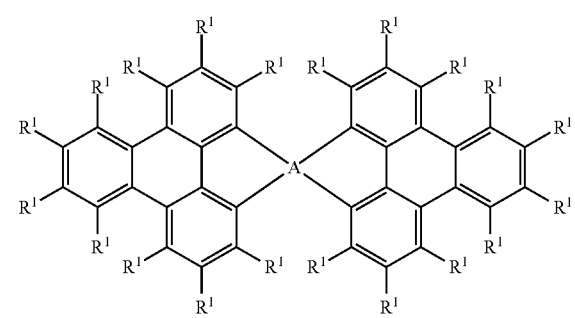

formula (5)

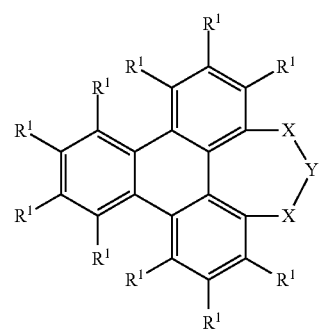

formula (6)

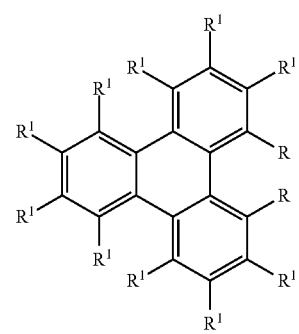

formula (7)

where the symbols used have the meanings given in claim 1.

3. The compound according to claim 1, wherein the compound is selected from the compounds of the formulae (4a) to (6a), formula (4a)
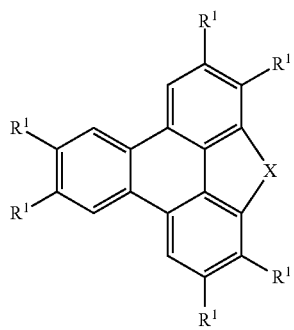
formula (5a)
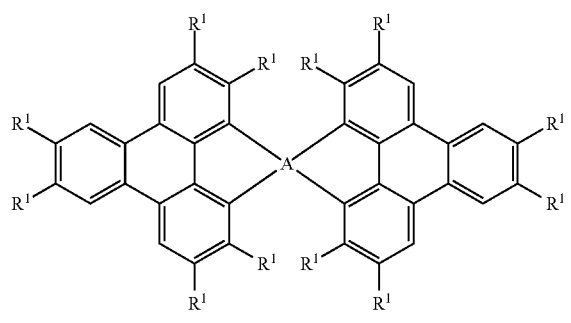
formula (6a)
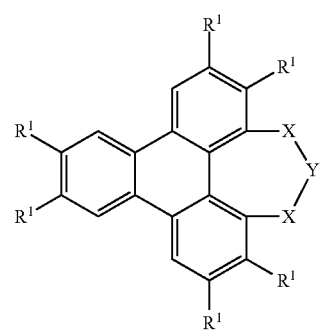
formula (7a)
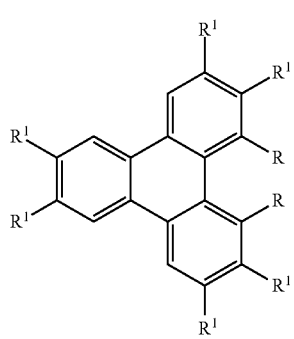
where the symbols used have the meanings given in claim 1.
4. The compound according claim 1, wherein the compound of formula (1) is selected from the group consisting of formula (4), (4a), (5), (5a), (6), or (6a),
formula (4)
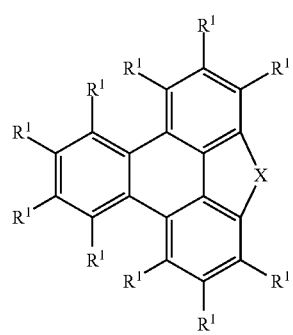
formula (4a)
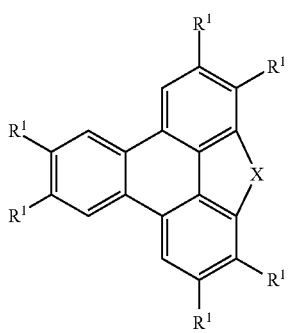
formula (5)
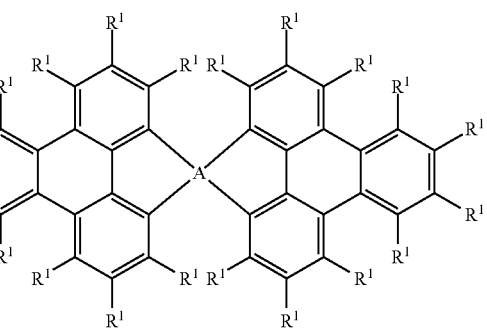
formula (5a)
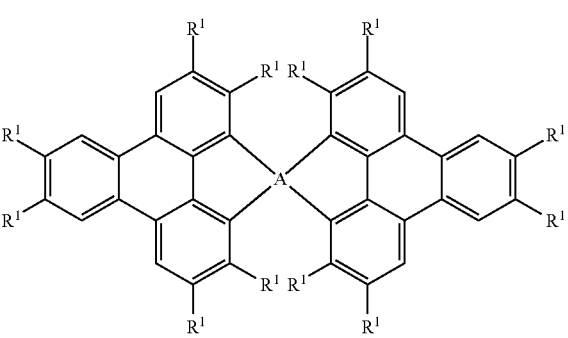

-continued

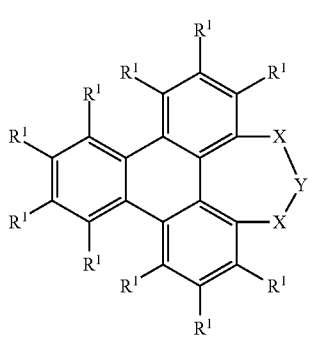

formula (6)

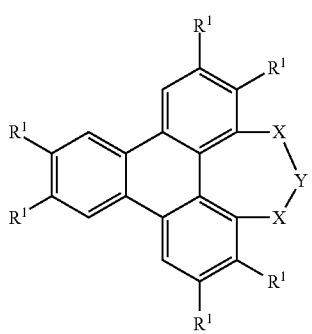

formula (6a)

wherein, in compounds of the formula (1) where n=0 or in compounds of the formula (4) or formula (4a), X is selected from the group consisting of Si(R²)₂ and N(R²) and R² stands, identically or differently on each occurrence, for an aromatic or heteroaromatic ring system having 5 to 40 aromatic ring atoms, which may in each case also be substituted by one or more radicals R³ and where two radicals R² may also form an aromatic ring system with one another;

and in that, in compounds of the formula (1) where X=formula (3) or in compounds of the formula (5) or formula (5a), the two triphenylene moieties which are bonded to A are in each case substituted identically and A stands for silicon;

and in that, in compounds of the formula (1) where n=1 or in compounds of the formula (6) or formula (6a), the group X—Y—X is Si(R²)₂—O—Si(R²)₂.

5. A process for the preparation of the compound according to claim 1 which comprises reacting 1,12-dilithiotriphenylene derivatives with electrophiles or by reaction of halogen- or amino-substituted triphenylene derivatives in a metal-catalyzed coupling reaction.

6. An oligomer, polymer or dendrimer containing one or more of the compounds according to claim 1, where one or more bonds are present from the compound to the polymer, oligomer or dendrimer.

7. An electronic device which comprises the compound according to claim 1.

8. An electronic device which comprises the oligomer, polymer or dendrimer according to claim 6.

9. The electronic device as claimed in claim 7, wherein the device is selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices.

10. An organic electroluminescent device which comprises the compound according to claim 1, wherein the compound is employed as matrix material for fluorescent or phosphorescent emitters and/or as fluorescent emitter and/or in a hole-blocking layer and/or in an electron-transport layer and/or in an electron-blocking or exciton-blocking layer and/or in a hole-transport or hole-injection layer and/or in an optical coupling-out layer.

11. An organic electroluminescent device which comprises the compound according to claim 1 is wherein the compound is employed as matrix material for phosphorescent emitters and in that at least one radical R¹ stands for N(Ar¹)₂, C(=O)Ar¹, P(=O)(Ar¹)₂ or for an aromatic or heteroaromatic ring system having 5 to 60 aromatic ring atoms, which is optionally substituted by one or more radicals R³, where the group Ar¹ or the radicals on Ar¹ or the aromatic or heteroaromatic ring system or the radicals R³ on the aromatic or heteroaromatic ring system contains no condensed aryl groups having more than 10 C atoms and no condensed heteroaryl groups in which more than two aryl or 6-membered heteroaryl groups are condensed directly onto one another.

12. The organic electroluminescent device according to claim 11, wherein at least one radical R¹ and/or R² is selected from the group consisting of phenyl, ortho-, meta- or para-biphenyl, ortho-, meta- or para-terphenyl, ortho-, meta-, para- or branched quater-phenyl, fluorene or spirobifluorene, each of which is optionally substituted by one or more radicals R³, and/or in that at least one radical R¹ and/or R² is selected from the structures of the formulae (8) to (38),

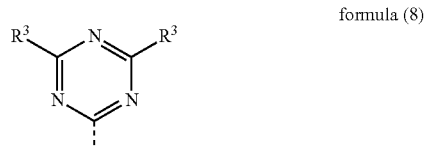

formula (8)

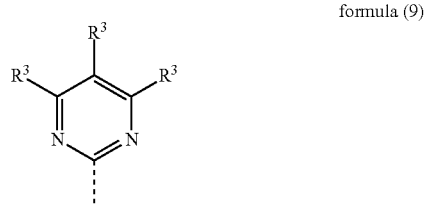

formula (9)

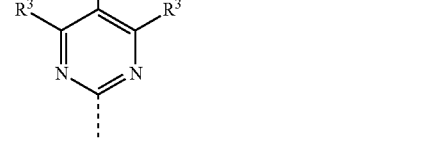

formula (10)

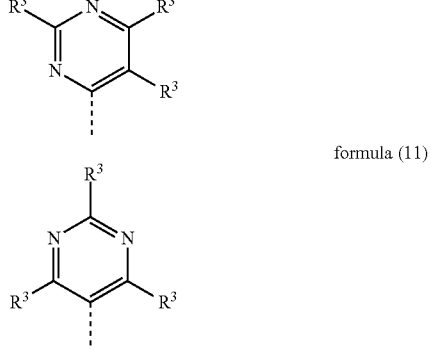

formula (11)

formula (12)
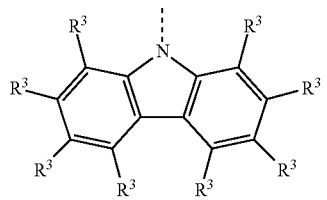
formula (13)
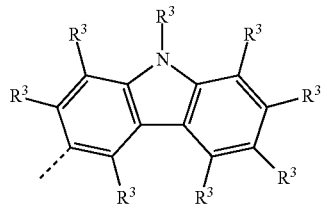
formula (14)
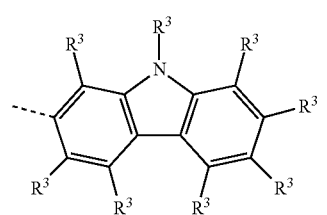
formula (15)
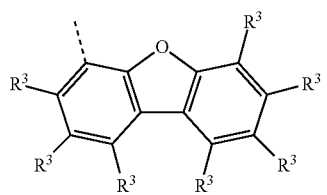
formula (16)
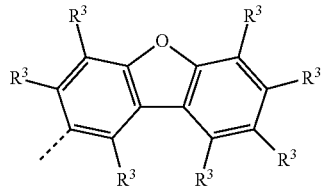
formula (17)
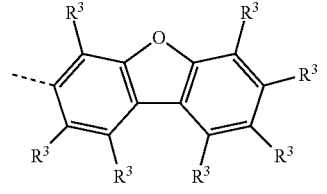
formula (18)
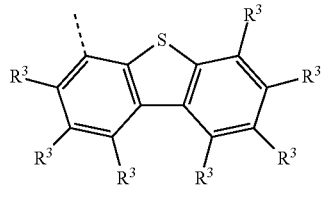
formula (19)
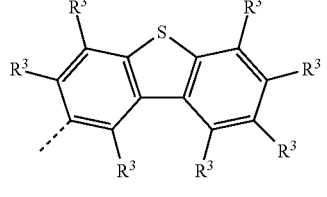
formula (20)
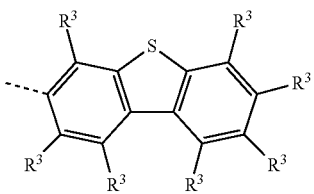
formula (21)
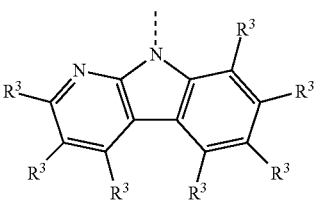
formula (22)
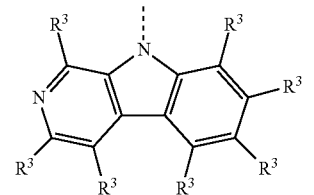
formula (23)
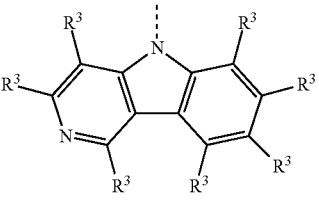
formula (24)
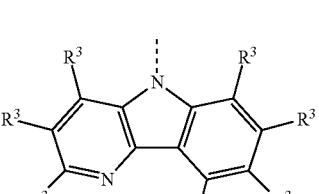
formula (25)
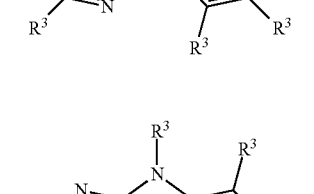
formula (26)
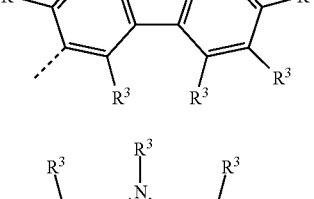
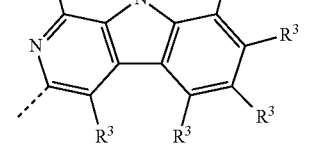

formula (27)
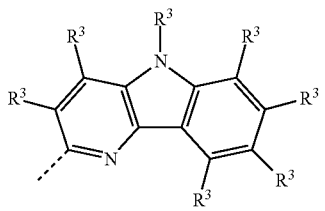

formula (28)
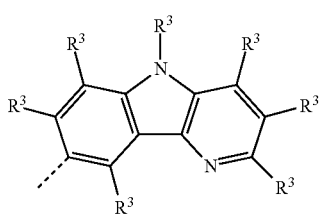

formula (29)
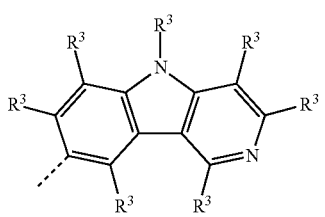

formula (30)
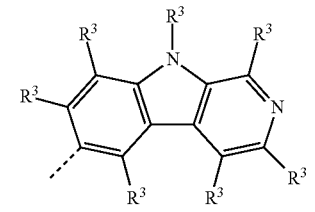

formula (31)
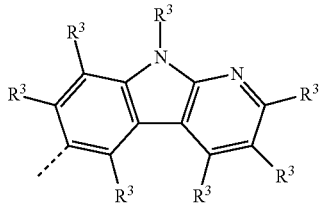

formula (32)
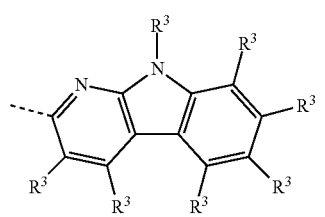

formula (33)
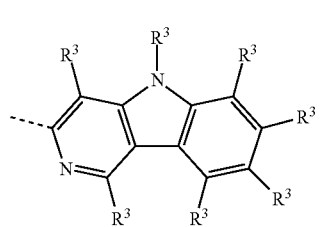

formula (34)
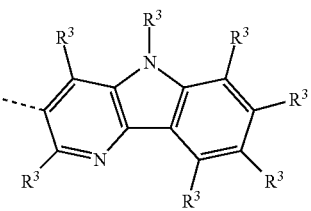

formula (35)
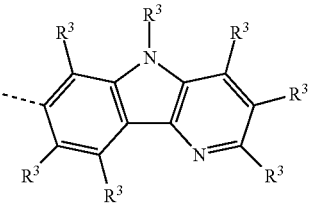

formula (36)
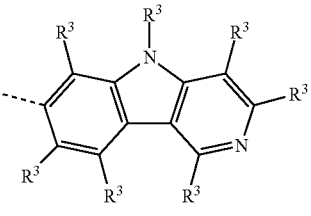

formula (37)
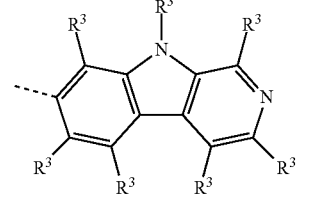

formula (38)
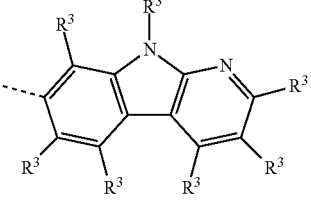

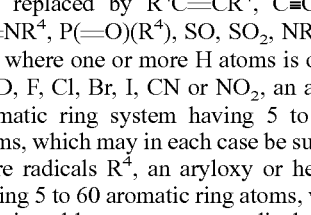

wherein
$R^3$ is selected on each occurrence, identically or differently, from the group consisting of H, D, F, Cl, Br, I, CN, $NO_2$, $N(R^4)_2$, C(=O)$Ar^1$, C(=O)$R^4$, P(=O)($Ar^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the alkyl, alkoxy, thioalkyl, alkenyl or alkynyl group is optionally substituted by one or more radicals $R^4$, where one or more non-adjacent $CH_2$ groups is optionally replaced by $R^4$C=C$R^4$, C≡C, Si($R^4$)$_2$, C=O, C=N$R^4$, P(=O)($R^4$), SO, $SO_2$, N$R^4$, O, S or CON$R^4$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^4$, an aryloxy or heteroaryloxy group having 5 to 60 aromatic ring atoms, which is optionally substituted by one or more radicals $R^4$, or a combination of these systems, where two or more adjacent substituents R³ may optionally form a monocyclic or polycyclic, aliphatic, aromatic or heteroaromatic ring system, which is optionally substituted by one or more radicals R⁴;

R⁴ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I, CN or an alkyl group having 1 to 5 C atoms, where two or more adjacent substituents R⁴ may form a mono- or polycyclic, aliphatic, aromatic or heteroaromatic ring system with one another;

Ar¹ is on each occurrence, identically or differently, an aromatic or heteroaromatic ring system having 5 to 60 aromatic ring atoms, which is optionally substituted by one or more non-aromatic radicals R³; two radicals Ar¹ which are bonded to the same N atom or P atom may also be bridged to one another by a single bond or a bridge selected from N(R⁴), C(R⁴)₂, O or S;

and the dashed bond represents the bond to the triphenylene skeleton or to X;

and/or in that at least one radical R¹ selected from the structures of the formulae (39) to (41) and/or in that at least one radical R² is selected from the structures of the formula (40),

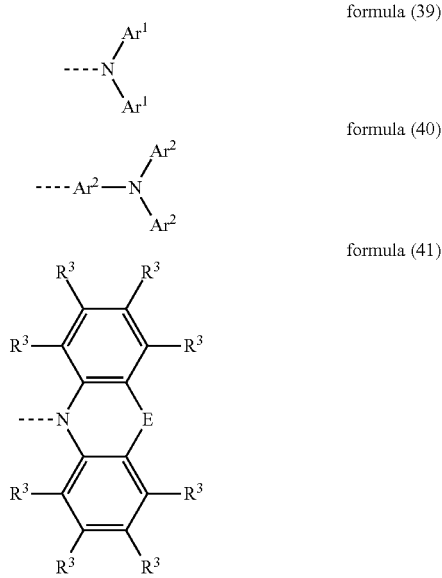

Ar² is, identically or differently on each occurrence, an aromatic or heteroaromatic ring system having 5 to 24 aromatic ring atoms, which is optionally substituted by one or more radicals R³; the sum of the aromatic ring atoms of all groups Ar² together is not greater than 60; and E is selected from the group consisting of C(R⁴)₂, NR⁴, O or S.

13. An organic electroluminescent device which comprises the compound according to claim 1 is wherein the compound is employed as electron-transport material and at least one radical R¹ stands for C(=O)Ar¹, P(=O)(Ar¹)₂ or for an electron-deficient heteroaromatic ring system having 5 to 40 aromatic ring atoms, which is optionally substituted by one or more radicals R³; and/or X stands for BR².

14. The organic electroluminescent device according to claim 13, wherein the electron-deficient heteroaromatic ring system R¹ and/or R² contains, as heteroaryl group, triazine, pyrimidine, pyrazine, pyridazine, pyridine, imidazole, pyrazole, oxazole, oxadiazole, triazole, thiazole, thiadiazole, benzimidazole, quinoline, isoquinoline or quinoxaline.

15. An organic electroluminescent device which comprises the compound according to claim 1 is wherein the compound is employed as hole-transport material or as emitting compound and at least one radical R¹ stands for N(Ar¹)₂, for a triarylamino group or for an electron-rich heteroaromatic ring system having 5 to 40 aromatic ring atoms, which is optionally substituted by one or more radicals R³; and/or X stands for NR².

16. A formulation comprising at least one compound according to claim 1 and at least one solvent.

17. A formulation comprising at least one or more polymers, oligomers or dendrimers according to claim 6 and at least one solvent.

18. The compound as claimed in claim 1, wherein the compound is

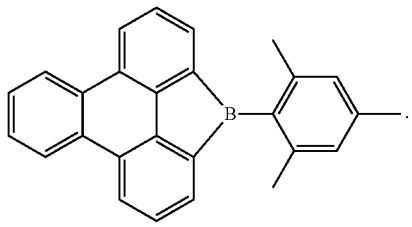 [SMILES: Cc1cc(C)c(B2c3cccc4c5ccccc5c5cccc2c5c34)c(C)c1]

19. An organic electroluminescent device which comprises the compound according to claim 1, wherein the compound is employed as matrix material for fluorescent emitter.

20. An organic electroluminescent device which comprises the compound according to claim 1, wherein the compound is employed as matrix material for in a hole-blocking layer.

* * * * *